US007005274B1

(12) United States Patent
Terkeltaub et al.

(10) Patent No.: US 7,005,274 B1
(45) Date of Patent: Feb. 28, 2006

(54) METHODS AND COMPOSITIONS FOR DIAGNOSING AND TREATING ARTHRITIC DISORDERS AND REGULATING BONE MASS

(75) Inventors: Robert Terkeltaub, San Diego, CA (US); Anne N. Murphy, Encinitas, CA (US); James A. Dykens, Encinitas, CA (US); Soumitra S. Ghosh, San Diego, CA (US); Robert E. Davis, San Diego, CA (US); Andrew E. Granston, Jr., San Diego, CA (US)

(73) Assignees: MIGENIX Corp., San Diego, CA (US); The Regents of the University of California, Oakland, CA (US)

( * ) Notice: Subject to any disclaimer, the term of this patent is extended or adjusted under 35 U.S.C. 154(b) by 684 days.

(21) Appl. No.: 09/661,848

(22) Filed: Sep. 14, 2000

Related U.S. Application Data

(60) Provisional application No. 60/154,145, filed on Sep. 15, 1999.

(51) Int. Cl.
$C12Q\ 1/02$ (2006.01)
(52) U.S. Cl. .......................... 435/29; 435/32; 435/375
(58) Field of Classification Search ................ 530/350, 530/913; 435/69.1, 78.1, 4, 7.8, 40.52, 40.51, 435/29, 32, 375
See application file for complete search history.

(56) References Cited

U.S. PATENT DOCUMENTS

| | | | |
|---|---|---|---|
| 4,846,835 A | 7/1989 | Grande | |
| 4,870,210 A | 9/1989 | Musser | |
| 5,041,138 A | 8/1991 | Vacanti et al. | |
| 5,656,450 A | 8/1997 | Boyan et al. | |
| 5,723,331 A | 3/1998 | Tubo et al. | |
| 5,736,372 A | 4/1998 | Vacanti et al. | |
| 5,786,217 A | 7/1998 | Tubo et al. | |
| 5,840,493 A | 11/1998 | Davis et al. | |
| 5,888,498 A | 3/1999 | Davis et al. | |
| 5,902,741 A | 5/1999 | Purchio et al. | |
| 5,928,945 A | 7/1999 | Seliktar et al. | |
| 5,932,459 A | 8/1999 | Sittinger et al. | |
| 5,935,796 A | 8/1999 | Fosang | |

FOREIGN PATENT DOCUMENTS

| | | |
|---|---|---|
| EP | 745850 | 12/1996 |
| WO | WO 99/37294 | 7/1999 |
| WO | WO 99/55321 | 11/1999 |
| WO | WO 00/06150 | 2/2000 |

OTHER PUBLICATIONS

Tabrizi et al. Secondary abnormalities of mitochondrial DNA associated with neurodegenerative disease. Biochem. Soc. Symp vol. 66 p99-110 2002.*

Terkeltaub et al. Invited review: the mitochondrion in osteoarthritis. Mitochondrion vol. 1 pp301-319 2002.*
Baker et al. The mechanism of chondrocyte hydrogen peroxide dambe. Depletion in intracellular ATP due to suppression of glycolysis caused by oxidation of glyceraldehyde-3-phosphate dehydrogenase. vol. 16 No. 1 1989 pp7-14.*
Alevizopoulos et al., "Transforming Growth Factor-β: the Breaking Open of a Black Box," *BioEssays* 19(7):581-591, Jul. 1997.
Al-Rubeai et al., "Cell Cycle, Cell Size and Mitochondrial Activity of Hybridoma Cells During Batch Cultivation," *Cytotechnology* 7(3):179-186, Nov. 1991.
Anderson, "Mechanisms of Pathologic Calcification," *Rheum. Dis. Clin. North Amer.* 14(2):303-319, Aug. 1988.
Anderson, "Molecular Biology of Matrix Vesicles," *Clin. Orthopaed. Rel. Res.* 314:266-280, May 1995.
Ausserer et al., "Regulation of c-jun Expression During Hypoxic and Low-Glucose Stress," *Mol. Cell. Biol.* 14(8): 5032-5042, Aug. 1994.
Batinić-Haberle et al., "The Ortho Effect Makes Manganese (III) Meso-Tetrakis(N-Methylpyridinium-2-yl)Porphyrin a Powerful and Potentially Useful Superoxide Dismutase Mimic," *J. Biol. Chem.* 273(38):24521-24528, Sep. 18, 1998.
Benya et al. "Dedifferentiated Chondrocytes Reexpress the Differentiated Collagen Phenotype When Cultured in Agarose Gels," *Cell* 30(1):215-224, Aug. 1982.
Bisaccia et al., "Kinetic Characterization of the Reconstituted Tricarboxylate Carrier from Rat Liver Mitochondria," *Biochem Biophys Acta.* 1019(3):250-256, Sep. 19, 1990.
Blanco et al., "Osteoarthritis Chondrocytes Die by Apoptosis. A Possible Pathway for Osteoarthritis Pathology, " *Arthritis & Rheumatism* 41(2):284-289, Feb. 1998.
Boskey et al., "Matrix Vesicles Promote Mineralization in a Gelatin Gel," *Calcif. Tissue Int.* 60(3):309-315, Mar. 1997.
Boskey, "Matrix Proteins and Mineralization: an Overview," *Connect. Tissue Res.* 35(1-4):357-363, 1996.

(Continued)

*Primary Examiner*—James Ketter
(74) *Attorney, Agent, or Firm*—Seed IP Law Group, PLLC

(57) ABSTRACT

The present invention relates to improved diagnostic methods for early detection of a risk for developing an arthritic disorder in humans, and screening assays for therapeutic agents useful in the treatment of arthritic disorders, by comparing the levels of one or more indicators of altered mitochondrial function. Indicators of altered mitochondrial function include enzymes such as mitochondrial enzymes and ATP biosynthesis factors. Other indicators of altered mitochondrial function include mitochondrial mass, mitochondrial number and mitochondrial DNA content, cellular responses to elevated intracellular calcium and to apoptogens, and free radical production. Methods of treating, and of stratifying, human patients as such methods relate to disclosed indicators of altered mitchondrial function are also provided.

6 Claims, 8 Drawing Sheets

OTHER PUBLICATIONS

Clark et al., "Transforming Growth Factor-beta (TGF-β)," *Int. J. Biochem. Cell. Biol.* 30(3):293-298, Mar. 1998.

Crompton et al., "On the Involvement of a Mitochondrial Pore in Reperfusion Injury," *Basic Res. Cardiol.* 88(5): 513-523, Sep.-Oct. 1993.

Day et al., "Metalloporphyrins are Potent Inhibitors of Lipid Peroxidation," *Free Radical Biology & Medicine* 26(5-6): 730-736, Mar. 1999.

Doherty, "Calcium Pyrophosphate in Joint Disease," *Hosp. Pract.* 29(11):93-104, Nov. 15, 1994.

Doyle, "Tissue Calcification and Inflammation in Osteoarthritis," *J. Pathol.* 136(3):199-216, Mar. 1982.

Dykens, *Mitochondria & Free Radicals in Neurodegenerative Diseases*, Beal, Howell and Bodis-Wollner, (Eds.), Wiley-Liss Inc., New York, 1997, Chapter 3, "Mitochondrial Free Radical Production and Oxidative Pathophysiology: Implications for Neurodegenerative Disease," pp. 29-55.

Ernster et al., "Mitochondria: A Historical Review," *J. Cell. Biol.* 91(3):227s-255s, Dec. 1981.

Farndale et al., "Improved Quantitation and Discrimination of Sulphated Glycosaminoglycans by Use of Dimethylmethylene Blue," *Biochim. Biophys. Acta* 883(2): 173-177, Sep. 4, 1986.

Fiermonte et al., "The Sequence, Bacterial Expression, and Functional Reconstitution of the Rat Mitochondrial Dicarboxylate Transporter Cloned via Distant Homologs in Yeast and *Caenorhabditis elegans*," *J. Biol. Chem.* 273(38): 24754-24759, Sep. 18, 1998.

Fiore et al., "The Mitochondrial ADP/ATP Carrier: Structural, Physiological and Pathological Aspects," *Biochimie* 80:137-150, 1998.

Gilliland et al., "Disorders of the Joints and Connective Tissue," Section 14, in *Harrison's Principles of Internal Medicine*, Eighth Ed., Thorn et al., (Eds.), McGraw-Hill, New York, NY, 1977, pp. 2048-2080.

Glowacki et al., "Cell Shape and Phenotypic Expression in Chondrocytes," *Proc. Soc. Exp. Biol. Med.* 172(1):93-98, Jan. 1983.

Goldberg et al., "Lipids and Biomineralization-An Overview," *Prog. Histochem. Cytochem.*, 31(2):1-187, 1996.

Green et al., "Mitochondria and Apoptosis," *Science* 281: 1309-1312, Aug. 28, 1998.

Green, "Apoptotic Pathways: The Roads to Ruin," *Cell* 94:695-698, Sep. 18, 1998.

Gunter et al., "Mechanisms by Which Mitochondria Transport Calcium." *Am. J. Physiol.* 27(5Pt1): C755-C786, May. 1990.

Gunter et al., "Mitochondrial Calcium Transport: Physiological and Pathological Relevance,", *Am. J. Physiol.* 267 (2Pt1):C313-C339, Aug. 1994.

Gunter et al., "The $Ca^{2+}$Transport Mechanisms of Mitochondria and $Ca^{2+}$Uptake From Physiological-Type $Ca^{2+}$Transients," *Biochim. Biophys. Acta* 1366:5-15, 1998.

Gunter et al., "Transport of Calcium by Mitochondria," *J. Bioenerg. Biomembr.* 26(5):471-485, 1994.

Hyc et al., "Immunological Response Against Allogeneic Chondrocytes Transplanted Into Joint Surface Defects in Rats," *Cell. Transplant.* 6(2):119-124, Mar.-Apr. 1997.

Indiveri et al., "Kinetic Characterization of the Reconstituted Dicarboxylate Carrier from Mitochondria: a Four-Binding-Site Sequential Transport System," *Biochim. Biophys. Acta* 1143(3):310-318, Jul. 26, 1993.

Iacobazzi et al., "Cloning and Sequencing of the Bovine cDNA Encoding the Mitochondrial Tricarboxylate Carrier Protein," *Biochim. Biophys. Acta* 1284(1):9-12, Oct. 2, 1996.

Ježek et al., "Mammalian mitochondrial uncoupling proteins."*Int J Biochem Cell Biol* 30(11):1163-1168, Nov. 1998.

Johnson et al., "Matrix Vesicle Plasma Cell Membrane Glycoprotein-1 Regulates Mineralization by Murine Osteoblastic MC3T3 Cells," *J. Bone Miner. Res.* 14(6):883-892, Jun. 1999.

Kapùs et al., "Is the Mitochondrial $Ca^{2+}$Uniporter a Voltage-Modulated Transport Pathway?," *FEBS Lett.* 282:61-64, Apr. 1991.

Karbowski et al., "Cycloheximide and 4-OH-TEMPO Suppress Chloramphenicol-Induced Apoptosis in RL-34 Cells Via the Suppression of the Formation of Megamitochondria,"*Biochim. Biophys. Acta* 1449(1):25-40, Feb. 4, 1999.

Klingenberg, "Principles of Carrier Catalysis Elucidated by Comparing Two Similar Membrane Translocators from Mitochondria, the ADP/ATP Carrier and the Uncoupling Protein," *Annals New York Academy of Sciences* 456:279-288, 1985.

Kliot-Fields et al., "Purification of Cybrids by Fluorescence-Activated Cell Sorting," *Somatic Cell. Genet.* 9(3):375-389, May 1983.

Korsmeyer et al, "Reactive Oxygen Species and the Regulation of Cell Death by the Bcl-2 Gene Family," *Biochim. Biophys. Act.* 1271:63-66, 1995.

Kowaltowski et al., "Mitochondrial Damage Induced by Conditions of Oxidative Stress," *Free Radical Biol. Med.* 26(3-4):463-471, Feb. 1999.

Kroemer et al., "The Biochemistry of Programmed Cell Death," *FASEB J.* 9(13):1277-87, Oct. 1995.

Kroemer, "The Proto-Oncogene Bcl-2 and its Role in Regulating Apoptosis," *Nature Medicine* 3(6):614-620, Jun. 1997.

Leist et al., "Calcium and Neuronal Death," *Rev. Physiol. Biochem. Pharmacol.* 132:79-125, 1998.

Litsky et al., "Regulation of the Mitochondrial $Ca^+$Uniporter by External Adenine Nucleotides: the Uniporter Behaves Like a Gated Channel Which is Regulated by Nucleotides and Divalent Cations" *Biochem.* 36(23):7071-7080, Jun. 10, 1997.

Liu et al., "Induction of Apoptotic Program in Cell-Free Extracts: Requirement for dATP and Cytochrome c" *Cell* 86:147-157, Jul. 12, 1996.

Luyten et al., *Biological Regulation of the Chondrocytes*, Adolphe, Ed., CRC Press, Boca Raton, 1992, Chater 9, "Articular Cartilage Repair:Potential Role of Growth and Differentiation Factors," pp. 227-236.

Manella, "Minireview: On the Structure and Gating Mechanism of the Mitochondrial Channel, VDAC," *J. Bioenergetics Biomembr.* 29(6):525-531, Dec. 1997.

Marchetti et al., "Apoptosis-Associated Derangement of Mitochondrial Function in Cells Lacking Mitochondrial DNA," *Cancer Res.* 56:2033-2038, May 1, 1996.

Massagué, "TGF-β Signal Transduction," *Annu. Rev. Biochem.* 67:753-791, 1998.

Monaghan et al., "Ultrastructural Localization of BCL-2 Protein," *J. Histochem. Cytochem.* 40(12):1819-1825, 1992.

Murphy et al., *Mitochondria and Free Radicals in Neurodegenerative Diseases*, Beal, Howell and Bodis-Wollner, (Eds.), Wiley-Liss Inc., New York, 1997, Chapter 8, "Mitochondria, Reactive Oxygen Species, and Apoptosis," pp. 159-186.

Newmeyer et al., "Cell-Free Apoptosis in Xenopus Egg Extracts: Inhibition by Bcl-2 and Requirement for an Organelle Fraction Enriched in Mitochondria," *Cell* 79:353-364, Oct. 21, 1994.

Petit et al., "Mouse Testis Cell Sorting According to DNA and Mitochondrial Changes During Spermatogenesis," *Cytometry* 19(4):304-312, Apr. 1, 1995.

Pujol et al., "Transforming Growth Factor-β (TGF-β) and Articular Chondrocytes," *Annales d'Endocrinologie (Paris)* 55(2):109-120, 1994.

Radi et al., *Mitochondria & Free Radicals in Neurodegenerative Diseases*, Beal, Howell and Bodis-Wollner, (Eds.), Wiley-Liss Inc., New York, 1997, Chatper 4, "Free Radical Damage to Mitochondria," pp. 57-89.

Rice-Evans et al., "Structure-Antioxidant Activity Relationships of Flavoniods and Phenolic Acids," *Free Radical Biology & Medicine* 20(7):933-956, 1996.

Roberts et al., "TGF-β: Regulation of Extracellular Matrix," *Kidney Intl.* 41(3):557-559, Mar. 1992.

Romaniuk et al., "Rejection of Cartilage Formed by Transplanted Allogeneic Chondrocytes: Evaluation With Monoclonal Antibodies," *Transpl. Immunol.* 3(3):251-257, Sep. 1995.

Rosen et al., "Differential Effects of Aging on Human Chondrocyte Responses to Transforming Growth Factor β: Increased Pyrophosphate Production and Decreased Cell Proliferation," *Arthritis Rheum.* 40(7):1275-1281, Jul. 1997.

Rottenberg et al., "Regulation of Ca2+ Transport in Brain Mitochondria. II. The Mechanism of the Adenine Nucleotides Enhancement of $Ca^{2+}$Uptake and Retention," *Biochim. Biophys. Acta* 1016(1):87-98, Mar. 15, 1990.

Stefanovic-Racic et al., "Nitric Oxide and Energy Production in Articular Chondrocytes," *J. Cell Physiol.* 159(2):274-280, May. 1994.

Sztrolovics et al., "Resistance of Small Leucine-Rich Repeat Proteoglycans to Proteolytic Degradation During Interleukin-1-Stimulated Cartilage Catabolism," *Biochim. J.* 339(Pt 3):571-577, May 1, 1999.

Terkeltaub et al., "Parathyroid Hormone-Related Proteins is Abundant in Osteoarthritic Cartilage, and the Parathyroid Hormone-Related Protein 1-173 Isoform is Selectively Induced by Transforming Growth Factor β in Articular Chondrocytes and Suppresses Generation of Extracellular Inorganic Pyrophosphate," *Arthritis Rheum.* 41(12):2152-2164, Dec. 1998.

Terkeltaub, "The Immortalized Chondrocyte: Art Without Sacrifice," *J. Clin. Invest.* 94(6):2173, Dec. 1994.

Van Beuningen et al., "Transforming Growth Factor-β1 Stimulates Articular Chondrocyte Proteoglycan Synthesis and Induces Osteophyte Formation in the Murine Knee Joint," *Lab. Invest.* 71(2):279-290, Aug. 1994.

Walker et al., "Structural Analysis of ATP Synthase from Bovine Heart Mitochondria," *Methods in Enzymology* 260:163-190, 1995.

Walker et al., "Structural Analysis of NADH: Ubiquinone Oxidoreductase from Bovine Heart Mitochondria," *Meths. Enzymol.* 260:14-34, 1995.

Zamzami et al., "Reduction in Mitochondrial Potential Constitutes an Early Irreversible Step of Programmed Lymphocyte Death in Vivo," *J. Exp. Med.* 181:1661-1672, May 1995.

Zamzami et al., "Sequential Reduction of Mitochondrial Transmembrane Potential and Generation of Reactive Oxygen Species in Early Programmed Cell Death," *J. Exp. Med.* 182:367-377, Aug. 1995.

Zoratti et al., "Electrophysiology of the Inner Mitochondrial Membrane," *J. Bioenergetics Biomembr.* 26(5):543-553, Oct. 1994.

Chichester et al., "Immunological detection of type II collagen degradation: use in the evaluation of anti-arthritic therapies," *J. Pharmaceutical Pharmacology* 48(7):694-698, Jul. 1996.

Corvo et al., "Intravenous administration of superoxide dismutase entrapped in long circulating liposomes. II. In vivo fate in a rat model of adjuvant arthritis," *Biochim. Biophys. Acta* 1419(2):325-334, Jul. 15, 1999.

Galleron et al., "Reactive oxygen species induce apoptosis of synoviocytes in vitro, α-tocopherol provides no protection," *Cell Biology International* 23(9):637-642, 1999.

Johnson et al., "Differential mechanisms of inorganic pyrophosphate production by plasma cell membrane glycoprotein-1 and B10 in chondrocytes," *Arthritis & Rheumatism* 42(9):1986-1997, Sep. 1999.

Palmoski et al., "Marked suppression by salicylate of the augmented proteoglycan synthesis in osteoarthritic cartilage," *Arthritis & Rheumatism* 23(1):83-91, Jan. 1980.

Pullig et al., "Metabolic activation of chondrocytes in human osteoarthritis. Expression of type II collagen," *Zeitschrift Fuer Orthopaedie und Ihre Grenzgebiete* 137(1):67-75, 1999. (English Summary on p. 67).

Terkeltaub et al., "Casual link between nucleotide pyrophosphohydrolase overactivity and increased intracellular inorganic pyrophosphate generation demonstrated by transfection of cultured fibroblasts and osteoblasts with plasma cell membrane glycoprotein-1. Relevance to calcium pyrophosphate dihydrate deposition disease," *Arthritis & Rheumatism* 37(6):934-941, Jun. 1994.

Ali, "Aptite-Type Crystal Deposition in Arthritic Cartilage," *Scanning Electron Microscopy* 4:1555-1566, 1985.

Altman, "A Metabolic Dysfunction in Early Murine Osteoarthritis," *Annals of the Rheumatic Diseases* 40:303-306, 1981.

Baginsky et al., "The Role of Hydroxyl Radicals in Rodent Models of Artbritis," *FASEB Journal* 11(3):A332, 1997.

Baynes and Thorpe, "Role of Oxidative Stress in Diabetic Complications. A New Perpsective on an Old Paradigm," *Diabetes* 48(1):1-9, Jan. 1999.

Boos et al., "Immunohistochemical Analysis of Type X-Collagen Expression in Osteoarthritis of the Hip Joint," *Journal of Orthopaedic Research* 17(4):495-502, Jul. 1999.

Cencetti et al., "Superoxide Anion Production by Circulating Polymorphonuclear Leucocytes in Rheumatiod Arthritis," *Clinical Rheumatology* 9(1):51-55, 1990.

Chapman et al., "Increased Carbonyl Content of Proteins in Synovial Fluid for Patients with Rheumatoid Arthritis," *Journal of Rheumatology* 16(1):15-18, 1989.

Cheung et al., "Specific Inhibition of Basic Calcium Phosphate and Calcium Pyrophosphate Crystal-Induction of Metalloproteinase Synthesis by Phosphocitrate," *Biochimica et Biophysica Acta* 1315 (2):105-111, 1996.

Cush et al., "US Consensus Guidelines for the Use of Cyclosporin A in Rheumatiod Arthritis," *Journal of Rheumatology* 26(5):1176-1186, May 5, 1999.

Glansbeek et al., "Stimulation of Articular Cartilage Repair in Established Arthritis by Local Administration of Transforming Growth Factor-β into Murine Knee Joints," *Laboratory Investigation* 78(2):133-142, Feb. 1998.

Griffey et al., "Depletion of High-Energy Phosphates in the Central Nervous System of Patients with Systemic Lupus Erythematosus, as Determined by Phosphorus-31 Nuclear Magnetic Resonance Spectroscopy," *Arthritis and Rheumatism* 33(6):827-833, Jun. 1990.

Ishii et al., "Effect of Growth Factors and Cytokines on Experimentally-Induced Osteoarthritic Chondocytes," *Nihon University Journal of Medicine* 40(5):245-255, Oct. 1998.

Hassan et al., "Protective Effects of Antioxidants Against Rheumatiod Arthritis-Induced Lipid Peroxidation and Glutathione Depletion," *Research Communications in Pharmacology and Toxicology* 3(3&4):105-113, 1998.

Johnson et al., "Mitochondrial Oxidative Phosphorylation is a Downstream Regulator of Nitric Oxide Effects on Chondrocyte Matrix Synthesis and Mineralization," *Arthritis and Rhematism* 43(7):1560-1570, Jul. 2000.

Kaplan et al., "Propranolol and the Treatment of Rheumatoid Arthritis," *Arthritis and Rheumatism* 23(2): 253-255, Feb. 1980.

Lafeber et al., "Transforming Growth Factor-β Predominantly Stimulates Phenotypically Changed Chondrocytes in Osteoarthritic Human Cartilage," *Journal of Rheumatology* 24(3):536-542, 1997.

Lunec et al., "A Marker of Oxidative DNA Damage in Systemic Lupus Erythematosus," *FEBS Letters* 348:131-138. 1994.

Marinello et al., "The Purine Nucleotide Content of Lymphocytes for Patients with Rheumatoid Arthritis," *Int. J. Clin. Pharm. Res.* 14(2):57-63, 1994.

Mark et al., "Type X Collagen Synthesis in Human Osteoarthritic Cartilage," *Arthritis and Rheumatism* 35(7): 806-811, Jul. 1992.

Meydani et al., "Urinary 8-OhdG as a Marker of Oxidative Stress in Rheumatoid Arthritis (RA) and Aging: Effect of Progressive Resistance Training (PRT)," *FASEB J.* 11(3): A377, 1997.

Miyata et al., "Increased Pentosidine, an Advanced Glycation End Product, in Plasma and Synovial Fluid from Patients with Rheumatoit Arthritis and Its Relation with Inflammatory Markers," *Biochemical and Biophysical Research Communications* 244(1):45-49, Mar. 6, 1998.

Nordemar et al., "Muscle ATP Content in Rheumatoid Arthritis—a Biopsy Study," *Scandinavian Journal of Clinical and Laboratory Investigation* 34(2):185-191, 1974.

Pratta et al., "Effect of Ebselen on IL-1-Induced Alterations in Carilage Metabolism," *Inflammation Research* 47(3):115-121, 1998.

Rediske et al., "Nitric Oxide and Osteoarthritis: Pathways of Protein Nitros-Ylationin Chondrocytes," *Arthritis and Rheumatism* 40(9 Suppl.):S184, Sep. 1997.

Rosenthal, "Calcium Crystal-Associated Arthritides," *Current Opinion in Rheumatology* 10(3):273-277, May 1998.

Rush et al., "The Mechanism of Acute Cytotoxicity of Triethylphosphine Gold(I) Complexes. II. Triethylphosphine Gold Chloride-Induced Alterations in Mitochondrial Function," *Toxicology and Applied Pharmacology* 90(3):391-400, 1987.

Sauleda et al., "Activity of Cytochrome Oxidase is Increased in Circulating Lymphocytes of Patients with Chronic Obstructive Pulmonary Disease, Asthma, and Chronic Arthritis," *American Journal of Respiratory and Critical Care Medicine* 161(1):32-35, Jan. 2000.

Tanka and Gátai, "Role of Mitochondrial Enzymes in the Pathomechanism of Rheumatoid Arthritis," *Acta Biochimica et Biophysica Academiae Scientiarum Hungaricae* 19(1-2): 116, 1984.*

Tanka and Keller, "Electron Transporting Enzymes of Rheumatoid Connective Tissue," *Acta Morphologica Acad. Sci. Hung.* 25(2-3):137-146, 1977.*

Tomita et al., "Nitric Oxide Regulates Mitochondrial Respiration and Functions of Articular Chondrocytes," *Arthritis & Rheumatism* 44(1):96-104, Jan. 2001.*

Willer et al., "Effects of Creatine Supplementation on Muscle Weakness in Patients with Rheumatoid Arthritis," *Rheumatology* 39(3):293-298, Mar. 2000.*

Yamada et al., "Differential Display Analysis of Murine Collagen-Induced Arthritis: Cloning of the cDNA-Encoding Murine ATPase Inhibitor," *Immunology* 92(4):571-576, Dec. 1997.*

Dijkgraaf, L. et al., "Calcium Pyrophosphate Dihydrate Crystal Deposition Disease: A Review of the Literature and a Light and Electron Microscopic Study of a Case of the Temporomandibular Joint with Numerous Intracellular Crystals in the Chondrocytes," *Osteoarthritis and Cartilage* 3(1):35-45, Mar. 1995.

Neumüller, J. et al., "Untersuchungen über Zelluläre und Homorale Immunphänomene Bei der Arthritis Psoriatica," *Wiener Klinische Wochenschrift* 95(12):416-422, Jun. 1983.

Ryan, L. et al., "Synovial Fluid ATP: A Potential Substrate for the Production of Inorganic Pyrophosphate," *Journal of Rheumatology* 18:716-720, 1991.

* cited by examiner

METHODS AND COMPOSITIONS FOR DIAGNOSING AND TREATING ARTHRITIC DISORDERS AND REGULATING BONE MASS

CROSS-REFERENCE TO RELATED APPLICATIONS

This application claims the benefit of U.S. Provisional Patent Application No. 60/154,145 filed Sep. 15, 1999, which is incorporated herein by reference in its entirety.

STATEMENT OF POTENTIAL GOVERNMENT RIGHTS IN THE INVENTION

Part of the invention was made in the course of research sponsored by NIH grant number P01AG07996 and by a Merit Review Award from the Veterans Affairs Medical Service to one of the inventors (R. T.). The United States Government may have certain rights in this invention.

TECHNICAL FIELD

The present invention relates generally to arthritis and related disorders. In particular, the invention relates to compositions and methods for the diagnosis, prognosis and treatment of osteoarthritis and rheumatoid arthritis, and for preventing bone loss.

BACKGROUND OF THE INVENTION

Numerous chronic debilitating diseases of the skeletal system in vertebrates, including arthritis and related arthritic disorders, feature degradation of specialized avascular cartilaginous tissue known as articular cartilage that contains dedicated cartilage-producing cells, the articular chondrocytes. As described in greater detail below, articular chondrocytes, unlike other chondrocytes such as epiphyseal growth plate chondrocytes present at the ends of developing long bones (e.g., endochondral or costochondral chondrocytes), reside in and maintain joint cartilage having no vasculature. Thus lacking a blood supply as an oxygen source, articular chondrocytes are believed to generate metabolic energy, for example bioenergetic ATP production, predominantly by anaerobic (e.g., glycolytic) respiration, and not from aerobic mitochondrial oxidative phosphorylation (Stefanovich-Racic et al., 1994 *J. Cell Physiol.* 159: 274–280). Because even under aerobic conditions, articular chondrocytes may consume little oxygen and thus appear to differ from a wide variety of vertebrate cell types (Stefanoviceh-Racic et al., 1994), mitochondrial roles in arthritic disorders have been largely ignored.

I. Structure and Function of Musculoskeletal Joints

Evolution has developed extraordinarily efficient musculoskeletal systems for generating and controlling motion in vertebrates such as mammals, reptiles, birds and fish. The musculoskeletal system thus efficiently delivers useful mechanical energy and load support, but is also capable of synthesizing, processing and organizing complex macromolecules to fashion tissues and organs specialized to perform specific mechanical functions. The joints are an important subset of the specialized structures of the musculoskeletal system, and many distinct types of joints exist in the body. Freely moving joints (e.g., ankle, elbow, hip, knee, shoulder, and joints of the fingers, toes and wrist) are known as diarthrodial or synovial joints. In contrast, the intervertebral joints of the spine are not diarthrodial joints as they are fibrous and do not move freely, although they do provide the flexibility required by the spine.

Diarthrodial joints have some common structural features. First, all diarthrodial joints are enclosed in a strong fibrous capsule. Second, the inner surfaces of the joint capsule are lined with a metabolically active tissue, the synovium, which secretes the synovial fluid that lubricates the joint and provides the nutrients required by the avascular cartilage. Third, the articulating bone ends in the joint are lined with a thin layer of hydrated soft tissue known as articular cartilage. Fourth, the joint is stabilized by, and its range of motion controlled by, ligaments and tendons that may be inside or outside the joint capsule.

The surface linings of diarthrodial joints, i.e., the synovium and articular cartilage layers, form the joint cavity that contains the synovial fluid. Thus, in vertebrate skeletal joints, the synovial fluid, articular cartilage, and the supporting bone form a smooth, nearly frictionless bearing system. While diarthrodial joints are subjected to an enormous and varied range of load conditions, the cartilage surfaces undergo little wear and tear (e.g., structural degradation) under normal circumstances. Indeed, most human joints are capable of functioning effectively under very high loads and stresses and at very low operating speeds. These performance characteristics demand efficient lubrication processes to minimize friction and wear of cartilage in the joint. Severe breakdown of the joint cartilage by biochemical and/or biomechanical processes leads to arthritis, which is therefore generally defined as a failure of the vertebrate weight bearing system.

Hyaline cartilage, as its name implies, is glass-smooth, glistening and bluish white in appearance, although older or diseased tissue tends to lose this appearance. The most common hyaline cartilage, and the most studied, is the articular cartilage, which covers the articulating surfaces of long boned and siesamoid bones within diarthrodial joints. As described above, articular cartilage consists of specialized cartilage cells known as articular chondrocytes, and a cartilaginous extracellular matrix comprised largely of two major classes of macromolecules, collagen and proteoglycans. Articular chondrocytes synthesize, deposit and reside in the three-dimensional extracellular matrix, and also synthesize some of the solutes and enzymes present in synovial fluid, which bathes the articular cartilage. Healthy articular cartilage forms a smooth surface between articulating bone ends to reduce the friction caused by movement. The synovial fluid further reduces this friction.

During the development of cartilage (chondrogenesis), chondroblasts derived from mesenchymal cells become trapped in small cavities or depressions known as lacunae, where they develop into articular chondrocytes which, in contrast to chondroblasts, have a limited capacity to replicate. Articular chondrocytes, however, mediate the synthesis, assembly, degradation and turnover of the macromolecules which comprise the cartilage extracellular matrix (ECM or simply "matrix"). Mechanochemical properties of this matrix contribute significantly to the biomechanical function of cartilage in vivo. Because the articular cartilage is not a vascularized tissue, articular chondrocytes are believed to reside in an environment of low oxygen tension and may therefore appear to preferentially derive metabolic energy by anaerobic (e.g., glycolytic) ATP biosynthesis (Stefanovich-Racic et al., 1994).

The structural integrity of articular cartilage is the foundation of optimal functioning of the skeletal joints, such as those found in the vertebrate hip, shoulders, elbows, hocks and stifles. Impaired skeletal joint function dramatically reduces an individual subject's mobility, such as that involved in rising from a sitting position or in climbing and descending stairs. As noted above, in order to maintain the structural and functional integrity of articular cartilage, articular chondrocytes constantly synthesize collagen and proteoglycans, the major components of the articular cartilage; chondrocytes also secrete the friction-reducing synovial fluid. This constant elaboration by articular chondrocytes of cartilage ECM macromolecules and synovial fluid provides the articular cartilage with a repair mechanism for most mechanical wear that may be caused by friction between the bone ends. However, such steady biosynthesis of cartilage components generates a constant demand for the precursors, or building blocks, of these macromolecules and synovial fluid components. Lack of these precursors will lead to defects in the structure and function of the skeletal joints. This deficiency occurs often when activity levels are very high, or when cartilage tissue is traumatized.

The menisci of the knee, and other similar structures such as the disc of the temporomandibular joint and the labrum of the shoulder, are specialized fibrocartilagenous structures that are vital for normal joint function. They are known to assist articular cartilage in distributing loads across the joint, to aid ligaments and tendons in stabilizing joints and to play a major role in shock absorption, and may further assist in lubricating the joint. Damage to these structures can lead to impaired joint function and to articular cartilage degeneration. Surgical removal of these fibrocartilagenous structures, for example, following apparently irreparable cartilage tears, can result in early onset of osteoarthritis. The menisci, disc and labrum are hydrated fibrocartilage structures composed primarily of type II collagen, with smaller amounts of other collagens and proteoglycans (including aggrecan and the smaller, non-aggregating proteoglycans) also present. These fibrocartilaginous structures contain a sparse population of resident cells that, like the articular chondrocytes of cartilage, are responsible for the synthesis and maintenance of this extracellular matrix.

II. Arthritic Disorders

Diarthrodial joints enable common bodily motions including limb movements associated with motor (e.g., ambulatory) functions and other activities of daily life. These joints typically perform their functions so well and efficiently that their existence may be innocuous until injury strikes or arthritis develops. From an engineering point of view, these natural biomechanical bearings are very uncommon structures. Healthy joints may function in a virtually frictionless and wear-resistant manner throughout all or most of a lifetime. Failure of the joint bearings surfaces (i.e., articular cartilage), as with mechanically engineered artificial bearings, means a failure of these bearings to provide their central functions, such as delivery of mechanical energy and load support.

In biomedical terms, failure of diarthrodial joints leads to arthritic disorders, the most common forms being osteoarthritis or degenerative joint disease, or chondrocalcinosis. Other forms of arthritic disorders include but are not limited to rheumatoid arthritis, juvenile rheumatoid arthritis, ankylosing spondylitis, Reiter's syndrome, psoriatic arthritis, lupus erythematosous, gout and infectious arthritides (see, e.g., Gilliland et al., "Disorders of the joints and connective tissue," Section 14, in *Harrison's Principles of Internal Medicine*, Eighth Ed., Thorn et al., eds. McGraw-Hill, New York, N.Y., 1977, pp. 2048–2080). Arthritic disorders can also include, or may result from, physical trauma (for example, acute physical injury that damages joint tissue, or repetitive motion syndrome) or dietary conditions (e.g., ricketts or other dietary deficiency diseases) that result in joint injury.

By far, the most prevalent arthritic disorders are rheumatoid arthritis (RA) and osteoarthritis (OA). RA, thought to be an autoimmune disorder, results in part from inflammation of the synovial membrane. In humans, peak onset of this disorder occurs in adults over 30 years of age (typically in their thirties and forties) and afflicts women three times more often than men. In extreme cases, chronic inflammation erodes and distorts the joint surfaces and connective tissue, resulting in severe articular deformity and constant pain. Moreover, RA often leads to OA, further compounding the destruction of the joint. The most common arthritic disorder, OA, is characterized by degenerative changes in the surface of the articular cartilage. Alterations in the physicochemical structure of the cartilage make it less resistant to compressive and tensile forces. Finally, complete erosion occurs, leaving the subchondral bone exposed and susceptible to wear. Joints of the knees and hands are most often affected, as also may be one or more of the spine, hips, ankles and shoulders. In both RA and OA, degeneration of the weight bearing joints such as the hips and knees can be especially debilitating and often requires surgery to relieve pain and increase mobility.

No means currently exist for halting or reversing the degenerative changes brought about by RA and related arthritic disorders. At the same time, approximately 37 million Americans seek symptomatic relief in the form of prescription drugs. In such cases nonsteroidal, anti-inflammatory drugs (NSAIDS) are most often prescribed. While these compounds often alleviate or palliate the arthritic symptoms, they frequently have undesirable side effects, for example, nausea and gastrointestinal ulceration. Other compounds commonly prescribed for the treatment of arthritic disorders are the corticosteroids, such as triamcinolone, prednisolone and hydrocortisone. These drugs also have undesirable side effects, particularly where long term use may be required, and so may be contraindicated in many patients. In addition to difficulties in determining effective dosages, a number of adverse reactions have been reported during intra-articular treatment with these and other steroids. As a result, the use of corticosteroid treatments in the management of arthritic disorders is currently being reassessed.

As an alternative to symptomatic and palliative measures for treating OA and RA as described above, mechanical repair of arthritic joints, when feasible, involves orthopedic surgery to replace worn joints with an artificial prosthesis, or with a biological graft. With more than thirty million Americans suffering from these disabling diseases, such surgery poses enormous medical and economic challenges and is not without its own risks and contraindications.

Osteoarthritis, also known as degenerative joint disease, is one of the most common types of arthritis. It is characterized by the breakdown of the cartilage within a joint, causing painful rubbing of one bone of the joint against another bone and leading to a loss of movement within the affected joint. Osteoarthritis can range from very mild to very severe, and most commonly affects middle-aged and older people. In particular, OA often affects hands and weight-bearing joints such as the knees, hips, feet and back. Although age is a leading risk factor, at present the etiology and pathogenesis of this condition remains largely unknown. Many environmental factors and other independent conditions have been associated with an increased risk for having or developing osteoarthritis, including obesity, previous injury and/or menisectomy (e.g., sports-related injuries or other accidental injury), occupation-related activities that involve repeated knee bending, smoking, sex hormones, gynecological disorders and other metabolic factors. Chondrocalcinosis is another form of degenerative joint disease related to osteoarthritis, in which abnormal calcification occurs in the articular cartilage.

At present accurate diagnosis of osteoarthritis is in general possible only when the disease has progressed significantly. Physicians can do little more than make a diagnosis of osteoarthritis based on a physical examination and a history of symptoms. Examination by X-ray is typically used only to confirm diagnosis. A recent study concluded that weight loss in middle-aged people who are overweight can significantly reduce the risk or even prevent osteoarthritis of the knee from developing. In such cases, improved accuracy in diagnosing an individual's predisposition to developing osteoarthritis would provide distinct advantages.

Accordingly, as provided herein, certain embodiments of the present invention are drawn to compositions and methods for the diagnosis of arthritis and related disorders. In related embodiments, the invention provides compositions and screening methods for compounds that can be used to treat such disorders, preferably using high-throughput screening methods as known in the art or later developed based on the disclosures herein. Such treatment can be remedial, therapeutic, palliative, rehabilitative, preventative, impeditive or prophylactic in nature.

III. Canine Hip Dysplasia and Other Disorders in Non-Human Animals

In certain embodiments the invention relates to compositions and methods for the early diagnosis of dogs affected with canine hip dysplasia. In related embodiments, the invention pertains in part to compositions and methods for the diagnosis of arthritis, dysplasia and related diseases and disorders in other non-human animals.

Canine hip dysplasia is a common orthopedic disease affecting millions of dogs in the United States alone. Canine hip dysplasia affects many breeds of dogs, but is of particular high incidence in the larger breeds. Included in the more than 80 affected canine breeds are German shepherd, Newfoundland, Old English sheepdog, English bulldog, Labrador retriever, other retriever breeds, Irish setter, Great Dane, and St. Bernard. The disease is characterized by laxity and incongruity of the hip joint, which results in degeneration of joint tissues. Osteoarthritis develops as a result of the abnormal positioning of the head of the femur in relation to the joint due to laxity, and results in the erosion of joint cartilage, and inflammation of the synovium. The development in a dog of osteoarthritis in a dysplastic hip joint is a benchmark sign of canine hip dysplasia.

Canine hip dysplasia is believed to be a hereditary disease of complex genetic and environmental bases. Clinical symptoms range from mild hip joint discomfort to severe debilitation, and the disease is the most common cause of lameness in posterior limbs and joints. However, in most cases the clinical symptoms of dysplasia appear in affected dogs late in life and long after initiation of the disease process, which may commence during the first 6 to 12 months of age. Early diagnosis (e.g., at less than one year of age) of canine hip dysplasia is desirable and useful, for example, to permit dog breeders to accurately identify affected dogs at an early age in order to remove affected dogs from breeding programs. Early diagnosis may also permit treatment before disease progression can advance. For example, management of the affected dog's weight through physical activity and diet may be initiated to limit strain on the hip joints.

Alternatively, Biocompatible Osteoconductive Polymer (BOP) shelf arthroplasty, a surgical procedure in which a polymer is used to rebuild the defective hips of dysplastic dogs to prevent subluxation, may be elected.

A current method for detecting hip dysplasia, disclosed in U.S. Pat. No. 5,482,055, is based on compression-distraction stress radiography. This method measures joint laxity that is related to the presence or absence of osteoarthritis (Smith et al., 1993 Am. J. Vet. Res. 54:1021–42; Smith et al., 1990 J. Am. Vet. Med. Assoc. 196:59–70). This stress method elicits passive laxity, which is the maximal lateral displacement of the femoral heads that occurs when a force is used to distract the hip joint. An adjustable device, a "distractor", is used to reveal passive laxity, and to quantify lateral displacement of the femoral head by a measurement called the "distraction index". This index is used as a measure of passive laxity and as a predictive value, wherein below a certain value it is unlikely that the dog will develop osteoarthritis. For example, in Labrador retrievers, a distraction index of 0.3 is indicative of tight hip joints, and an index of >0.7 is indicative of loose hip joints (passive laxity). Thus, as the distraction index increases from 0.3 to 0.7, the probability of the development of osteoarthritis increases. However, a problem arises in that the outcome for Labradors having a distraction index in this range cannot reliably be predicted (Smith et al., 1993, supra; Lust et al., 1993 Am. J. Vet. Res. 54:1990–9). Likely reasons include the other components of the hip joint structure, such as acetabular and femoral head conformation, which contribute to functional joint stability and prevent the conversion of intermediate degrees of passive laxity into hip subluxation during ambulation.

IV. Mitochondria

As noted above, because metabolic energy production in vertebrate articular chondrocytes is believed to proceed via anaerobic respiration (e.g., glycolytic ATP synthesis), little or no attention has been paid to the relationship between mitochondrial oxidative phosphorylation and arthritic disorders. By way of background, mitochondria are the main energy source in cells of higher organisms, and provide direct and indirect biochemical regulation of a wide array of cellular respiratory, oxidative and metabolic processes. Such processes include electron transport chain (ETC) activity, which drives oxidative phosphorylation to produce metabolic energy in the form of adenosine triphosphate (ATP), and which also underlies a central mitochondrial role in intracellular calcium homeostasis.

Mitochondrial ultrastructural characterization reveals the presence of an outer mitochondrial membrane that serves as an interface between the organelle and the cytosol, a highly folded inner mitochondrial membrane that appears to form attachments to the outer membrane at multiple sites, and an intermembrane space between the two mitochondrial membranes. The subcompartment within the inner mitochondrial membrane is commonly referred to as the mitochondrial matrix. (For a review, see, e.g., Ernster et al., 1981 J. Cell Biol. 91:227s.) The cristae, originally postulated to occur as infoldings of the inner mitochondrial membrane, have recently been characterized using three-dimensional electron tomography as also including tube-like conduits that may form networks, and that can be connected to the inner membrane by open, circular (30 nm diameter) junctions (Perkins et al., 1997, Journal of Structural Biology 119:260). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (>~10 kDa) molecules.

Altered or defective mitochondrial activity, including but not limited to failure at any step of the ETC, may result in catastrophic mitochondrial collapse that has been termed "permeability transition" (PT) or "mitochondrial permeability transition" (MPT). According to generally accepted theories of mitochondrial function, proper ETC respiratory activity requires maintenance of an electrochemical potential ($\Delta\Psi m$) in the inner mitochondrial membrane by a coupled chemiosmotic mechanism. Altered or defective mitochondrial activity may dissipate this membrane potential, thereby preventing ATP biosynthesis and halting the production of a vital biochemical energy source. In addition, mitochondrial proteins such as cytochrome c or intermembrane space proteins may leak out of the mitochondria after permeability transition and may induce the genetically programmed cell suicide sequence known as apoptosis or programmed cell death (PCD).

Four of the five multi-subunit protein complexes (Complexes I, III, IV and V) that mediate ETC activity are localized to the inner mitochondrial membrane, which is the most protein rich of biological membranes in cells (75% by weight); the remaining ETC complex (Complex II) is situated in the matrix. In at least three distinct chemical reactions known to take place within the ETC, positively-charged protons are moved from the mitochondrial matrix, across the inner membrane, to the intermembrane space. This disequilibrium of charged species creates an electrochemical potential of approximately 220 mV referred to as the "proton motive force" (PMF), which is often represented by the notation $\Delta\psi$ or $\Delta\psi m$ and represents the sum of the electric potential and the pH differential across the inner mitochondrial membrane (see, e.g., Ernster et al., 1981 *J. Cell Biol.* 91:227s and references cited therein).

This membrane potential provides the energy contributed to the phosphate bond created when adenosine diphosphate (ADP) is phosphorylated to yield ATP by ETC Complex V, a process that is "coupled" stoichiometrically with transport of a proton into the matrix; $\Delta\psi m$ is also the driving force for the influx of cytosolic $Ca^{2+}$ into the mitochondrion. Under normal metabolic conditions, the inner membrane is largely impermeable to proton movement from the intermembrane space into the matrix, leaving ETC Complex V as the primary means whereby protons can return to the matrix. When, however, the integrity of the inner mitochondrial membrane is compromised, as occurs during MPT that may accompany a disease associated with altered mitochondrial function, protons are able to bypass the conduit of Complex V without generating ATP, thereby "uncoupling" respiration because electron transfer and associated proton pumping yields no ATP. Thus, mitochondrial permeability transition involves the opening of a mitochondrial membrane "pore", a process by which, inter alia, the ETC and $\Delta\psi m$ are uncoupled, $\Delta\psi m$ collapses and mitochondrial membranes lose the ability to selectively regulate permeability to solutes both small (e.g., ionic $Ca^{2+}$, $Na^+$, $K^+$, $H^+$) and large (e.g., proteins).

The mitochondrial permeability transition "pore" may not be a discrete assembly or multi-subunit complex, and the term thus refers instead to any mitochondrial molecular component (including, e.g., a mitochondrial membrane per se) that regulates the inner membrane selective permeability where such regulated function is impaired during MPT. A mitochondrial molecular component may be a protein, polypeptide, peptide, amino acid or derivative thereof; a lipid, fatty acid or the like, or derivative thereof; a carbohydrate, saccharide or the like or derivative thereof; a nucleic acid, nucleotide, nucleoside, purine, pyrimidine or related molecule, or derivative thereof, or the like; or any other biological molecule that is a constituent of a mitochondrion. A mitochondrial pore component may be any mitochondrial molecular component that regulates the selective permeability characteristic of mitochondrial membranes as described above, including those responsible for establishing $\Delta\Psi m$ and those that are functionally modified during MPT.

Without wishing to be bound by theory, it is unresolved whether this pore is a physically discrete conduit that is formed in mitochondrial membranes, for example by assembly or aggregation of particular mitochondrial and/or cytosolic proteins and possibly other molecular species, or whether the opening of the "pore" may simply represent a general increase in the porosity of the mitochondrial membrane. In any event, certain mitochondrial molecular components may contribute to the MPT mechanism, including ETC components or other mitochondrial components described herein. For example, some non-limiting examples of mitochondrial or mitochondria associated proteins that appear to contribute to the MPT mechanism include members of the voltage dependent anion channel (VDAC, also known as porin) family of proteins, the mitochondrial calcium uniporter, mitochondria associated hexokinase(s), peripheral benzodiazepine receptor, and intermembrane creatine kinases.

MPT may result from direct or indirect effects of mitochondrial genes, gene products or downstream mediator molecules and/or extramitochondrial genes, gene products or downstream mediators. MPT may also result from other known or unknown causes. Loss of mitochondrial potential may be a critical event in the progression of diseases associated with altered mitochondrial function, including degenerative diseases.

Mitochondrial defects may contribute significantly to the pathogenesis of diseases associated with altered mitochondrial function. Such defects may be related to the discrete mitochondrial genome that resides in mitochondrial DNA and/or to the extramitochondrial genome, which includes nuclear chromosomal DNA and other extramitochondrial DNA, For example, alterations in the structural and/or functional properties of mitochondrial components, including alterations deriving from genetic and/or environmental factors or alterations derived from cellular compensatory mechanisms, may play a role in the pathogenesis of any disease associated with altered mitochondrial function.

A number of degenerative diseases are thought to be caused by, or to be associated with, alterations (e.g., increases or decreases) in mitochondrial function. Without wishing to be bound by theory, such alterations may be global, manifesting themselves in virtually all cell and tissue types in an affected individual, or they may be more apparent in specific cell or tissue types that appear particularly relevant to a given disease. Diseases associated with altered mitochondrial function include disorders that are accompanied by neurodegeneration (e.g., Alzheimer's Disease (AD); Parkinson's Disease; Huntington's disease; dystonia; Leber's hereditary optic neuropathy; schizophrenia; mitochondrial encephalopathy, lactic acidosis, and stroke (MELAS); and myoclonic epilepsy, ragged red fiber syndrome (MERRF), cancer) as well as disorders in which degeneration of other specialized tissues may be present (e.g., psoriasis; hyperproliferative disorders; mitochondrial diabetes and deafness (MIDD); and diabetes mellitus. The extensive list of additional diseases associated with altered mitochondrial function continues to expand as aberrant mitochondrial or mitonuclear activities are implicated in particular disease processes.

A hallmark pathology of AD and potentially other diseases associated with altered mitochondrial function is the death of selected cellular populations in particular affected tissues, which results from apoptosis (also referred to as "programmed cell death" or PCD). Mitochondrial dysfunction is thought to be critical in the cascade of events leading to apoptosis in various cell types (Kroemer et al., *FASEB J.* 9:1277–87, 1995). Altered mitochondrial physiology may be among the earliest events in PCD (Zamzami et al., *J. Exp. Med.* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994).

Thus, in addition to their role in energy production in growing cells, mitochondria (or, at least, mitochondrial components) participate in apoptosis (Newmeyer et al., 1994, *Cell* 79:353–364; Liu et al., 1996, *Cell* 86:147–157). Apoptosis is apparently also required for, inter alia, normal development of specialized tissues (e.g., ablation of obsolete cells during developmentally programmed tissue remodeling) and proper functioning of the immune system. Moreover, some disease states are thought to be associated with either insufficient (e.g., cancer, autoimmune diseases) or excessive (e.g., stroke damage, AD-associated neurodegeneration) levels of apoptosis. For general reviews of apoptosis, and the role of mitochondria therein, see Green and Reed (1998, *Science* 281:1309–1312), Green (1998, *Cell* 94:695–698) and Kromer (1997, *Nature Medicine* 3:614–620). Hence, agents that affect apoptotic events, including those associated with mitochondrial components, might have a variety of palliative, prophylactic and therapeutic uses.

From the foregoing, it is clear that none of the current pharmacological therapies corrects the underlying biochemical defect in arthritic disorders such as RA and OA. Neither do any of these currently available treatments improve all of the physiological abnormalities in arthritic disorders such as abnormal articular chondrocyte activity, cartilage degradation, articular erosion and severe joint deformity. In addition, treatment failures are common with these agents, such that multi-drug therapy is frequently necessary.

Clearly there is a need for improved diagnostic methods for early detection of a risk for developing an arthritic disorder, and for better therapeutics that are targeted to correct biochemical and/or metabolic defects responsible for this disease, regardless of whether such a defect underlying altered mitochondrial function may have mitochondrial or extramitochondrial origins. The present invention provides compositions and methods related to indicators of altered mitochondrial function that are useful for determining the risk and degree of progression of an arthritic disorder and for treating this disease, and offers other related advantages.

SUMMARY OF THE INVENTION

In one aspect, the present invention provides a method for identifying a risk for an arthritic disorder in a vertebrate subject, comprising comparing the level of at least one indicator of altered mitochondrial function in a biological sample from the subject with a control sample, wherein an altered level of the indicator indicates that the subject has or is at risk for developing an arthritic disorder; and therefrom identifying the risk for the arthritic disorder.

It is another aspect of the invention to provide a method for determining a degree of disease progression in a vertebrate subject having an arthritic disorder, comprising comparing the level of at least one indicator of altered mitochondrial function in each of first and second biological samples, the first and second biological samples being obtained from the subject at a first time point and a second time point, respectively, wherein an altered level of the indicator between the first and second time points indicates progression of disease; and therefrom determining the degree of progression of the arthritic disorder.

In still another aspect, the invention provides a method of identifying an agent suitable for treating a vertebrate subject suspected of being at risk for having an arthritic disorder, comprising comparing the level of at least one indicator of altered mitochondrial function in one or more biological samples obtained from the subject in the presence and absence of a candidate agent, wherein an altered level of the indicator indicates that the agent alters mitochondrial function; and therefrom determining the suitability of the candidate agent for treating the arthritic disorder.

Turning to another aspect, the present invention provides a method of determining the suitability of an agent for treating a vertebrate subject suspected of being at risk for having an arthritic disorder, comprising comparing the level of at least one indicator of altered mitochondrial function in a biological sample obtained from the subject before and after administering to the subject a candidate agent, wherein an altered level of the indicator indicates that the agent alters mitochondrial function; and therefrom determining the suitability of the candidate agent for treating the arthritic disorder.

It is another aspect of the invention to provide a method of determining the suitability of an agent for treating a vertebrate subject suspected of being at risk for having an arthritic disorder, comprising comparing the level of at least one indicator of altered mitochondrial function in at least one biological sample obtained from a plurality of subjects before and after administering to each of the subjects a candidate agent, wherein an altered level of the indicator indicates that the agent alters mitochondrial function; and therefrom determining the suitability of the candidate agent for treating the arthritic disorder.

In yet another aspect, the invention provides a method of stratifying subjects of a vertebrate species according to subtypes of an arthritic disorder, comprising comparing the level of at least one indicator of altered mitochondrial function in at least one biological sample obtained from each of a plurality of subjects of the species; and therefrom stratifying the subjects according to subtypes of the arthritic disorder.

In another aspect, the invention provides a method of stratifying subjects of a vertebrate species according to subtypes of an arthritic disorder, comprising comparing the level of at least one indicator of altered mitochondrial function in a biological sample obtained from each of a plurality of subjects of the species before and after administering to each of the subjects a candidate agent, wherein an altered level of the indicator indicates that the agent alters mitochondrial function; and therefrom stratifying the subjects according to subtypes of the arthritic disorder.

In certain embodiments of the foregoing aspects of the invention, the vertebrate subject is a human, a dog, a cow, a pig, a cat, a horse, a goat or a sheep, and in one particularly preferred embodiment the vertebrate subject is a human. In certain other embodiments the arthritic disorder is osteoarthritis, degenerative joint disease, rheumatoid arthritis, juvenile rheumatoid arthritis, chondrocalcinosis, ankylosing spondylitis, Reiter's syndrome, psoriatic arthritis, dysplasia, lupus erythematosous, gout or infectious arthritides.

In certain embodiments the biological sample comprises a chondrocyte or a hematopoietic cell, and in certain further embodiments the chondrocyte is an articular chondrocyte, while in certain other further embodiments the hematopoietic cell is a platelet or a nucleated peripheral blood cell, which in certain still further embodiments is a lymphocyte, a monocyte or a granulocyte. In some embodiments the biological sample comprises an articular chondrocyte and the act of comparing comprises comparing the level of at least one indicator of altered mitochondrial function in the absence and presence of transforming growth factor-beta. In a further embodiment, the indicator of altered mitochondrial activity is nucleotide pyrophosphohydrolase. In certain embodiments, the biological sample comprises a matrix vesicle derived from a chondrocyte and the indicator of altered mitochondrial function is pyrophosphate, ATP or nucleotide pyrophosphohydrolase. In another embodiment, the biological sample comprises a chondrocyte and the indicator of altered mitochondrial function is elaboration by the chondrocyte of at least one extracellular matrix component. In a further embodiment, the act of comparing comprises comparing the level of at least one extracellular matrix component that is elaborated in the absence and presence of transforming growth factor-beta. In another further embodiment, the extracellular matrix component is collagen, proteoglycan, inorganic pyrophosphate, calcium phosphate or calcium pyrophosphate dihydrate (CPPD). In certain still further embodiments the collagen is type I collagen, type II collagen, type X collagen or type XI collagen. In other embodiments, the biological sample comprises a cybrid cell.

In some embodiments, the step of comparing comprises comparing the level of at least one indicator of altered mitochondrial function in the absence and presence of at least one inhibitor of mitochondrial function under conditions and for a time sufficient to decrease the activity of at least one electron transport chain enzyme without decreasing glycolysis. In further embodiments, the inhibitor of mitochondrial function is antimycin, oligomycin, rotenone or cyanide. In other embodiments, the indicator of altered mitochondrial function is a mitochondrial electron transport chain enzyme, and in certain further embodiments the step of comparing comprises measuring electron transport chain enzyme catalytic activity. In certain still further embodiments the step of measuring comprises determining enzyme activity per mitochondrion in the sample. In another embodiment the step of measuring comprises determining enzyme activity per unit of protein in the sample, and in another embodiment the step of comparing comprises measuring electron transport chain enzyme quantity. In a further embodiment the step of measuring comprises determining enzyme quantity per mitochondrion in the sample, and in another embodiment the step of measuring comprises determining enzyme quantity per unit of protein in the sample. In some embodiments the mitochondrial electron transport chain enzyme comprises at least one subunit of mitochondrial complex I; in other embodiments the mitochondrial electron transport chain enzyme comprises at least one subunit of mitochondrial complex II; in other embodiments the mitochondrial electron transport chain enzyme comprises at least one subunit of mitochondrial complex III; in other embodiments the mitochondrial electron transport chain enzyme comprises at least one subunit of mitochondrial complex IV; in certain further embodiments the at least one subunit of mitochondrial complex IV is COX1, COX2 or COX4; and in other embodiments the mitochondrial electron transport chain enzyme comprises at least one subunit of mitochondrial complex V. In a further embodiment the at least one subunit of mitochondrial complex V is ATP synthase subunit 8 or ATP synthase subunit 6.

In some embodiments the indicator of altered mitochondrial function is the amount of ATP per cell in the sample, and in certain further embodiments the step of comparing comprises measuring the amount of ATP per mitochondrion in the sample. In certain other further embodiments the step of comparing comprises measuring the amount of ATP per unit protein in the sample, and in certain other embodiments the step of comparing comprises measuring the amount of ATP per unit mitochondrial mass in the sample; in still other embodiments the step of comparing comprises measuring the amount of ATP per unit mitochondrial protein in the sample. In some embodiments the indicator of altered mitochondrial function is the rate of ATP synthesis in the sample. In other embodiments the indicator of altered mitochondrial function is an ATP biosynthesis factor. In another embodiment the step of comparing comprises measuring ATP biosynthesis factor catalytic activity, and in a further embodiment the step of measuring comprises determining ATP biosynthesis factor activity per mitochondrion in the sample. In another embodiment the step of measuring comprises determining ATP biosynthesis factor activity per unit mitochondrial mass in the sample, and in another embodiment the step of measuring comprises determining ATP biosynthesis factor activity per unit of protein in the sample. In another embodiment the step of comparing comprises measuring ATP biosynthesis factor quantity, and in a further embodiment the step of measuring comprises determining ATP biosynthesis factor quantity per mitochondrion in the sample. In another embodiment the step of measuring comprises determining ATP biosynthesis factor quantity per unit of protein in the sample.

In certain embodiments of the invention, the indicator of altered mitochondrial function is a mitochondrial matrix component, and in certain other embodiments the indicator of altered mitochondrial function is a mitochondrial membrane component. In some further embodiments, the mitochondrial membrane component is a mitochondrial inner membrane component, and in certain still further embodiments the mitochondrial membrane component is adenine nucleotide translocator (ANT), voltage dependent anion channel (VDAC), malate-aspartate shuttle, calcium uniporter, UCP-1, UCP-2, UCP-3, a hexokinase, a peripheral benzodiazepine receptor, a mitochondrial intermembrane creatine kinase, cyclophilin D, a Bcl-2 gene family encoded polypeptide, tricarboxylate carrier or dicarboxylate carrier.

In certain embodiments the indicator of altered mitochondrial function is a Krebs cycle enzyme, and in certain further embodiments the step of comparing comprises measuring Krebs cycle enzyme catalytic activity. In certain other embodiments the step of measuring comprises determining enzyme activity per mitochondrion in the sample. In another embodiment the step of measuring comprises determining enzyme activity per unit of protein in the sample. In another embodiment the step of comparing comprises measuring Krebs cycle enzyme quantity. In another embodiment the step of measuring comprises determining enzyme quantity per mitochondrion in the sample. In other embodiments the step of measuring comprises determining enzyme quantity per unit of protein in the sample. In other embodiments the Krebs cycle enzyme is citrate synthase, while in other embodiments the Krebs cycle enzyme is aconitase, isocitrate dehydrogenase, alpha-ketoglutarate dehydrogenase, succinyl-coenzyme A synthetase, succinate dehydrogenase, fumarase or malate dehydrogenase.

In some embodiments the indicator of altered mitochondrial function is mitochondrial mass per cell in the sample, which in certain further embodiments is determined using a mitochondria selective agent, in certain other embodiments is determined using nonylacridine orange. In other embodiments, mitochondrial mass is determined by morphometric analysis. In another embodiment, the indicator of altered mitochondrial function is the number of mitochondria per cell in the sample, and in certain further embodiments the step of comparing comprises measuring a mitochondrion selective reagent. In a still further embodiment, the mitochondrion selective reagent is fluorescent. In certain embodiments of the invention, the indicator of altered mitochondrial function is a co-predictor of altered mitochondrial function comprising the amount of mitochondrial DNA per cell in the sample and the step of comparing further comprises comparing at least one additional indicator of altered mitochondrial function. In another embodiment the step of comparing comprises measuring mitochondrial DNA by contacting a biological sample containing mitochondrial DNA with an oligonucleotide primer having a nucleotide sequence that is complementary to a sequence present in the mitochondrial DNA, under conditions and for a time sufficient to allow hybridization of the primer to the mitochondrial DNA; and detecting hybridization of the primer to the mitochondrial DNA, and therefrom quantifying the mitochondrial DNA. In certain further embodiments the step of detecting comprises polymerase chain reaction, oligonucleotide primer extension assay, ligase chain reaction, or restriction fragment length polymorphism analysis.

In certain embodiments the step of comparing comprises measuring mitochondrial DNA by contacting a sample containing amplified mitochondrial DNA with an oligonucleotide primer having a nucleotide sequence that is complementary to a sequence present in the amplified mitochondrial DNA, under conditions and for a time sufficient to allow hybridization of the primer to the mitochondrial DNA; and detecting hybridization of the primer to the mitochondrial DNA, and therefrom quantifying the mitochondrial DNA. In another embodiment the step of detecting comprises polymerase chain reaction, oligonucleotide primer extension assay, ligase chain reaction, or restriction fragment length polymorphism analysis. In another embodiment the mitochondrial DNA is amplified using polymerase chain reaction, transcriptional amplification systems or self-sustained sequence replication. In another embodiment the step of comparing comprises measuring mitochondrial DNA by contacting a biological sample containing mitochondrial DNA with an oligonucleotide primer having a nucleotide sequence that is complementary to a sequence present in the mitochondrial DNA, under conditions and for a time sufficient to allow hybridization of the primer to the mitochondrial DNA; and detecting hybridization and extension of the primer to the mitochondrial DNA to produce a product, and therefrom quantifying the mitochondrial DNA.

In another embodiment the step of comparing comprises measuring mitochondrial DNA by contacting a sample containing amplified mitochondrial DNA with an oligonucleotide primer having a nucleotide sequence that is complementary to a sequence present in the amplified mitochondrial DNA, under conditions and for a time sufficient to allow hybridization of the primer to the mitochondrial DNA; and detecting hybridization and extension of the primer to the mitochondrial DNA to produce a product, and therefrom quantifying the mitochondrial DNA. In a further embodiment the mitochondrial DNA is amplified using polymerase chain reaction, transcriptional amplification systems or self-sustained sequence replication. In another embodiment the amount of mitochondrial DNA in the sample is determined using an oligonucleotide primer extension assay.

Turning to certain other embodiments of the invention, the indicator of altered mitochondrial function is free radical production. In other embodiments the indicator of altered mitochondrial function is reactive oxygen species, protein nitrosylation, protein carbonyl modification, DNA oxidation, mtDNA oxidation, protein oxidation, protein carbonyl modification, malondialdehyde adducts of proteins, a glycoxidation product, a lipoxidation product, 8'-OH-guanosine adducts or TBARS. In other embodiments the indicator of altered mitochondrial function is reactive oxygen species, and in other embodiments the indicator of altered mitochondrial function is protein nitrosylation, while in still other embodiments the indicator of altered mitochondrial function is DNA oxidation. In certain embodiments the indicator of altered mitochondrial function is mitochondrial DNA oxidation. In certain other embodiments the indicator of altered mitochondrial function is protein carbonyl modification. In other embodiments, the indicator of altered mitochondrial function is a cellular response to elevated intracellular calcium, and in still other embodiments the indicator of altered mitochondrial function is a cellular response to at least one apoptogen.

In another aspect, the invention provides a method of treating a human patient having an arthritic disorder, comprising administering to the patient an agent that substantially restores to a normal level at least one indicator of altered mitochondrial function. In certain further embodiments the indicator of altered mitochondrial function is a mitochondrial electron transport chain enzyme, a Krebs cycle enzyme, a mitochondrial matrix component, a mitochondrial membrane component or an ATP biosynthesis factor. In a still further embodiment the indicator of altered mitochondrial function is number per cell or mitochondrial mass per cell. In other embodiments the indicator of altered mitochondrial function is an ATP biosynthesis factor. In another embodiment the indicator of altered mitochondrial function is the amount of ATP per mitochondrion, the amount of ATP per unit mitochondrial mass, the amount of ATP per unit protein or the amount of ATP per unit mitochondrial protein. In some embodiments the indicator of altered mitochondrial function comprises free radical production, and in some embodiments the indicator of altered mitochondrial function comprises a cellular response to elevated intracellular calcium. In other embodiments the at least one indicator of altered mitochondrial function is a co-predictor of altered mitochondrial function, which in certain further embodiments is an amount of mitochondrial DNA per cell in the patient.

It is another aspect of the invention to provide a method of treating an arthritic disorder, comprising administering an effective amount of a mitochondrial function-altering agent. In certain embodiments the agent is a mitochondria protective agent, and in certain other embodiments the agent is an antioxidant.

The invention also provides, in another aspect, a kit for identifying a risk for, determining a degree of disease progression of, or stratifying subjects of a vertebrate species according to subtypes of, an arthritic disorder in a biological sample from a vertebrate subject, comprising at least one reagent capable of detecting a level of at least one indicator of altered mitochondrial function according to the method of any one of claim 1, 2, 6 or 7; and ancillary reagents suitable for use in detecting the indicator.

It is yet another aspect of the invention to provide a method of preparing a synthetic cartilage patch, comprising introducing heterologous mitochondrial DNA into chondrocytes from a first subject having an arthritic disorder to generate cybrid chondrocytes, wherein the exogenous mitochondrial DNA is from a second subject known not to have an arthritic disorder; and culturing the cybrid chondrocytes under conditions and for a time sufficient to permit the chondrocytes to elaborate extracellular matrix.

In still another aspect the invention provides a method of preparing a synthetic cartilage patch, comprising culturing chondrocytes from a subject having an arthritic disorder in the presence of at least one mitochondria protective agent under conditions and for a time sufficient to permit the chondrocytes to elaborate extracellular matrix. In certain embodiments the chondrocytes are cultured in the presence of at least one mitochondria protective agent that is an antioxidant.

In another aspect the invention provides a method of preparing a synthetic cartilage patch, comprising selecting a subpopulation of chondrocytes having enhanced mitochondrial function from an unselected population of chondrocytes derived from a subject having an arthritic disorder; and culturing the subpopulation of chondrocytes under conditions and for a time sufficient to permit the chondrocytes to elaborate extracellular matrix. In certain embodiments the invention provides a synthetic cartilage patch produced by any one of the just-described methods. In certain other embodiments, the invention provides a method of repairing a cartilage defect at a predetermined site in a subject comprising surgically implanting the just-descirbed synthetic cartilage patch at the predetermined site. In certain embodiments the invention further comprises administering one or more mitochondria protective agents to the subject. In certain other embodiments, the one or more mitochondria protective agents comprises at least one antioxidant.

These and other aspects of the present invention will become evident upon reference to the following detailed description and attached drawings. In addition, various references are set forth herein which describe in more detail certain aspects of this invention, and are therefore incorporated by reference in their entireties.

DETAILED DESCRIPTION OF THE INVENTION

Figure 1A:
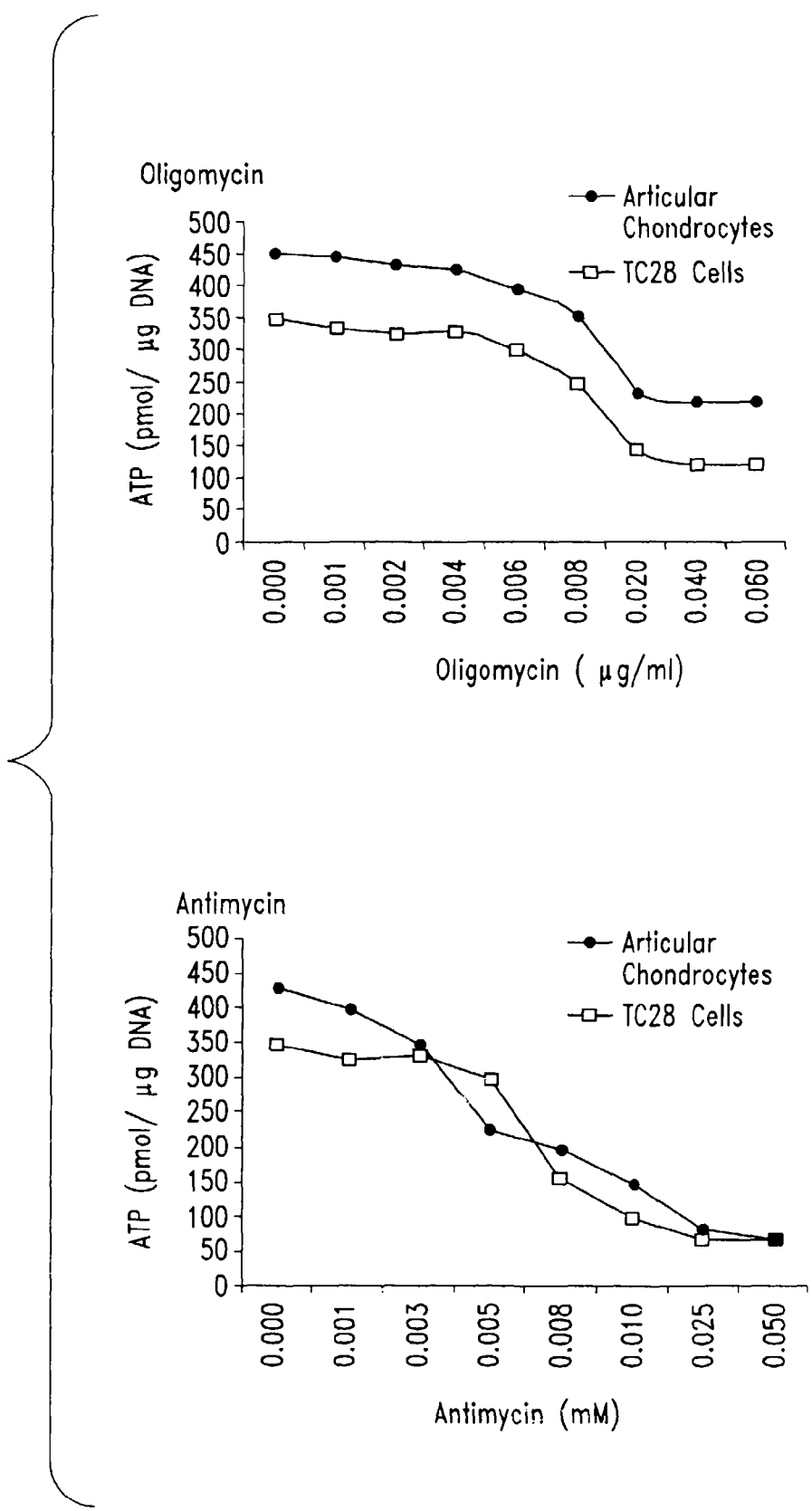
FIGS. 1A and 1B show dose-dependent effects of antimycin and oligomycin on articular chondrocyte an TC28 cell viability and intracellular ATP concentration.

The present invention provides compositions and methods that are useful in pre- and post-symptomatic detection of arthritic disorders and in the identification of therapeutics for treating arthritic disorders.

The present invention derives in part from the unexpected observation of mitochondrial oxidative phosphorylation in vertebrate articular chondrocytes, including generation of ATP in articular chondrocytes by aerobic respiration—that is, ATP results from mitochondrial oxidative phosphorylation in articular chondrocytes and not from anaerobic glycolysis in these cells. The invention also pertains in part to the surprising finding that alterations (e.g., increases or decreases) of such mitochondrial respiratory activity, and in particular of mitochondrially generated ATP, play a significant role in the pathogenesis of arthritic disorders. As noted above, in view of the avascular nature of the articular cartilage milieu in which articular chondrocytes are situated, these cells appear to have adapted by employing anaerobic respiration to biosynthesize and articular chondrocyte mitochondrial roles in arthritic disorders have heretofore been largely ignored. As disclosed herein, indicators of altered mitochondrial function are useful in diagnostic assays to identify a risk for having an arthritic disorder or the degree of disease progression in a subject. As also disclosed herein, indicators of altered mitochondrial function are useful in screening assays for agents suitable for treating an arthritic disorder, for stratifying arthritic patient populations and for monitoring the efficacy of therapeutic treatments. The invention also relates to mitochondria protecting agents that may be useful for treating arthritic disorders, as disclosed herein.

The methods of the present invention pertain in part to the correlation of arthritic disorders with an increased or decreased level of at least one indicator of altered mitochondrial function. In particular, according to the present invention, an "indicator of altered mitochondrial function" may be any detectable parameter that directly relates to a condition, process, pathway, dynamic structure, state or other activity involving mitochondria and that permits detection of altered mitochondrial function in a biological sample from a subject or biological source. The methods of the present invention thus pertain in part to such correlation where the indicator of altered mitochondrial function may be, for example, a mitochondrial enzyme, or other criteria as provided herein.

"Altered mitochondrial function" may refer to any condition or state, including those that accompany an arthritic disorder, where any structure or activity that is directly or indirectly related to a mitochondrial function has been changed in a statistically significant manner relative to a control or standard. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Additionally, altered mitochondrial function may include altered respiratory, metabolic or other biochemical or biophysical activity in some or all cells of a biological source. As non-limiting examples, markedly impaired ETC activity may be related to altered mitochondrial function, as may be generation of increased ROS or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered mitochondrial function. These and other non-limiting examples of altered mitochondrial function are described in greater detail below.

Without wishing to be bound by theory, altered mitochondrial function characteristic of an arthritic disorder may also be related to loss of mitochondrial membrane electrochemical potential by mechanisms other than free radical oxidation, for example by defects in transmitochondrial membrane shuttles and transporters such as the adenine nucleotide transporter or the malate-aspartate shuttle, by intracellular calcium flux, by defects in ATP biosynthesis, by impaired association with porin of hexokinases or other enzymes or by other events. Such collapse of mitochondrial inner membrane potential may result from direct or indirect effects of mitochondrial genes, gene products or related downstream mediator molecules and/or extramitochondrial genes, gene products or related downstream mediators, or from other known or unknown causes.

In certain embodiments of the present invention, an arthritic disorder may be correlated with an increased or decreased level of at least one "co-indicator of altered mitochondrial function". A co-indicator of altered mitochondrial function refers to an indicator of altered mitochondrial function, as provided herein, that is determined concurrently with at least one additional and distinct enzyme or non-enzyme indicator of altered mitochondrial function. For example, a co-indicator of altered mitochondrial function may refer to an indicator of altered mitochondrial function as provided herein, which is quantified in relation to an additional non-enzyme indicator of altered mitochondrial function. For instance, a co-indicator of altered mitochondrial function may be an enzyme determined on the basis of its level per unit mitochondrial protein in a sample (e.g., mitochondrial protein in the sample may be the additional non-enzyme indicator of altered mitochondrial function), but the invention need not be so limited.

By way of background, functional mitochondria contain gene products encoded by mitochondrial genes situated in mitochondrial DNA (mtDNA) and by extramitochondrial genes (e.g., nuclear genes) not situated in the circular mitochondrial genome. The 16.5 kb mtDNA encodes 22 tRNAs, two ribosomal RNAs (rRNA) and 13 enzymes of the electron transport chain (ETC), the elaborate multi-complex mitochondrial assembly where, for example, respiratory oxidative phosphorylation takes place. The overwhelming majority of mitochondrial structural and functional proteins are encoded by extramitochondrial, and in most cases presumably nuclear, genes. Accordingly, mitochondrial and extramitochondrial genes may interact directly, or indirectly via gene products and their downstream intermediates, including metabolites, catabolites, substrates, precursors, cofactors and the like. Alterations in mitochondrial function, for example impaired electron transport activity, defective oxidative phosphorylation or increased free radical production, may therefore arise as the result of defective mtDNA, defective extramitochondrial DNA, defective mitochondrial or extramitochondrial gene products, defective downstream intermediates or a combination of these and other factors.

In the most highly preferred embodiments of the invention, an enzyme is the indicator of altered mitochondrial function as provided herein. The enzyme may be a mitochondrial enzyme, which may further be an ETC enzyme or a Krebs cycle enzyme. The enzyme may also be an ATP biosynthesis factor, which may include an ETC enzyme and/or a Krebs cycle enzyme, or other enzymes or cellular components related to ATP production as provided herein. A "non-enzyme" refers to an indicator of altered mitochondrial function that is not an enzyme (i.e., that is not a mitochondrial enzyme or an ATP biosynthesis factor as provided herein).

In other highly preferred embodiments, the indicator of altered mitochondrial function is any ATP biosynthesis factor as described below. In other preferred embodiments, the indicator is ATP production. In other preferred embodiments, the indicator of altered mitochondrial function may be mitochondrial mass or mitochondrial number. According to the present invention, mitochondrial DNA content may also be an indicator of altered mitochondrial function. In other preferred embodiments the indicator of altered mitochondrial function may be free radical production, a cellular response to elevated intracellular calcium or a cellular response to an apoptogen.

Indicators of Altered Mitochondrial Function that are Enzymes

Certain aspects of the invention are directed to a method for identifying a risk for an arthritic disorder in a vertebrate subject comprising comparing the level of at least one indicator of altered mitochondrial function in a biological sample with a control sample, wherein the indicator of altered mitochondrial function is an enzyme. As provided herein, in certain most highly preferred embodiments, such an enzyme may be a mitochondrial enzyme or an ATP biosynthesis factor that is an enzyme, for example an ETC enzyme or a Krebs cycle enzyme.

Reference herein to "enzyme quantity", "enzyme catalytic activity" or "enzyme expression level" is meant to include a reference to any of a mitochondrial enzyme quantity, activity or expression level or an ATP biosynthesis factor quantity, activity or expression level; either of which may further include, for example, an ETC enzyme quantity, activity or expression level or a Krebs cycle enzyme quantity, activity or expression level. In the most preferred embodiments of the invention, an enzyme is a natural or recombinant protein or polypeptide that has enzyme catalytic activity as provided herein. Such an enzyme may be, by way of non-limiting examples, an enzyme, a holoenzyme, an enzyme complex, an enzyme subunit, an enzyme fragment, derivative or analog or the like, including a truncated, processed or cleaved enzyme.

A "mitochondrial enzyme" that may be an indicator of altered mitochondrial function as provided herein refers to a mitochondrial molecular component that has enzyme catalytic activity and/or functions as an enzyme cofactor capable of influencing enzyme catalytic activity. As used herein, mitochondria are comprised of "mitochondrial molecular components", which may be a protein, polypeptide, peptide, amino acid, or derivative thereof; a lipid, fatty acid or the like, or derivative thereof; a carbohydrate, saccharide or the like or derivative thereof; a nucleic acid, nucleotide, nucleoside, purine, pyrimidine or related molecule, or derivative thereof, or the like; or any covalently or non-covalently complexed combination of these components, or any other biological molecule that is a stable or transient constituent of a mitochondrion.

A mitochondrial enzyme that may be an indicator of altered mitochondrial function or a co-indicator of altered mitochondrial function as provided herein, or an ATP biosynthesis factor that may be an indicator of altered mitochondrial function as provided herein, may comprise an ETC enzyme, which refers to any mitochondrial molecular component that is a mitochondrial enzyme component of the mitochondrial electron transport chain (ETC) complex associated with the inner mitochondrial membrane and mitochondrial matrix. An ETC enzyme may include any of the multiple ETC subunit polypeptides encoded by mitochondrial and nuclear genes. The ETC is typically described as comprising complex I (NADH:ubiquinone reductase), complex II (succinate dehydrogenase), complex III (ubiquinone: cytochrome c oxidoreductase), complex IV (cytochrome c oxidase) and complex V (mitochondrial ATP synthetase), where each complex includes multiple polypeptides and cofactors (for review see, e.g., Walker et al., 1995 *Meths. Enzymol.* 260:14; Emster et al., 1981 *J. Cell Biol.* 91:227s–255s, and references cited therein).

In certain preferred embodiments of the invention it may be useful, for purposes of determining a level of an indicator of altered mitochondrial function that is an enzyme as provided herein, to inhibit the activity of one or more such enzymes (e.g., mitochondrial enzymes) using inhibitors of mitochondrial function as provided herein, for example, mitochondrial enzyme inhibitors, that are known in the art. In certain particularly preferred embodiments, an inhibitor of mitochondrial function is employed using conditions that detectably impair at least one mitochondrial function but that do not detectably decrease glycolysis. For example, under such conditions aerobic respiration (e.g., oxidative phosphorylation) is impaired while anaerobic respiration proceeds. Those having ordinary skill in the art will be able to determine appropriate doses, conditions and samples (e.g., isolated mitochondria, whole or permeabilized cells) for the use of such inhibitors according to methodologies well known in the art and based on the present disclosure.

Inhibitors of mitochondrial function include, but are not limited to, ETC inhibitors, including inhibitors of complex I, for example, 1-methyl-4-phenyl-1,2,3,6-tetrahydropyridine (MPTP), 1-methyl-4-phenylpyridinium (MPP$^+$), amobarbital, rotenoids such as rotenone and deguelin; piericidins such as piericidin A, piericidin B, hydroxypyridine and ubicidin-3; annonaceous acetogenins such as Rolliniastatin-1 and -2; vanilloids such as capsaicin; phenoxan; annonin VI; (for a review, see, e.g., Esposti et al., *Biochim. Biophys. Acta* 1364:222–235, 1998); inhibitors of complex II, for example, thenoyltrifluoroacetone (TTFA), malonate and 3-nitropropionic acid); inhibitors of complex III, for example, antimycin A, stigmatellin A, undecylhydroxydoxobenzothiazole (UHDBT), heptadecylmercaptohydroxyquinoline quinone (HMHQQ), funiculosin and myxothiazol; inhibitors of complex IV, for example, sodium azide, nitric oxide, cyanide and carbon monoxide; inhibitors of lactate dehydrogenase (e.g., oxamic acid); inhibitors of the mitochondrial calcium uniporter (e.g., ruthenium red and Ru360, Matlib et al., *J. Biol. Chem.* 273:10223–10231, 1998), and agents that increase intracellular calcium ion (Ca$^2$) levels, for example, ionophores such as ionomycin, 1-(4,5-dimethoxy-2-nitrophenyl)ethyl ester (also known as calcimycin or A23187), 4-bromo A-23187 and Eth129, and agents that stimulate the release of intracellular extramitochondrial stores of calcium (e.g., thapsigargin and okadaic acid); inhibitors of oxidative phosphorylation (e.g., oligomycin, tributyltin chloride, aurovertin, rutamycin, venturicidin, mercurials, dicyclohexylcarbdiimide also known as DCCD, and Dio-9); respiratory uncouplers (e.g., 2,4-dintrophenol (DNP), p-trifluoromethoxyphenyl hydrazone (FCCP), and carbonyl cyanide m-chlorophenylhydrazone (m-CCCP or CCCP); inhibitors of mitochondrial transport mechanisms, such as inhibitors of mitochondrial adenine nucleotide translocator (ANT) proteins (e.g., atractyloside, carboxyatractyloside, bongkrekic acid); inhibitors of dicarboxylate carriers (which exchange L-malate, succinate, malonate or oxalacetate for inorganic phosphate and are inhibited by, e.g., n-butylmalonate or phenylsuccinate); inhibitors of tricarboxylate carriers (which transport citrate, isocitrate, malate, and phosphoenolpyruvate and are inhibited by, e.g., n-ethylcitrate); inhibitors of mitochondrial protein synthesis (e.g., chloramphenicol); and inhibitors of mitochondrial DNA replication and/or maintenance (e.g., ethidium bromide, or any of various antiviral agents (including, e.g., ddC, ddI, AZT, and others, see, e.g., copending U.S. patent application Ser. Nos. 09/069,489 and 09/301,517.

In certain preferred embodiments described in greater detail below and that relate to manipulations of chondrocytes, a population of unselected chondrocytes may be treated with agents and/or subjected to conditions that positively select for a chondrocyte subpopulation comprising cells having enhanced mitochondrial function, or alternatively, an unselected chondrocyte population may be exposed to conditions that negatively select against cells that have relatively poor mitochondrial function, in order to isolate a subpopulation of chondrocytes having enhanced mitochondrial function. For example, the collection of chondrocytes that is derived from a subject or biological source as provided herein (e.g., a patient having an arthritic disorder) may be treated with sublethal doses of inhibitors of mitochondrial function, as also provided herein. Such cells are concomitantly or subsequently exposed to conditions in which cells need normal to high levels of mitochondrial function in order to survive. For example, cell culture media lacking pyruvate and uridine may be used to select for aerobically competent cells, as cells deficient in mitochondrial function (e.g., rho-zero cells) will die under these conditions (Miller et al., *J. Neurochem.* 67:1897–1907, 1996). As another example, because mitochondrial oxidation produces 18-fold as much ATP per glucose molecule as anaerobic fermentation, competitive inhibitors of ATP (e.g., ddATP, a chain-terminating nucleotide) may be used to select for cells producing relatively high levels of ATP, a subpopulation that extensively overlaps the population of cells having enhanced mitochondrial function.

Although all or most of the cells might survive such conditions in the absence of inhibitors of mitochondrial function, only those having enhanced mitochondrial function will persist in the presence of such inhibitors when such function is necessary for cell survival. That is, cells having normal or substandard mitochondrial function will have even less mitochondrial function during and after treatment with one or more inhibitors of mitochondrial function, and will thus not survive a selection that mandates enhanced mitochondrial function. The cells that do survive such selection procedures are expected to have enhanced levels of one or more mitochondrial functions, and this is confirmed using one or more of the methods of screening cells for mitochondrial function known in the art or herein described.

A mitochondrial enzyme that may be an indicator of altered mitochondrial function as provided herein, or an ATP biosynthesis factor that may be an indicator of altered mitochondrial function as provided herein, may also comprise a Krebs cycle enzyme, which includes mitochondrial molecular components that mediate the series of biochemical/bioenergetic reactions also known as the citric acid cycle or the tricarboxylic acid cycle (see, e.g., Lehninger, Biochemistry, 1975 Worth Publishers, NY; Voet and Voet, Biochemistry, 1990 John Wiley & Sons, NY; Mathews and van Holde, Biochemistry, 1990 Benjamin Cummings, Menlo Park, Calif.). Krebs cycle enzymes include subunits and cofactors of citrate synthase, aconitase, isocitrate dehydrogenase, the α-ketoglutarate dehydrogenase complex, succinyl CoA synthetase, succinate dehydrogenase, fumarase and malate dehydrogenase. Krebs cycle enzymes further include enzymes and cofactors that are functionally linked to the reactions of the Krebs cycle, such as, for example, nicotinamide adenine dinucleotide, coenzyme A, thiamine pyrophosphate, lipoamide, guanosine diphosphate, flavin adenine dinucloetide and nucleoside diphosphokinase.

The methods of the present invention also pertain in part to the correlation of an arthritic disorder with an indicator of altered mitochondrial function that may be an ATP biosynthesis factor, an altered amount of ATP or an altered amount of ATP production. For example, decreased mitochondrial ATP biosynthesis may be an indicator of altered mitochondrial function from which a risk for an arthritic disorder may be identified.

An "ATP biosynthesis factor" refers to any naturally occurring cellular component that contributes to the efficiency of ATP production in mitochondria. Such a cellular component may be a protein, polypeptide, peptide, amino acid, or derivative thereof, a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like. An ATP biosynthesis factor includes at least the components of the ETC and of the Krebs cycle (see, e.g., Lehninger, Biochemistry, 1975 Worth Publishers, NY; Voet and Voet, Biochemistry, 1990 John Wiley & Sons, NY; Mathews and van Holde, Biochemistry, 1990 Benjamin Cummings, Menlo Park, Calif.) and any protein, enzyme or other cellular component that participates in ATP synthesis, regardless of whether such ATP biosynthesis factor is the product of a nuclear gene or of an extranuclear gene (e.g., a mitochondrial gene). Participation in ATP synthesis may include, but need not be limited to, catalysis of any reaction related to ATP synthesis, transmembrane import and/or export of ATP or of an enzyme cofactor, transcription of a gene encoding a mitochondrial enzyme and/or translation of such a gene transcript.

Compositions and methods for determining whether a cellular component is an ATP biosynthesis factor are well known in the art, and include methods for determining ATP production (including determination of the rate of ATP production in a sample) and methods for quantifying ATP itself. The contribution of an ATP biosynthesis factor to ATP production can be determined, for example, using an isolated ATP biosynthesis factor that is added to cells or to a cell-free system. The ATP biosynthesis factor may directly or indirectly mediate a step or steps in a biosynthetic pathway that influences ATP production. For example, an ATP biosynthesis factor may be an enzyme that catalyzes a particular chemical reaction leading to ATP production. As another example, an ATP biosynthesis factor may be a cofactor that enhances the efficiency of such an enzyme. As another example, an ATP biosynthesis factor may be an exogenous genetic element introduced into a cell or a cell-free system that directly or indirectly affects an ATP biosynthetic pathway. Those having ordinary skill in the art are readily able to compare ATP production by an ATP biosynthetic pathway in the presence and absence of a candidate ATP biosynthesis factor. Routine determination of ATP production may be accomplished using any known method for quantitative ATP detection, for example by way of illustration and not limitation, by differential extraction from a sample optionally including chromatographic isolation; by spectrophotometry; by quantification of labeled ATP recovered from a sample contacted with a suitable form of a detectably labeled ATP precursor molecule such as, for example, $^{32}$P; by quantification of an enzyme activity associated with ATP synthesis or degradation; or by other techniques that are known in the art. Accordingly, in certain embodiments of the present invention, the amount of ATP in a biological sample or the production of ATP (including the rate of ATP production) in a biological sample may be an indicator of altered mitochondrial function. In one embodiment, for instance, ATP may be quantified by measuring luminescence of luciferase catalyzed oxidation of D-luciferin, an ATP dependent process.

In certain preferred embodiments of the invention, ATP production may be expressed as units of ATP per unit total cellular DNA (or per cell) in a sample, and in certain other preferred embodiments, ATP production may be expressed as units of ATP produced per unit time (e.g., rate) per unit total cellular DNA (or per cell) in a sample. In certain other embodiments, ATP production may be expressed as units of ATP per unit protein in a sample, and in other embodiments as units of ATP produced per unit time (e.g., rate) per unit protein in a sample. In certain other preferred embodiments, ATP production may be expressed as units of ATP generated per unit time (e.g., rate) per unit mitochondrial mass in a sample. In certain other preferred embodiments, ATP production may be expressed as units of ATP generated per unit time (e.g., rate) per unit mitochondrial protein mass in a sample.

"Enzyme catalytic activity" refers to any function performed by a particular enzyme or category of enzymes that is directed to one or more particular cellular function(s). For example, "ATP biosynthesis factor catalytic activity" refers to any function performed by an ATP biosynthesis factor as provided herein that contributes to the production of ATP. Typically, enzyme catalytic activity is manifested as facilitation of a chemical reaction by a particular enzyme, for instance an enzyme that is an ATP biosynthesis factor, wherein at least one enzyme substrate or reactant is covalently modified to form a product. For example, enzyme catalytic activity may result in a substrate or reactant being modified by formation or cleavage of a covalent chemical bond, but the invention need not be so limited. Various methods of measuring enzyme catalytic activity are known to those having ordinary skill in the art and depend on the particular activity to be determined.

For many enzymes, including mitochondrial enzymes or enzymes that are ATP biosynthesis factors as provided herein, quantitative criteria for enzyme catalytic activity are well established. These criteria include, for example, activity that may be defined by international units (IU), by enzyme turnover number, by catalytic rate constant ($K_{cat}$), by Michaelis-Menten constant ($K_m$), by specific activity or by any other enzymological method known in the art for measuring a level of at least one enzyme catalytic activity. Specific activity of a mitochondrial enzyme, such as an ATP biosynthesis factor, may be expressed as units of substrate detectably converted to product per unit time and, optionally, further per unit sample mass (e.g., per unit protein or per unit mitochondrial mass).

In certain preferred embodiments of the invention, enzyme catalytic activity may be expressed as units of substrate detectably converted by an enzyme to a product per unit time per unit total protein in a sample. In certain particularly preferred embodiments, enzyme catalytic activity may be expressed as units of substrate detectably converted by an enzyme to product per unit time per unit mitochondrial mass in a sample. In certain highly preferred embodiments, enzyme catalytic activity may be expressed as units of substrate detectably converted by an enzyme to product per unit time per unit mitochondrial protein mass in a sample. Products of enzyme catalytic activity may be detected by suitable methods that will depend on the quantity and physicochemical properties of the particular product. Thus, detection may be, for example by way of illustration and not limitation, by radiometric, calorimetric, spectrophotometric, fluorimetric, immunometric or mass spectrometric procedures, or by other suitable means that will be readily apparent to a person having ordinary skill in the art.

In certain embodiments of the invention, detection of a product of enzyme catalytic activity may be accomplished directly, and in certain other embodiments detection of a product may be accomplished by introduction of a detectable reporter moiety or label into a substrate or reactant such as a marker enzyme, dye, radionuclide, luminescent group, fluorescent group or biotin, or the like. The amount of such a label that is present as unreacted substrate and/or as reaction product, following a reaction to assay enzyme catalytic activity, is then determined using a method appropriate for the specific detectable reporter moiety or label. For radioactive groups, radionuclide decay monitoring, scintillation counting, scintillation proximity assays (SPA) or autoradiographic methods are generally appropriate. For immunometric measurements, suitably labeled antibodies may be prepared including, for example, those labeled with radionuclides, with fluorophores, with affinity tags, with biotin or biotin mimetic sequences or those prepared as antibody enzyme conjugates (see, e.g., Weir, D. M., *Handbook of Experimental Immunology*, 1986, Blackwell Scientific, Boston; Scouten, W. H., *Methods in Enzymology* 135: 30–65, 1987; Harlow and Lane, *Antibodies: A Laboratory Manual, Cold Spring Harbor Laboratory*, 1988; Haugland, 1996 *Handbook of Fluorescent Probes and Research Chemicals—Sixth Ed.*, Molecular Probes, Eugene, Oreg.; Scopes, R. K., *Protein Purification: Principles and Practice*, 1987, Springer-Verlag, NY; Hermanson, G. T. et al., *Immobilized Affinity Ligand Techniques*, 1992, Academic Press, Inc., NY; Luo et al., 1998 *J. Biotechnol.* 65:225 and references cited therein). Spectroscopic methods may be used to detect dyes (including, for example, colorimetric products of enzyme reactions), luminescent groups and fluorescent groups. Biotin may be detected using avidin or streptavidin, coupled to a different reporter group (commonly a radioactive or fluorescent group or an enzyme). Enzyme reporter groups may generally be detected by the addition of substrate (generally for a specific period of time), followed by spectroscopic, spectrophotometric or other analysis of the reaction products. Standards and standard additions may be used to determine the level of enzyme catalytic activity in a sample, using well known techniques.

As noted above, enzyme catalytic activity of an ATP biosynthesis factor may further include other functional activities that lead to ATP production, beyond those involving covalent alteration of a substrate or reactant. For example by way of illustration and not limitation, an ATP biosynthesis factor that is an enzyme may refer to a transmembrane transporter molecule that, through its enzyme catalytic activity, facilitates the movement of metabolites between cellular compartments. Such metabolites may be ATP or other cellular components involved in ATP synthesis, such as gene products and their downstream intermediates, including metabolites, catabolites, substrates, precursors, cofactors and the like. As another non-limiting example, an ATP biosynthesis factor that is an enzyme may, through its enzyme catalytic activity, transiently bind to a cellular component involved in ATP synthesis in a manner that promotes ATP synthesis. Such a binding event may, for instance, deliver the cellular component to another enzyme involved in ATP synthesis and/or may alter the conformation of the cellular component in a manner that promotes ATP synthesis. Further to this example, such conformational alteration may be part of a signal transduction pathway, an allosteric activation pathway, a transcriptional activation pathway or the like, where an interaction between cellular components leads to ATP production.

Thus, according to the present invention, an ATP biosynthesis factor may include, for example, a mitochondrial membrane protein. Suitable mitochondrial membrane proteins include such mitochondrial components as the adenine nucleotide transporter (ANT; e.g., Fiore et al., 1998 *Biochimie* 80:137; Klingenberg 1985 *Ann. N.Y Acad. Sci.* 456: 279), the voltage dependent anion channel (VDAC, also referred to as porin; e.g., Manella, 1997 *J. Bioenergetics Biomembr.* 29:525), the malate-aspartate shuttle, the mitochondrial calcium uniporter (e.g., Litsky et al., 1997 *Biochem.* 36:7071), uncoupling proteins (UCP-1, -2, -3; see e.g., Jezek et al., 1998 *Int. J. Biochem. Cell Biol.* 30:1163), a hexokinase, a peripheral benzodiazepine receptor, a mitochondrial intermembrane creatine kinase, cyclophilin D, a Bcl-2 gene family encoded polypeptide, the tricarboxylate carrier (e.g., Iocobazzi et al., 1996 *Biochim. Biophys. Acta* 1284:9; Bisaccia et al., 1990 *Biochim. Biophys. Acta* 1019: 250) and the dicarboxylate carrier (e.g., Fiermonte et al., 1998 *J. Biol. Chem.* 273:24754; Indiveri et al., 1993 *Biochim. Biophys. Acta* 1143:310; for a general review of mitochondrial membrane transporters, see, e.g., Zonatti et al., 1994 *J. Bioenergetics Biomembr.* 26:543 and references cited therein).

"Enzyme quantity" as used herein refers to an amount of an enzyme including mitochondrial enzymes or enzymes that are ATP biosynthesis factors as provided herein, or of another ATP biosynthesis factor, that is present, i.e., the physical presence of an enzyme or ATP biosynthesis factor selected as an indicator of altered mitochondrial function, irrespective of enzyme catalytic activity. Depending on the physicochemical properties of a particular enzyme or ATP biosynthesis factor, the preferred method for determining the enzyme quantity will vary. In the most highly preferred embodiments of the invention, determination of enzyme quantity will involve quantitative determination of the level of a protein or polypeptide using routine methods in protein chemistry with which those having skill in the art will be readily familiar, for example by way of illustration and not limitation, those described in greater detail below.

Accordingly, determination of enzyme quantity may be by any suitable method known in the art for quantifying a particular cellular component that is an enzyme or an ATP biosynthesis factor as provided herein, and that in preferred embodiments is a protein or polypeptide. Depending on the nature and physicochemical properties of the enzyme or ATP biosynthesis factor, determination of enzyme quantity may be by densitometric, mass spectrometric, spectrophotometric, fluorimetric, immunometric, chromatographic, electrochemical or any other means of quantitatively detecting a particular cellular component. Methods for determining enzyme quantity also include methods described above that are useful for detecting products of enzyme catalytic activity, including those measuring enzyme quantity directly and those measuring a detectable label or reporter moiety. In certain preferred embodiments of the invention, enzyme quantity is determined by immunometric measurement of an isolated enzyme or ATP biosynthesis factor. In certain preferred embodiments of the invention, these and other immunological and immunochemical techniques for quantitative determination of biomolecules such as an enzyme or ATP biosynthesis factor may be employed using a variety of assay formats known to those of ordinary skill in the art, including but not limited to enzyme linked immunosorbent assay (ELISA), radioimmunoassay (RIA), immunofluorimetry, immunoprecipitation, equilibrium dialysis, immunodiffusion and other techniques. (See, e.g., Harlow and Lane, *Antibodies: A Laboratory Manual*, Cold Spring Harbor Laboratory, 1988; Weir, D. M., *Handbook of Experimental Immunology*, 1986, Blackwell Scientific, Boston.) For example, the assay may be performed in a Western blot format, wherein a preparation comprising proteins from a biological sample is submitted to gel electrophoresis, transferred to a suitable membrane and allowed to react with an antibody specific for an enzyme or an ATP biosynthesis factor that is a protein or polypeptide. The presence of the antibody on the membrane may then be detected using a suitable detection reagent, as is well known in the art and described above.

In certain embodiments of the invention, an indicator of altered mitochondrial function including, for example, an enzyme as provided herein, may be present in isolated form. The term "isolated" means that a material is removed from its original environment (e.g., the natural environment if it is naturally occurring). For example, a naturally occurring polypeptide present in a living animal is not isolated, but the same polypeptide, separated from some or all of the co-existing materials in the natural system, is isolated. Such polypeptides could be part of a composition, and still be isolated in that such composition is not part of its natural environment.

Affinity techniques are particularly useful in the context of isolating an enzyme or an ATP biosynthesis factor protein or polypeptide for use according to the methods of the present invention, and may include any method that exploits a specific binding interaction involving an enzyme or an ATP biosynthesis factor to effect a separation. For example, because an enzyme or an ATP biosynthesis factor protein or polypeptide may contain covalently attached oligosaccharide moieties, an affinity technique such as binding of the enzyme (or ATP biosynthesis factor) to a suitable immobilized lectin under conditions that permit carbohydrate binding by the lectin may be a particularly useful affinity technique.

Other useful affinity techniques include immunological techniques for isolating and/or detecting a specific protein or polypeptide antigen (e.g., an enzyme or ATP biosynthesis factor), which techniques rely on specific binding interaction between antibody combining sites for antigen and antigenic determinants present on the factor. Binding of an antibody or other affinity reagent to an antigen is "specific" where the binding interaction involves a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of binding partners or antibodies can be readily determined using conventional techniques, for example those described by Scatchard et al., *Ann. N.Y. Acad. Sci.* 51:660 (1949).

Immunological techniques include, but need not be limited to, immunoaffinity chromatography, immunoprecipitation, solid phase immunoadsorption or other immunoaffinity methods. For these and other useful affinity techniques, see, for example, Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques.

As noted above, an indicator of altered mitochondrial function can be a protein or polypeptide, for example an enzyme or an ATP biosynthesis factor. The protein or polypeptide may be an unmodified polypeptide or may be a polypeptide that has been posttranslationally modified, for example by glycosylation, phosphorylation, fatty acylation including glycosylphosphatidylinositol anchor modification or the like, phospholipase cleavage such as phosphatidylinositol-specific phospholipase c mediated hydrolysis or the like, protease cleavage, dephosphorylation or any other type of protein posttranslational modification such as a modification involving formation or cleavage of a covalent chemical bond.

Indicators of Altered Mitochondrial Function that are Mitochondrial Mass, Mitochondrial Volume or Mitochondrial Number According to certain embodiments, the invention is directed to a method for identifying a risk for an arthritic disorder in a vertebrate subject comprising comparing the level of at least one indicator of altered mitochondrial function in a biological sample with a control sample, wherein the indicator of altered mitochondrial function is at least one of mitochondrial mass, mitochondrial volume or mitochondrial number.

Methods for quantifying mitochondrial mass, volume and/or mitochondrial number are known in the art, and may include, for example, quantitative staining of a representative biological sample. Typically, quantitative staining of mitochondria may be performed using organelle-selective probes or dyes, including but not limited to mitochondrion selective reagents such as fluorescent dyes that bind to mitochondrial molecular components (e.g., nonylacridine orange, MitoTrackers™, Molecular Probes, Inc., Eugene, Oreg.) or potentiometric dyes that accumulate in mitochondria as a function of mitochondrial inner membrane electrochemical potential (see, e.g., Haugland, 1996 *Handbook of Fluorescent Probes and Research Chemicals—Sixth Ed.*, Molecular Probes, Eugene, Oreg.). As another example, mitochondrial mass, volume and/or number may be quantified by morphometric analysis (e.g., Cruz-Orive et al., 1990 *Am. J. Physiol.* 258:L148; Schwerzmann et al., 1986 *J. Cell Biol.* 102:97). These or any other means known in the art for quantifying mitochondrial mass, volume and/or mitochondrial number in a sample are within the contemplated scope of the invention. For example, the use of such quantitative determinations for purposes of calculating mitochondrial density is contemplated and is not intended to be limiting. In certain highly preferred embodiments, mitochondrial protein mass in a sample is determined using well known procedures. For example, a person having ordinary skill in the art can readily prepare an isolated mitochondrial fraction from a biological sample using established cell fractionation techniques, and therefrom determine protein content using any of a number of protein quantification methodologies well known in the art.

Co-Predictors of Altered Mitochondrial Function that Include Mitochondrial DNA Content According to certain other particular embodiments, the invention contemplates a "co-predictor" of altered mitochondrial function, which refers to an indicator of altered mitochondrial function, as provided herein, that is determined concurrently with at least one additional and distinct indicator of altered mitochondrial function, which may be an indicator of altered mitochondrial function as described above. In preferred embodiments, a co-predictor of altered mitochondrial function may be mitochondrial DNA content in a biological sample, and in particularly preferred embodiments the co-predictor of altered mitochondrial function comprises the amount of mitochondrial DNA per cell (or per unit total cellular DNA) in the sample, and in other particularly preferred embodiments the co-predictor of altered mitochondrial function comprises the amount of mitochondrial DNA per mitochondrion in the sample. Thus, quantification of mitochondrial DNA may not be an indicator of altered mitochondrial function according to the present invention, but quantification of mitochondrial DNA may be a co-predictor of altered mitochondrial function, as provided herein.

Quantification of mitochondrial DNA (mtDNA) content may be accomplished by any of a variety of established techniques that are useful for this purpose, including but not limited to oligonucleotide probe hybridization or polymerase chain reaction (PCR) using oligonucleotide primers specific for mitochondrial DNA sequences (see, e.g., Miller et al., 1996 *J. Neurochem.* 67:1897; Fahy et al., 1997 *Nucl. Ac. Res.* 25:3102; U.S. patent application Ser. No. 09/098, 079; Lee et al., 1998 *Diabetes Res. Clin. Practice* 42:161; Lee et al., 1997 *Diabetes* 46(suppl. 1): 175A). A particularly useful method is the primer extension assay disclosed by Fahy et al. (*Nucl. Acids Res.* 25:3102, 1997) and by Ghosh et al. (*Am. J. Hum. Genet.* 58:325, 1996). Suitable hybridization conditions may be found in the cited references or may be varied according to the particular nucleic acid target and oligonucleotide probe selected, using methodologies well known to those having ordinary skill in the art (see, e.g., Ausubel et al., *Current Protocols in Molecular Biology*, Greene Publishing, 1987; Sambrook et al., *Molecular Cloning: A Laboratory Manual*, Cold Spring Harbor Press, 1989).

Examples of other useful techniques for determining the amount of specific nucleic acid target sequences (e.g., mtDNA) present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems (e.g., Kwoh et al., 1989 *Proc. Nat. Acad. Sci.* 86:1173); strand displacement amplification (e.g., Walker et al., *Nucl. Ac. Res.* 20:1691, 1992; Walker et al., *Proc. Nat. Acad. Sci.* 89:392, 1992) and self-sustained sequence replication (3SR, see, e.g., Ghosh et al, in Molecular Methods for Virus Detection, 1995 Academic Press, NY, pp. 287–314; Guatelli et al., *Proc. Nat. Acad. Sci.* 87:1874, 1990), the cited references for which are incorporated herein by reference in their entireties. Other useful amplification techniques include, for example, ligase chain reaction (e.g., Barany, *Proc. Nat. Acad. Sci.* 88:189, 1991), Q-beta replicase assay (Cahill et al., *Clin. Chem.* 37:1482, 1991; Lizardi et al., *Biotechnol.* 6:1197, 1988; Fox et al., *J. Clin. Lab. Analysis* 3:378, 1989) and cycled probe technology (e.g., Cloney et al., *Clin. Chem.* 40:656, 1994), as well as other suitable methods that will be known to those familiar with the art.

Sequence length or molecular mass of primer extension assay products may be determined using any known method for characterizing the size of nucleic acid sequences with which those skilled in the art are familiar. In a preferred embodiment, primer extension products are characterized by gel electrophoresis. In another embodiment, primer extension products are characterized by mass spectrometry (MS), which may further include matrix assisted laser desorption ionization/time of flight (MALDI-TOF) analysis or other MS techniques known to those skilled in the art. See, for example, U.S. Pat. Nos. 5,622,824, 5,605,798 and 5,547, 835. In another embodiment, primer extension products are characterized by liquid or gas chromatography, which may further include high performance liquid chromatography (HPLC), gas chromatography-mass spectrometry (GC-MS) or other well known chromatographic methodologies.

Accordingly, contemplated indicators or co-predictors of altered mitochondrial function that relate to mitochondrial mass, mitochondrial number, mitochondrial volume and mitochondrial DNA content may also include, but need not be limited to, determination of mitochondrial replication, mitochondrial transcription and translation; and the like.

Indicators of Altered Mitochondrial Function that are Cellular Responses to Elevated Intracellular Calcium or Altered Mitochondrial Membrane Potential Certain aspects of the present invention, as it relates to the correlation of an arthritic disorder with an indicator of altered mitochondrial function, involve monitoring intracellular calcium homeostasis and/or cellular responses to perturbations of this homeostasis, including physiological and pathophysiological calcium regulation. In particular, according to these aspects, the method of the present invention is directed to identifying a risk for an arthritic disorder in a subject by comparing a cellular response to elevated intracellular calcium in a biological sample from the subject with that of a control subject. The range of cellular responses to elevated intracellular calcium is broad, as is the range of methods and reagents for the detection of such responses. Many specific cellular responses are known to those having ordinary skill in the art; these responses will depend on the particular cell types present in a selected biological sample. It is within the contemplation of the present invention to provide a method for identifying a risk for an arthritic disorder by comparing a cellular response to elevated intracellular calcium, where such response is an indicator of altered mitochondrial function as provided herein. As non-limiting examples, cellular responses to elevated intracellular calcium include secretion of specific secretory products, exocytosis of particular pre-formed components, increased glycogen metabolism and cell proliferation (see, e.g., Clapham, 1995 *Cell* 80:259; Cooper, *The Cell—A Molecular Approach*, 1997 ASM Press, Washington, D.C.; Alberts, B., Bray, D., et al., *Molecular Biology of the Cell*, 1995 Garland Publishing, NY).

As a brief background, normal alterations of intramitochondrial $Ca^{2+}$ are associated with normal metabolic regulation (Dykens, 1998 in *Mitochondria & Free Radicals in Neurodegenerative Diseases*, Beal, Howell and Bodis-Wollner, Eds., Wiley-Liss, New York, pp. 29–55; Radi et al., 1998 in *Mitochondria &Free Radicals in Neurodegenerative Diseases*, Beal, Howell and Bodis-Wollner, Eds., Wiley-Liss, New York, pp. 57–89; Gunter and Pfeiffer, 1991, *Am. J. Physiol.* 27: C755; Gunter et al., 1994, *Am. J. Physiol.* 267: 313). For example, fluctuating levels of mitochondrial free $Ca^{2+}$ may be responsible for regulating oxidative metabolism in response to increased ATP utilization, via allosteric regulation of enzymes (reviewed by Crompton et al., 1993 *Basic Res. Cardiol.* 88: 513–523;) and the glycerophosphate shuttle (Gunter et al., 1994 *J. Bioenerg. Biomembr.* 26: 471).

Normal mitochondrial function includes regulation of cytosolic free calcium levels by sequestration of excess $Ca^{2+}$ within the mitochondrial matrix. Depending on cell type, cytosolic $Ca^{2+}$ concentration is typically 50–100 nM. In normally functioning cells, when $Ca^{2+}$ levels reach 200–300 nM, mitochondria begin to accumulate $Ca^{2+}$ as a function of the equilibrium between influx via a $Ca^{2+}$ uniporter in the inner mitochondrial membrane and $Ca^{2+}$ efflux via both $Na^+$ dependent and $Na^+$ independent calcium carriers. In certain instances, such perturbation of intracellular calcium homeostasis is a feature of diseases (such as an arthritic disorder) associated with altered mitochondrial function, regardless of whether the calcium regulatory dysfunction is causative of, or a consequence of, altered mitochondrial function.

Elevated mitochondrial calcium levels thus may accumulate in response to an initial elevation in cytosolic free calcium, as described above. Such elevated mitochondrial calcium concentrations in combination with reduced ATP or other conditions associated with mitochondrial pathology, can lead to collapse of mitochondrial inner membrane potential (see Gunter et al., 1998 *Biochim. Biophys. Acta* 1366:5; Rottenberg and Marbach, 1990, *Biochim. Biophys. Acta* 1016:87). Generally, in order to practice the subject invention method for identifying a risk for an arthritic disorder in an individual, the extramitochondrial (cytosolic) level of $Ca^{2+}$ in a biological sample is greater than that present within mitochondria. In the case of an arthritic disorder, mitochondrial or cytosolic calcium levels may vary from the above ranges and may range from, e.g., about 1 nM to about 500 mM, more typically from about 10 nM to about 100 µM and usually from about 20 nM to about 1 µM, where "about" indicates ±10%. A variety of calcium indicators are known in the art, including but not limited to, for example, fura-2 (McCormack et al., 1989 *Biochim. Biophys. Acta* 973:420); mag-fura-2; BTC (U.S. Pat. No. 5,501,980); fluo-3, fluo-4 and fluo-5N (U.S. Pat. No. 5,049,673); rhod-2; benzothiaza-1; and benzothiaza-2 (all of which are available from Molecular Probes, Eugene, Oreg.). These or any other means for monitoring intracellular calcium are contemplated according to the subject invention method for identifying a risk for an arthritic disorder.

For monitoring an indicator of altered mitochondrial function that is a cellular response to elevated intracellular calcium, compounds that induce increased cytoplasmic and mitochondrial concentrations of $Ca^{2+}$, including calcium ionophores, are well known to those of ordinary skill in the art, as are methods for measuring intracellular calcium (see, e.g., Gunter and Gunter, 1994 *J. Bioenerg Biomembr.* 26: 471; Gunter et al., 1998 *Biochim. Biophys. Acta* 1366:5; McCormack et al., 1989 *Biochim. Biophys. Acta* 973:420; Orrenius and Nicotera, 1994 *J. Neural. Transm. Suppl.* 43:1; Leist and Nicotera, 1998 *Rev. Physiol. Biochem. Pharmacol.* 132:79; and Haugland, 1996 *Handbook of Fluorescent Probes and Research Chemicals—Sixth Ed.*, Molecular Probes, Eugene, Oreg.). Accordingly, a person skilled in the art may readily select a suitable ionophore (or another compound that results in increased cytoplasmic and/or mitochondrial concentrations of $Ca^{2+}$) and an appropriate means for detecting intracellular calcium for use in the present invention, according to the instant disclosure and to well known methods.

$Ca^{2+}$ influx into mitochondria appears to be largely dependent, and may be completely dependent, upon the negative transmembrane electrochemical potential (ΔT) established at the inner mitochondrial membrane by electron transfer, and such influx fails to occur in the absence of Δψ even when an eight-fold $Ca^{2+}$ concentration gradient is imposed (Kapus et al., 1991 *FEBS Lett.* 282:61). Accordingly, mitochondria may release $Ca^{2+}$ when the membrane potential is dissipated, as occurs with uncouplers like 2,4-dinitrophenol and carbonyl cyanide p-trifluoro-methoxyphenylhydrazone (FCCP). Thus, according to certain embodiments of the present invention, collapse of ΔΨ may be potentiated by influxes of cytosolic free calcium into the mitochondria, as may occur under certain physiological conditions including those encountered by cells of a subject having an arthritic disorder. Detection of such collapse may be accomplished by a variety of means as provided herein.

In certain related embodiments of the invention, altered (e.g., increased or decreased) mitochondrial membrane potential may be an indicator of altered mitochondrial function. Typically, mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes (See, e.g., Emster et al., 1981 *J. Cell Biol.* 91:227s and references cited; see also Haugland, 1996 *Handbook of Fluorescent Probes and Research Chemicals—Sixth Ed., Molecular Probes, Eugene, Oreg., pp.* 266–274 and 589–594.). For example, by way of illustration and not limitation, the fluorescent probes 2-,4-dimethylaminostyryl-N-methylpyridinium (DASPMI) and tetramethylrhodamine esters (such as, e.g., tetramethylrhodamine methyl ester, TMRM; tetramethylrhodamine ethyl ester, TMRE) or related compounds (see, e.g., Haugland, 1996, supra) may be quantified following accumulation in mitochondria, a process that is dependent on, and proportional to, mitochondrial membrane potential (see, e.g., Murphy et al., 1998 in *Mitochondria & Free Radicals in Neurodegenerative Diseases*, Beal, Howell and Bodis-Wollner, Eds., Wiley-Liss, New York, pp. 159–186 and references cited therein; and *Molecular Probes On-line Handbook of Fluorescent Probes and Research Chemicals*, at http://www.probes.com/handbook/toc.html). Other fluorescent detectable compounds that may be used in the invention include but are not limited to rhodamine 123, rhodamine B hexyl ester, $DiOC_6(3)$, JC-1 [5,5',6,6'-Tetrachloro-1,1',3,3'-Tetraethylbezimidazol-carbocyanine Iodide] (see Cossarizza, et al., 1993 *Biochem. Biophys. Res. Comm.* 197:40; Reers et al., 1995 *Meth. Enzymol.* 260:406), rhod-2 (see U.S. Pat. No. 5,049,673; all of the preceding compounds are available from Molecular Probes, Eugene, Oreg.) and rhodamine 800 (Lambda Physik, GmbH, Göttingen, Germany; see Sakanoue et al., 1997 *J. Biochem.* 121:29). Methods for monitoring mitochondrial membrane potential are also disclosed in U.S. application Ser. No. 09/161,172.

Mitochondrial membrane potential can also be measured by non-fluorescent means, for example by using TTP (tetraphenylphosphonium ion) and a TTP-sensitive electrode (Kamo et al., 1979 *J. Membrane Biol.* 49:105; Porter and Brand, 1995 Am. J. Physiol. 269:R1213). Those skilled in the art will be able to select appropriate detectable compounds or other appropriate means for measuring $\Delta\Psi m$. By way of example and not limitation, TMRM is somewhat preferable to TMRE because, following efflux from mitochondria, TMRE yields slightly more residual signal in the endoplasmic reticulicum and cytoplasm than TMRM.

As another non-limiting example, membrane potential may be additionally or alternatively calculated from indirect measurements of mitochondrial permeability to detectable charged solutes, using matrix volume and/or pyridine nucleotide redox determination combined with spectrophotometric or fluorimetric quantification. Measurement of membrane potential dependent substrate exchange-diffusion across the inner mitochondrial membrane may also provide an indirect measurement of membrane potential. (See, e.g., Quinn, 1976, *The Molecular Biology of Cell Membranes*, University Park Press, Baltimore, Md., pp. 200–217 and references cited therein.)

Exquisite sensitivity to extraordinary mitochondrial accumulations of $Ca^{2+}$ that result from elevation of intracellular calcium, as described above, may also characterize an arthritic disorder. Such mitochondrial sensitivity may provide an indicator of altered mitochondrial function according to the present invention. Additionally, a variety of physiologically pertinent agents, including hydroperoxide and free radicals, may synergize with $Ca^{2+}$ to induce collapse of $\Delta\Psi$ (Novgorodov et al., 1991 *Biochem. Biophys. Acta* 1058: 242; Takeyama et al., 1993 *Biochem. J.* 294: 719; Guidox et al., 1993 *Arch. Biochem. Biophys.* 306:139). Accordingly, non-limiting examples of indicators of altered mitochondrial function that are cellular responses to elevated intracellular calcium or altered mitochondrial membrane potential include mitochondrial membrane potential ($\Delta\psi_m$) assays (described in copending U.S. patent application Ser. No. 60/140,433) and mitochondrial permeability transition (MPT) assays (described in copending U.S. patent application Ser. No. 09/161,172).

Indicators of Altered Mitochondrial Function that are Cellular Responses to Apoptogenic Stimuli Turning to another aspect, the present invention relates to the correlation of an arthritic disorder with an indicator of altered mitochondrial function, involving programmed cell death or apoptosis. In particular, according to this aspect, the present invention is directed to a method comprising comparing a cellular response to an apoptosis-inducing ("apoptogenic") stimulus in a biological sample from (i) a subject believed to be at risk for an arthritic disorder, and (ii) a control subject. The range of cellular responses to various known apoptogenic stimuli is broad, as is the range of methods and reagents for the detection of such responses. It is within the contemplation of the present invention to provide a method for identifying a risk for an arthritic disorder by comparing a cellular response to an apoptogenic stimulus, where such response is an indicator of altered mitochondrial function as provided herein.

As noted above, mitochondrial dysfunction and/or related elevated ROS levels may initiate early events leading to apoptosis in various cell types (Kroemer et al., *FASEB J.* 9:1277–87, 1995; Zamzarni et al., *J. Exp. Med.* 182:367–77, 1995; Zamzami et al., *J. Exp. Med.* 181:1661–72, 1995; Ausserer et al., *Mol. Cell. Biol.* 14:5032–42, 1994). In several cell types, reduction in the mitochondrial membrane potential ($\Delta\psi m$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in an arthritic disorder and may further induce pathogenetic events via apoptotic mechanisms.

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al, *Biochim. Biophys. Act.* 1271:63, 1995). Localization of Bcl-2 to this membrane appears to be indispensable for modulation of apoptosis (Nguyen et al., *J. Biol. Chem.* 269:16521–24, 1994). Thus, changes in mitochondrial physiology may be important mediators of apoptosis.

Altered mitochondrial function, as may be used to identify a risk for an arthritic disorder in a subject according to the present disclosure, may therefore lower the threshold for induction of apoptosis by an apoptogen. A variety of apoptogens are known to those familiar with the art (see, e.g., Green et al., 1998 *Science* 281:1309 and references cited therein) and may include by way of illustration and not limitation apoptogens that, when added to cells under appropriate conditions with which those skilled in the art will be familiar, require specific receptors such as the tumor necrosis factor, FasL, glutamate, NMDA, IL-1, IL-3, corticosterone, mineralcorticoid or glucocorticoid receptor(s). Apoptogens may further include herbimycin A (Mancini et al., 1997 *J. Cell. Biol.* 138:449–469); paraquat (Costantini et al., 1995 *Toxicology* 99:1–2); ethylene glycols; protein kinase inhibitors such as, e.g.: staurosporine, calphostin C, caffeic acid phenethyl ester, chelerythrine chloride, genistein; 1-(5-isoquinolinesulfonyl)-2-methylpiperazine; N-[2-((p-bromocinnamyl)amino)ethyl]-5—5-isoquinolinesulfonamide; KN-93; quercitin; d-erythro-sphingosine derivatives; UV radiation; ionophores such as, e.g., ionomycin, valinomycin and other ionophores known in the art; MAP kinase inducers such as, e.g., anisomycin and anandamine; cell cycle blockers such as, e.g. aphidicolin, colcemid, 5-fluorouracil and homoharringtonine; acetylcholineesterase inhibitors such as, e.g., berberine; anti-estrogens such as, e.g. tamoxifen; pro-oxidants, such as, e.g., tert-butyl hydroperoxide, peroxynitrite, hydrogen peroxide and nitric oxide donors including but not limited to L-arginine, 5,5'-dinitrosodithiol, N-hydroxy-L-arginine, S-nitroso-N-acetylpenicillamine, S-nitrosoglutathione, NOR-1, NOR-3, NOR4,4-phenyl-3-furoxancarbonitrile, 3-morpholinosydnonimine, sodium nitroprusside and streptozotocin; glutathione depleting agents such as, e.g., ethacrynic acid (Meister, 1995 *Biochim. Biophys. Acta.* 1271:35); free radicals such as, e.g., nitric oxide; inorganic metal ions, such as, e.g., cadmium; DNA synthesis inhibitors such as, e.g., actinomycin D; DNA intercalators such as, e.g., doxorubicin, bleomycin sulfate, hydroxyurea, methotrexate, mitomycin C, camptothecin, and daunorubicin; protein synthesis inhibitors such as, e.g., cycloheximide, puromycin, and rapamycin; agents that effect microtubule formation or stability such as, e.g.: vinblastine, vincristine, colchicine, 4-hydroxyphenylretinamide, and paclitaxel; and other MPT inducers such as, e.g., Bax protein (Jurgenmeier et al., 1998 PNAS 95:4997–5002), calcium and inorganic phosphate (Kroemer et al., 1998 Ann. Rev. Physiol. 60:619).

In one embodiment of the subject invention method wherein the indicator of altered mitochondrial function is a cellular response to an apoptogen, cells in a biological sample that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by a person having ordinary skill in the art, for example by using light microscopy. As another example, cells undergoing apoptosis may exhibit fragmentation and disintegration of chromosomes, which may be apparent by microscopy and/or through the use of DNA-specific or chromatin-specific dyes that are known in the art, including fluorescent dyes. Such cells may also exhibit altered plasma membrane permeability properties as may be readily detected through the use of vital dyes (e.g., propidium iodide, trypan blue) or by the detection of lactate dehydrogenase leakage into the extracellular milieu. These and other means for detecting apoptotic ells by morphologic criteria altered plasma membrane permeability and related changes will be apparent to those familiar with the art.

In another embodiment of the subject invention method wherein the indicator of altered mitochondrial function is a cellular response to an apoptogen, cells in a biological sample may be assayed for translocation of cell membrane phosphatidylserine (PS) from the inner to the outer leaflet of the plasma membrane, which may be detected, for example, by measuring outer leaflet binding by the PS-specific protein annexin. (Martin et al., *J. Exp. Med.* 182:1545, 1995; Fadok et al., *J. Immunol.* 148:2207, 1992.) In still another embodiment of this aspect of the invention, a cellular response to an apoptogen is determined by an assay for induction of specific protease activity in any member of a family of apoptosis-activated proteases known as the caspases (see, e.g., Green et al., 1998 *Science* 281:1309). Those having skill in the art will be readily familiar with methods for determining caspase activity, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., 1997 *J. Neurosci.* 17:6165). The synthetic peptide Z-Tyr-Val-Ala-Asp-AFC, wherein "Z" indicates a benzoyl carbonyl moiety and AFC indicates 7-amino-4-trifluoromethylcoumarin (Kluck et al., 1997 *Science* 275: 1132; Nicholson et al., 1995 *Nature* 376:37), is one such substrate. Other non-limiting examples of substrates include nuclear proteins such as U1-70 kDa and DNA-PKcs (Rosen and Casciola-Rosen, 1997 *J. Cell. Biochem.* 64:50; Cohen, 1997 *Biochem. J.* 326:1).

As described above, the mitochondrial inner membrane may exhibit highly selective and regulated permeability for many small solutes, but is impermeable to large (>~10 kDa) molecules. (See, e.g., Quinn, 1976 *The Molecular Biology of Cell Membranes*, University Park Press, Baltimore, Md.). In cells undergoing apoptosis, however, collapse of mitochondrial membrane potential may be accompanied by increased permeability permitting macromolecule diffusion across the mitochondrial membrane. Thus, in another embodiment of the subject invention method wherein the indicator of altered mitochondrial function is a cellular response to an apoptogen, detection of a mitochondrial protein, for example cytochrome c or an intermembrane space protein, that has escaped from mitochondria in apoptotic cells, may provide evidence of a response to an apoptogen that can be readily determined. (Liu et al., *Cell* 86:147, 1996) Such detection of cytochrome c may be performed spectrophotometrically, immunochemically or by other well established methods for determining the presence of a specific protein.

For instance, release of cytochrome c from cells challenged with apoptotic stimuli (e.g., ionomycin, a well known calcium ionophore) can be followed by a variety of immunological methods. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDI™) system (Ciphergen, Palo Alto, Calif.) may be utilized to detect cytochrome c release from mitochondria in apoptogen treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDI™ mass spectrometer.

A person having ordinary skill in the art will readily appreciate that there may be other suitable techniques for quantifying apoptosis, and such techniques for purposes of determining an indicator of altered mitochondrial function that is a cellular response to an apoptogenic stimulus are within the scope of the methods provided by the present invention.

Free Radical Production as an Indicator of Altered Mitochondrial Function

In certain embodiments of the present invention, free radical production in a biological sample may be detected as an indicator of altered mitochondrial function. Although mitochondria are a primary source of free radicals in biological systems (see, e.g., Murphy et al., 1998 in *Mitochondria and Free Radicals in Neurodegenerative Diseases*, Beal, Howell and Bodis-Wollner, Eds., Wiley-Liss, New York, pp. 159–186 and references cited therein), the invention should not be so limited and free radical production can be an indicator of altered mitochondrial function regardless of the particular subcellular source site. For example, numerous intracellular biochemical pathways that lead to the formation of radicals through production of metabolites such as hydrogen peroxide, nitric oxide or superoxide radical via reactions catalyzed by enzymes such as flavin-linked oxidases, superoxide dismutase or nitric oxide synthetase, are known in the art, as are methods for detecting such radicals (see, e.g., Kelver, 1993 *Crit. Rev. Toxicol.* 23:21; Halliwell B. and J. M. C. Gutteridge, *Free Radicals in Biology and Medicine*, 1989 Clarendon Press, Oxford, UK; Davies, K. J. A. and F. Ursini, *The Oxygen Paradox*, Cleup Univ. Press, Padova, IT). Altered mitochondrial function, such as failure at any step of the ETC, may also lead to the generation of highly reactive free radicals. As noted above, radicals resulting from altered mitochondrial function include reactive oxygen species (ROS), for example, superoxide, peroxynitrite and hydroxyl radicals, and potentially other reactive species that may be toxic to cells. Accordingly, in certain preferred embodiments of the invention an indicator of altered mitochondrial function may be a detectable free radical species present in a biological sample. In certain particularly preferred embodiments, the detectable free radical will be a ROS.

Methods for detecting a free radical that may be useful as an indicator of altered mitochondrial function are known in the art and will depend on the particular radical. Typically, a level of free radical production in a biological sample may be determined according to methods with which those skilled in the art will be readily familiar, including but not limited to detection and/or measurement of: glycoxidation products including pentosidine, carboxymethylysine and pyrroline; lipoxidation products including glyoxal, malondialdehyde and 4-hydroxynonenal; thiobarbituric acid reactive substances (TBARS; see, e.g., Steinbrecher et al., 1984 Proc. Nat. Acad. Sci. USA 81:3883; Wolff, 1993 Br. Med. Bull. 49:642) and/or other chemical detection means such as salicylate trapping of hydroxyl radicals (e.g., Ghiselli et al., 1998 Meths. Mol. Biol. 108:89; Halliwell et al., 1997 Free Radic. Res. 27:239) or specific adduct formation (see, e.g., Mecocci et al. 1993 Ann. Neurol. 34:609; Giulivi et al., 1994 Meths. Enzymol. 233:363) including malondialdehyde formation, protein nitrosylation, DNA oxidation including mitochondrial DNA oxidation, 8'-OH-guanosine adducts (e.g., Beckman et al., 1999 Mutat. Res. 424:51), protein oxidation, protein carbonyl modification (e.g., Baynes et al., 1991 Diabetes 40:405; Baynes et al., 1999 Diabetes 48:1); electron spin resonance (ESR) probes; cyclic voltametry; fluorescent and/or chemiluminescent indicators (see also e.g., Greenwald, R. A. (ed.), Handbook of Methods for Oxygen Radical Research, 1985 CRC Press, Boca Raton, Fla.; Acworth and Bailey, (eds.), Handbook of Oxidative Metabolism, 1995 ESA, Inc., Chelmsford, Mass.; Yla-Herttuala et al., 1989 J. Clin. Invest. 84:1086; Velazques et al., 1991 Diabetic Medicine 8:752; Belch et al., 1995 Int. Angiol. 14:385; Sato et al., 1979 Biochem. Med. 21:104; Traverso et al., 1998 Diabetologia 41:265; Haugland, 1996 Handbook of Fluorescent Probes and Research Chemicals—Sixth Ed., Molecular Probes, Eugene, Oreg., pp. 483–502, and references cited therein). For example, by way of illustration and not limitation, oxidation of the fluorescent probes dichlorodihydrofluorescein diacetate and its carboxylated derivative carboxydichlorodihydrofluorescein diacetate (see, e.g., Haugland, 1996, supra) may be quantified following accumulation in cells, a process that is dependent on, and proportional to, the presence of reactive oxygen species (see also, e.g., Molecular Probes On-line Handbook of Fluorescent Probes and Research Chemicals, at http://www.probes.com/handbook/toc.html). Other fluorescent detectable compounds that may be used in the invention for detection of free radical production include but are not limited to dihydrorhodamine and dihydrorosamine derivatives, cis-parinaric acid, resorufin derivatives, lucigenin and any other suitable compound that may be known to those familiar with the art.

Thus, as also described above, free radical mediated damage may inactivate one or more of the myriad proteins of the ETC and in doing so, may uncouple the mitochondrial chemiosmotic mechanism responsible for oxidative phosphorylation and ATP production. Indicators of altered mitochondrial function that are ATP biosynthesis factors, including determination of ATP production, are described in greater detail herein. Free radical mediated damage to mitochondrial functional integrity is also just one example of multiple mechanisms associated with altered mitochondrial function that may result in collapse of the electrochemical potential maintained by the inner mitochondrial membrane. Methods for detecting changes in the inner mitochondrial membrane potential are described above and in co-pending U.S. patent application Ser. No. 09/161,172.

Samples

Biological samples may comprise any tissue or cell preparation in which at least one candidate indicator of altered mitochondrial function can be detected, and may vary in nature accordingly, depending on the particular indicator(s) to be compared. Thus, as will be apparent to those having ordinary skill in the art based on the disclosure herein, in certain highly preferred embodiments biological samples comprise cells or cell preparations containing mitochondria, and in certain other preferred embodiments biological samples may comprise submitochondrial particles. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiable cell lines, transformed cell lines and the like. In particularly preferred embodiments the subject or biological source is a human or non-human vertebrate, and in other particularly preferred embodiments the subject or biological source is a vertebrate-derived primary cell culture or culture-adapted cell line as provided herein, but the invention need not be so limited. As a non-limiting example by way of illustration, in certain embodiments the invention contemplates a biological sample that may be a non-vertebrate tissue or cell preparation that has been artificially manipulated, for example through recombinant genetic engineering, to contain one or more vertebrate-derived genes, gene products or the like, such as mitochondrial molecular components and/or ATP biosynthesis factors as provided herein. For instance, a number of yeast and insect cell lines may be readily reconstituted with heterologous vertebrate-derived components according to established methods with which those skilled in the art will be familiar, to generate a model system for an arthritic disorder as provided herein. Accordingly, numerous variations and modifications to biological samples are within the contemplated scope and spirit of the present invention.

In certain other particularly preferred embodiments of the invention, the subject or biological source may be suspected of having or being at risk for having an arthritic disorder, and in certain preferred embodiments of the invention the subject or biological source may be known to be free of a risk or presence of such a disease.

In certain other preferred embodiments where it is desirable to determine whether or not a subject or biological source falls within clinical parameters indicative of an arthritic disorder, signs and symptoms of an arthritic disorder that are accepted by those skilled in the art may be used to so designate a subject or biological source, for example clinical signs referred to in Primer on the Rheumatic Diseases ($7^{th}$ Edition, J. H. Klippel (ed.), 1997 The Arthritis Foundation, Atlanta, Ga.) and references cited therein, or other means known in the art for diagnosing an arthritic disorder.

In certain aspects of the invention, biological samples containing at least one candidate indicator (or co-predictor as provided herein) of altered mitochondrial function may be obtained from the subject or biological source before and after contacting the subject or biological source with a candidate agent, for example to identify a candidate agent capable of effecting a change in the level of the indicator (or co-predictor) of altered mitochondrial function as defined above, relative to the level before exposure of the subject or biological source to the agent. The indicator may optionally, in certain preferred embodiments wherein the indicator is an enzyme or an ATP biosynthesis factor, be determined as a measure of enzyme (or ATP biosynthesis factor) catalytic activity in the sample, as a measure of enzyme (or ATP biosynthesis factor) quantity in the sample or as a measure of enzyme (or ATP biosynthesis factor) expression level in the sample, as provided herein.

In a most preferred embodiment of the invention, the biological sample containing at least one candidate indicator of altered mitochondrial function comprises a chondrocyte, and still more preferably, an articular chondrocyte. Chondrocytes can be obtained, for example, from normal mature cartilage tissue. For instance, U.S. Pat. Nos. 4,846,835 and 5,041,138 disclose isolation of chondrocytes by digesting articular cartilage in a collagenase solution, followed by mitotic expansion of the chondrocytes in vitro. In another preferred embodiment of the invention, the biological sample containing at least one candidate indicator of altered mitochondrial function may comprise a matrix vesicle (MV) derived from a chondrocyte (e.g., Anderson, 1988 *Rheum. Dis. Clin. North Amer.* 14:303; Doyle, 1982 *J. Pathol.* 136:199; Doherty, 1994 *Hosp. Pract. Off Ed.* 29:93), for example, an MV prepared according to any of a number of established procedures (e.g., Johnson et al., 1999 *J. Bone Miner. Res.* 14:883) or by other techniques with which those having ordinary skill in the art will be familiar.

The initiation of matrix calcification by chondrocytes, as well as by osteoblasts, appears to be mediated by the release of membrane-limited cell fragments known as matrix vesicles (MVs). MV components, including a variety of enzymes, modify the extracellular matrix, and the MV interiors serve as a sheltered environment for hydroxyapatite crystal formation (Anderson, *Clin. Orthopaed. Rel. Res.* 314:266–280, 1995; Boskey et al., *Calcif Tissue Int.* 60:309–315, 1997; Boskey, *Connect. Tissue Res.* 35:357–363, 1996; and Goldberg, *Prog. Histochem. Cytochem.* 31:1–187, 1996). Methods of preparing MVs are described herein, and other methods are known in the art (see, e.g., Johnson et al., *J. Bone Miner. Res.* 14:883–892, 1999, and U.S. Pat. No. 5,656,450).

Mitochondria and SMPs can be prepared by a variety of methods (see, e.g., Fleischer et al., *Methods Enzymol.* 31:292–299, 1974; Pedersen et al., *Methods Cell. Biol.* 20:411–481, 1978; della-Cioppa et al., *Mol. Cell. Endocrinol.* 48:111–120, 1986; and Lauquin et al., *Biochim. Biophys. Acta* 460:331–345, 1977). For example, to prepare mitochondria and/or SMPs, the following procedure may be used. Cell lysates are centrifuged at 600 g for 10 minutes at 4° C., and this first supernatant is removed and set aside. The pellet, which comprises plasma membrane material, is washed with 100 ul of MSB (210 mM mannitol, 70 mM sucrose, 50 mM Tris-HCl, pH 7.4, and 10 mM EDTA) and centrifuged at 600 g for 10 minutes at 4° C., in order to produce a second supernatant. The first and second supernatants are combined and centrifuged at 14,000 g for 15 minutes at 4° C.; the resultant pellet represents a mitochondrial fraction that is resuspended in MSB in order to prepare mitochondria. Such mitochondria may be incubated with 0.25 mg/ml digitonin (Roche Molecular Biochemicals, formerly Boehringer Mannheim, Indianapolis, Ind.) for 2 minutes and sonicated for 3 minutes at 50% duty cycle in a cup-horn sonicator to produce submitochondrial particles (SMPs).

Accordingly, a biological sample as provided herein may in certain preferred embodiments comprise a chondrocyte, chondrocyte-derived MVs and/or chondrocyte-derived submitochondrial particles (SMP), in which levels of one or more indicators of altered mitochondrial function may be compared.

In another preferred embodiment of the invention, the biological sample containing at least one candidate indicator of altered mitochondrial function may comprise whole blood, and may in another preferred embodiment comprise a crude buffy coat fraction of whole blood, which is known in the art to comprise further a particulate fraction of whole blood enriched in platelets and in nucleated blood cells (e.g., white blood cells such as lymphocytes, monocytes and granulocytes including neutrophils, eosinophils and basophils), and substantially depleted of erythrocytes. Those familiar with the art will know how to prepare such a buffy coat fraction, which may be prepared, for example, by differential density sedimentation of blood components under defined conditions, including the use of density dependent separation media, or by other methods. In other preferred embodiments, the biological sample containing at least one indicator of altered mitochondrial function may comprise an enriched, isolated or purified blood cell subpopulation fraction such as, for example, lymphocytes, polymorphonuclear leukocytes, granulocytes and the like. Methods for the selective preparation of particular hematopoietic cell subpopulations are well known in the art (see, e.g., *Current Protocols in Immunology*, J. E. Coligan et al., (Eds.) 1998 John Wiley & Sons, NY).

According to certain embodiments of the invention, the particular cell type or tissue type from which a biological sample is obtained may influence qualitative or quantitative aspects of at least one candidate indicator of altered mitochondrial function contained therein, relative to the corresponding candidate indicator of altered mitochondrial function obtained from distinct cell or tissue types of a common biological source. It is therefore within the contemplation of the invention to quantify at least one candidate indicator of altered mitochondrial function in biological samples from different cell or tissue types as may render the advantages of the invention most useful for an arthritic disorder, and further for a particular degree of progression of a known or suspected arthritic disorder in a vertebrate subject. The relevant cell or tissue types will be known to those familiar with such diseases.

For example, as provided herein, articular cartilage chondrocytes may represent a particularly preferred cell type in which oxidative energy demand (e.g., ATP demand) is required for joint maintenance and healthy joint function. Other biological samples derived from cell or tissue types that use mitochondrial ATP for cellular functions involved in joint development, stabilization, maintenance and repair processes such as cartilage homeostasis, bone or ligament graft healing, scar tissue resorption or connective tissue remodeling, for example bone cells, osteoblasts, osteoclasts, bone marrow stromal cells, myocytes, motor nerve/end plate cells, inflammatory cells and/or synoviocytes may also be particularly useful.

In order to determine whether a mitochondrial alteration may contribute to a particular disease state, it may be useful to construct a model system for diagnostic tests and for screening candidate therapeutic agents in which the nuclear genetic background may be held constant while the mitochondrial genome is modified. It is known in the art to deplete mitochondrial DNA from cultured cells to produce $\rho^0$ cells, thereby preventing expression and replication of mitochondrial genes and inactivating mitochondrial function. It is further known in the art to repopulate such $\rho^0$ cells with mitochondria derived from foreign cells in order to assess the contribution of the donor mitochondrial genotype to the respiratory phenotype of the recipient cells. Such cytoplasmic hybrid cells, containing genomic and mitochondrial DNAs of differing biological origins, are known as cybrids. See, for example, International Publication Number WO 95/26973 and U.S. Pat. No. 5,888,498 which are hereby incorporated by reference in their entireties, and references cited therein.

According to the present invention, a level of at least one indicator of altered mitochondrial function is determined in a biological sample from a subject or biological source. For subjects that are asymptomatic, or that meet clinical criteria for having or being at risk for having an arthritic disorder (see e.g., Primer on the Rheumatic Diseases, 7$^{th}$ Edition, J. H. Klippel (ed.), 1997 The Arthritis Foundation, Atlanta, Ga.) such determination may have prognostic and/or diagnostic usefulness. For example, where other clinical indicators of an arthritic disorder are known, levels of at least one indicator of altered mitochondrial function in subjects known to be free of a risk or presence of an arthritic disorder based on the absence of these indicators may be determined to establish a control range for such level(s). The levels may also be determined in biological samples obtained from subjects suspected of having or being at risk for having an arthritic disorder, and compared to the control range determined in disease free subjects. Those having familiarity with the art will appreciate that there may be any number of variations on the particular subjects, biological sources and bases for comparing levels of at least one indicator of altered mitochondrial function that are useful beyond those that are expressly presented herein, and these additional uses are within the scope and spirit of the invention.

For instance, determination of levels of at least one indicator of altered mitochondrial function may take the form of a prognostic or a diagnostic assay performed on a surgically resected cartilage sample, on whole blood collected from a subject by routine venous blood draw, on buffy coat cells prepared from blood or on biological samples that are other cells, organs or tissue from a subject. Alternatively, in certain situations it may be desirable to construct cybrid cell lines using mitochondria from either control subjects or subjects suspected of being at risk for an arthritic disorder. Such cybrids may be used to determine levels of at least one indicator of altered mitochondrial function for diagnostic or predictive purposes, or as biological sources for screening assays to identify agents that may be suitable for treating an arthritic disorder based on their ability to alter the levels of at least one indicator of altered mitochondrial function in treated cells.

In one embodiment of this aspect of the invention, therapeutic agents or combinations of agents that are tailored to effectively treat an individual patient's particular disease may be identified by routine screening of candidate agents on cybrid cells constructed with the patient's mitochondria. In another embodiment, a method for identifying subtypes of an arthritic disorder is provided, for example, based on differential effects of individual candidate agents on cybrid cells constructed using mitochondria from different arthritic subjects.

In other embodiments, the invention provides a method of identifying an agent suitable for treating a subject suspected of being at risk for having an arthritic disorder by comparing the level of at least one indicator of altered mitochondrial function, or by comparing the level of a co-predictor of altered mitochondrial function and at least one distinct indicator of altered mitochondrial function, in the presence and absence of a candidate agent, to determine the suitability of the agent for treating an arthritic disorder. In certain embodiments the step of comparing may be performed in one or more biological samples obtained from a subject in the presence and absence of a candidate agent. By way of illustration and not limitation, whether an agent is suitable for treating a subject suspected of being at risk for having an arthritic disorder will be readily apparent without undue experimentation to a person having ordinary skill in the art based on the disclosure herein, and with regard to the several embodiments provided herein. Thus, where the level of at least one indicator of altered mitochondrial function as provided herein (and, optionally, of at least one co-predictor of altered mitochondrial function as provided herein) in the presence of the candidate agent is changed in a statistically significant way to become a level closer to that found in a subject known to be free of a risk for having an arthritic disorder, relative to the level of the same indicator (and optionally, the same co-predictor) in the absence of the agent, it will be appreciated that the agent is suitable for treating a subject suspected of being at risk for having an arthritic disorder.

In certain related embodiments, the invention provides a method of determining the suitability of an agent for treating a subject suspected of being at risk for having an arthritic disorder by comparing the level of at least one indicator of altered mitochondrial function (or by comparing the level of a co-predictor of altered mitochondrial function and at least one distinct indicator of altered mitochondrial function) in a biological sample obtained from the subject before and after administering a candidate agent to the subject. In certain other related embodiments, the invention provides a method of determining the suitability of an agent for treating a vertebrate subject suspected of being at risk for having an arthritic disorder, by comparing the level of at least one indicator of altered mitochondrial function (or by comparing the level of a co-predictor of altered mitochondrial function and at least one distinct indicator of altered mitochondrial function) in at least one biological sample obtained from a plurality of subjects before and after administering to each of the subjects a candidate agent.

Based on the disclosure herein, determination of whether an agent is suitable may depend on the particular diagnostic, therapeutic, clinical, research and/or other goal, and will be within the knowledge of persons having ordinary skill in the art. Accordingly, identification of an agent that alters (e.g., increases or decreases in a statistically significant manner) the level of at least one indicator of altered mitochondrial function as provided herein can be used to indicate that such an agent may be used to treat an arthritic disorder and/or to prevent, delay or retard the onset of an arthritic disorder and/or to reduce the severity of an arthritic disorder. As disclosed herein, the present invention relates in part to the unexpected discovery that aerobic mitochondrial respiration is active in vertebrate articular chondrocytes and that altered aerobic respiration (e.g., mitochondrial oxidative phosphorylation) contributes to the pathogenesis of arthritic disorders. Thus, screening assays (including, in certain preferred embodiments, high throughput screens) provided by the present invention, which permit determination of the effect of a candidate agent on at least one indicator of altered mitochondrial function, may be designed to identify agents that alter the levels of such indicators. For example, in certain subjects or in certain situations a suitable agent may alleviate symptoms or, and/or reverse underlying metabolic abnormalities in, an arthritic disorder. In certain situations, for instance, an agent that alters (e.g., increases or decreases) ATP synthesis may be a desirable and suitable agent. In other contexts, an agent that regulates bone mass, for example, by stimulating bone growth and/or by impairing bone loss, may be a desirable and suitable agent. As described below, alterations (e.g., an increase or decrease) according to the present disclosure in one or more indicators of mitochondrial function, and in particular, alterations in those indicators that relate to ATP biosynthesis factors, may regulate one or more physiological parameters of significance to an arthritic disorder, such as bone mass.

In still other certain embodiments, the present invention pertains in part to screening assays for agents that induce one or more arthritic disorders in a vertebrate subject, for example, to produce a biological model system for an arthritic disorder, such as an animal model or a cell line. Accordingly, the invention provides a method of identifying an agent that induces or contributes to the severity of an arthritic disorder, by comparing the level of at least one indicator of altered mitochondrial function (or by comparing the level of a co-predictor of altered mitochondrial function and at least one distinct indicator of altered mitochondrial function) in a biological sample obtained from the subject before and after administering a candidate agent to the subject. Related variations on such embodiments are within the contemplated scope of the invention and will be appreciated by those familiar with the art.

In particularly preferred embodiments that relate to a therapeutic agent and/or to an inducing agent, the agent is a small molecule. Candidate agents for use in a method of screening for a modulator of an indicator of altered mitochondrial function according to the present invention may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples, and then assayed for their ability to increase or decrease the level of at least one indicator of altered mitochondrial function.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666, which are hereby incorporated by reference in their entireties) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures, and tested for their influence on an indicator of altered mitochondrial function, according to the present disclosure.

The present invention provides compositions and methods that are useful in pharmacogenomics, for the classification and/or stratification of a subject or patient population. In one embodiment, for example, such stratification may be achieved by identification in a subject or patient population of one or more distinct profiles of at least one indicator of altered mitochondrial function that correlate with an arthritic disorder. Such profiles may define parameters indicative of a subject's predisposition to develop an arthritic disorder, and may further be useful in the identification of novel subtypes of an arthritic disorder. In another embodiment, correlation of one or more traits in a subject with at least one indicator of altered mitochondrial function may be used to gauge the subject's responsiveness to, or the efficacy of, a particular therapeutic treatment. In another embodiment of the invention, measurement of the level(s) of at least one indicator of altered mitochondrial function in a biological sample from a subject is combined with identification of the status of cartilage damage from arthritis in the subject, as assessed, for example, by standard radiographs, to determine the risk for, or presence of, an arthritic disorder in the subject. By using the combination of the methods for determining levels of at least one indicator of altered mitochondrial function as disclosed herein, and methods known in the art for determining the presence of an arthritic disorder (see e.g., *Primer on the Rheumatic Diseases, 7th* Edition, J. H. Klippel (ed.), 1997 The Arthritis Foundation, Atlanta, Ga.), an enhanced ability to detect the relative risk for an arthritic disorder is provided by the instant invention along with other related advantages. Similarly, where levels of at least one indicator of altered mitochondrial function and risk for an arthritic disorder are correlated, the present invention provides advantageous methods for identifying agents suitable for treating an arthritic disorder, where such agents affect levels of at least one indicator of altered mitochondrial function in a biological source.

As described herein, determination of levels of at least one indicator of altered mitochondrial function may also be used to stratify an arthritic patient population (i.e., a population classified as having an arthritic disorder by independent criteria). Accordingly, in another preferred embodiment of the invention, determination of levels of at least one indicator of altered mitochondrial function in a biological sample from an arthritic subject may provide a useful correlative indicator for that subject. An arthritic subject so classified on the basis of levels of at least one indicator of altered mitochondrial function may be monitored using arthritis clinical parameters referred to above, such that correlation between levels of at least one indicator of altered mitochondrial function and any particular clinical score used to evaluate an arthritic disorder may be monitored. For example, stratification of an arthritis patient population according to levels of at least one indicator of altered mitochondrial function may provide a useful marker with which to correlate the efficacy of any candidate therapeutic agent being used in arthritic subjects.

In certain other embodiments, the invention provides a method of treating a patient having an arthritic disorder by administering to the patient an agent that substantially restores at least one indicator of altered mitochondrial function to a level found in control or normal subjects. In one embodiment the indicator of altered mitochondrial function is the amount of ATP produced. In another embodiment, the indicator (or co-predictor) of altered mitochondrial function is the amount of mtDNA present. In a most preferred embodiment, an agent that substantially restores (e.g., increases or decreases) at least one indicator of altered mitochondrial function to a normal level effects the return of the level of that indicator to a level found in control subjects. In another preferred embodiment, the agent that substantially restores such an indicator confers a clinically beneficial effect on the subject. In another embodiment, the agent that substantially restores the indicator promotes a statistically significant change in the level of at least one indicator (or co-predictor) of altered mitochondrial function. As noted herein, those having ordinary skill in the art can readily determine whether a change in the level of a particular indicator brings that level closer to a normal value and/or clinically benefits the subject. Thus, an agent that substantially restores at least one indicator of altered mitochondrial function to a normal level may include an agent capable of fully or partially restoring such level.

Accordingly, in certain preferred embodiments, a pharmaceutical composition suitable for treating an arthritic disorder comprises a mitochondria protective agent and/or a mitochondrial function-altering agent. Thus, mitochondria protective agents may be used to prevent or treat arthritic disorders, such as osteoarthritis, degenerative joint disease and the like, and to promote the healing of injured cartilage, for example, cartilage damaged by trauma or repetitive motion disorder. Without wishing to be bound by any particular theory, some such mitochondrial protective agents may have activity as antioxidants and presumably act by preventing or ameriolating the effects of oxidative stress damage to mitochondria (for a review, see, e.g., Kowaltowski et al., *Free Radical Biol. Med.* 26:463–471, 1999). Other such mitochondrial protective agents act to prevent programmed cell death (apoptosis), which may contribute to the development of osteoarthritis (Blanco et al., *Arthritis &Rheumatism* 41:284–289, 1998).

In certain embodiments, such mitchondria protective agents may be antioxidant compounds. Antioxidant compounds include, by way of example and not limitation, the antioxidant compounds described in copending U.S. patent application Ser. Nos. 09/237,999 and 09/299,044; biphenyl compounds such as Honokiol (Chiu et al., *Life Sci.* 61:1961–1971, 1997), Magnolol and Probuchol; Propofol; flavonoids such as, for example, kaempferol, quercetin, myricetin, chrysin, apigenin, naringenin, Taxifolin, catechin ([2R,3S]-2-[3,4-dihydroxyphenyl]-3,4-dihydro-1 [2H]-benzopyran-3,4,7-triol), epicatechin and apigenin (for a review, see, e.g., Rice-Evans et al., *Free Radical Biology &Medicine* 20:933–956, 1996); α-lipoic acid; vutin hydrate; propyl gallate (3,4,5-trihydroxybenzoic acid propyl ester); Trolox®; metalloporphyrins such as MnTBAP [Mn(III) tetrakis (4-benzoic acid)porphyrin chloride] and MnTMPyP [Mn(III) tetrakis (1-methyl-4-pyridyl)porphyrin pentachloride] (Day et al., *Free Radical Biology &Medicine* 26:730–736, 1999; Batinic-Haberle et al., *J. Biol. Chem.* 273:24521–24528, 1998; morin (2',3,4',5,7-pentahydroxyflavone); Resveratrol; Rutin; LNAC (N-acetyl-L-cysteine); salen-manganese derivatives, such as those described in U.S. Pat. No. 5,834,509; antioxidant esters of non-steroidal anti-inflammatory drugs (NSAIDs), such as are described in U.S. Pat. No. 5,908,849; L-ergothioneine (published PCT patent application WO 98/36748); ortho-hydroxypyridinone derivatives (PCT application WO 99/23075); dipyridamole and derivatives thereof such as, e.g., RA-14, RA-47 and RA-25 (Nepomuceno et al., *Biochim. Biophys. Acta* 1418: 285–294, 1999; Nepomuceno et al., *Free Rad. Biol. Med* 23:1046–1054, 1997); SR27338 (Herbert et al., *J. Lipid Mediat.* 8:31–51, 1993); Ginkgo bilboa extract, EGb 761 (Shen et al., *Biochem. Mol. Biol. Int.* 35:125–134, 1995); N-acetylcysteine (Cossarizza et al., *Exp. Cell. Res.* 220: 232–240, 1995); propranolol (Freedman et al., *Free Radic. Biol. Med.* 11:197–206, 1991); Ebselen and the glutathione adduct thereof (Narayanaswami et al., *Biochem Pharmacol.* 40:1623–1629, 1990); dihydroquinolines such as MTDQ-DA [Rath et al., *Basic Res. Cardiol.* 82 (Suppl. 2): 335–345, 1987]; Stobadine (Stolc et al., *Brain Res. Bull.* 42:335–340, 1997); glutathione (Cawthon et al., *Poult. Sci.* 78:114–124, 1999); Trinolein (Chan et al., *Pharmacology* 52:216–225, 1996); Carvedilol (Moreno et al., *Rev. Port. Cardiol.* 17 (Suppl. 2): 1163–1177, 1998); Tauroursodeoxycholate (Vendemiale et al., *J. Hepatol.* 28:46–53, 1998); methionine, which causes increases in levels of free radical scavengers (Selvam et al., *Indian J. Biochem. Biophys.* 29:364–370, 1992); CoQ10 and other ubiquinones (Kagan et al., *Free Rad. Biol. Med.* 9:117–126, 1990); antioxidants described in published PCT patent application WO 98/25905; Vitamin C (L-ascorbic acid; Jyonouchi et al., *Nutr. Cancer* 28:115–124, 1997) and Vitamin E (Urano et al., *Eur. J. Biochem.* 245: 64–70, 1997; Ham et al., *Arch. Biochem. Biophys.* 339: 157–164, 1997), both singly and in combination with each other and/or other agents such as selenium (Scholz et al., *Biochem. Mol. Biol. Int.* 42:997–1006, 1997; Combs et al., *Fed. Proc.* 34:2090–2095, 1975) or thiols and cholesterol (Vatassery et al., *Neurochem. Int.* 26:527–535, 1995); and combinations thereof. Antioxidants may de delivered to a subject in need thereof via sustained release formulations designed for therapeutic delivery thereof, such as are described in U.S. Pat. No. 5,897,879, or liposomal formulations, such as are described in U.S. Pat. No. 5,747,026.

Such mitchondria protective agents may also be compounds that act to prevent one or more steps in cellular pathways leading to apoptotis (programmed cell death). Such anti-apoptotic compounds include, by way of example and not limitation, inhibitors of apoptotic proteases known as caspases (for a review, see, e.g., Thornberry et al., *Science* 28:132–136, 1998), including oligopeptide derivatives, such as those described by Thornberry (Chem. Biol. 5:R97–R03, 1998) and Garcia-Calvo et al. (*J. Biol. Chem.* 273:32608–32613, 1998); antisense compounds such as those described in U.S. Pat. No. 5,929,042; inhibitors of the mitochondrial permeability transition such as, for example, cyclosporins including cyclosporin A; bongkrekic acid and isobongkrekic acid; and thapsigargin-protective compounds such as those described in copending U.S. patent application Ser. Nos. 09/237,999 and 09/299,044.

Thus, within these and other related embodiments, an agent may be administered to a patient for treatment or prevention of an arthritic disorder as provided herein. Preferably the agent is a mitochondrial function-altering agent (which may include a mitochondria protective agent as provided herein) that restores at least one indicator of altered mitochondrial function to a level found in control or normal subjects. Such agents are preferably part of a pharmaceutical composition when used in the methods of the present invention. The pharmaceutical composition will include at least one of a pharmaceutically acceptable carrier, diluent or excipient, in addition to one or more mitochondrial function-altering agents and, optionally, other components.

A mitochondrial function-altering agent (including a mitochondria protective agent as provided herein) identified according to this invention, or a pharmaceutically acceptable salt thereof, is administered to a patient in a therapeutically effective amount. A therapeutically effective amount is an amount calculated to achieve the desired effect. It will be apparent to one skilled in the art that the route of administration may vary with the particular treatment. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include intraarterial, intravenous, intradermal, intramuscular, subcutaneous, intraperitoneal, intrathecal and intraocular.

The required dosage may vary with the particular treatment and route of administration. In general, dosages for mitochondria protecting agents will be from about 1 to about 5 milligrams of the compound per kilogram of the body weight of the host animal per day; frequently it will be between about 100 μg and about 5 mg but may vary up to about 50 mg of compound per kg of body weight per day. Therapeutic administration is generally performed under the guidance of a physician, and pharmaceutical compositions contain the mitochondria protecting agent in a pharmaceutically acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

In one embodiment of the invention, pharmaceutical compositions comprising one or more compounds of this invention are entrapped within liposomes. Liposomes are microscopic spheres having an aqueous core surrounded by one or more outer layer(s) made up of lipids arranged in a bilayer configuration (see, e.g., Chonn et al., *Current Op. Biotech.* 6:698, 1995). The therapeutic potential of liposomes as drug delivery agents was recognized nearly thirty years ago (Sessa et al., *J. Lipid Res.* 9:310, 1968). Liposomes include "sterically stabilized liposome," a term which, as used herein, refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters* 223:42, 1987; Wu et al., *Cancer Research* 53:3765, 1993).

Various liposomes comprising one or more glycolipids are known in the art. Papahadjopoulos et al. (*Ann. N.Y. Acad. Sci.*, 507:64, 1987) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.* 85:6949, 1988). U.S. Pat. No. 4,837,028 and WO 88/04924, both to Allen et al., disclose liposomes comprising (1) sphingomyelin and (2) the ganglioside GMI or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Various liposomes comprising lipids derivatized with one or more hydrophilic polymers, and methods of preparation thereof, are known in the art. Sunamoto et al. (*Bull. Chem. Soc. Jpn.* 53:2778, 1980) described liposomes comprising a non-ionic detergent, $2C_{12}15G$, that contains a PEG moiety. Illum et al. (*FEBS Letters* 167:79, 1984) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Letts.* 268:235, 1990) described experiments demonstrating that liposomes comprising phosphatidylethanolamine (PE) derivatized with PEG or PEG stearate have significant increases in blood circulation half-lives. Blume et al. (*Biochimica et Biophysica Acta* 1029:91, 1990) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Mitochondrial function-altering agents identified according to the present invention, including mitochondria protective agents as provided herein, also include prodrugs thereof. As used herein, a "prodrug" is any covalently bonded carrier that releases in vivo the active parent drug when such prodrug is administered to a vertebrate subject. Prodrugs of a given compound are prepared by modifying functional groups present on the compound in such a way that the modifications are cleaved, either in routine manipulation or in vivo, to the parent compound. Prodrugs include, but are not limited to, compounds wherein hydroxy, amine or sulfhydryl groups are bonded to any group of the parent compound via a bond that, when the prodrug is administered to a subject, cleaves to form the free hydroxyl, amino or sulfhydryl group, respectively. Representative examples of prodrugs include, but are not limited to, acetate, formate and benzoate derivatives of alcohol and amine functional groups.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used. Optionally, for certain routes of administration, an anesthetic may be included in the formulation.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more mitochondrial function-altering agents may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intrathecal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more mitochondrial function-altering agents, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of mitochondrial function-altering agent such that a suitable dosage will be obtained. Typically, this amount is at least 0.01 wt % of a mitochondrial function-altering agent in the composition. When intended for oral administration, this amount may be varied to be between 0.1 and about 70% of the weight of the composition. Preferred oral compositions contain between about 4% and about 50% of mitochondrial function-altering agent(s). Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the mitochondrial function-altering agent of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In the methods of the invention, the mitochondrial function-altering agent(s) may be administered through use of insert(s), bead(s), timed-release formulation(s), patch(es) or fast-release formulation(s). It will be evident to those of ordinary skill in the art that the optimal dosage of the mitochondrial function-altering agent(s) may depend on the weight and physical condition of the patient; on the severity and longevity of the physical condition being treated; on the particular form of the active ingredient, the manner of administration and the composition employed. It is to be understood that use of a mitochondrial function-altering agent in chemotherapy can involve such an agent being bound to another compound, for example, a monoclonal or polyclonal antibody, a protein or a liposome, which assist the delivery of said compound.

Some therapeutic and prophylactic methods of the invention involve the in vitro/ex vivo manipulation of chondrocytes to improve their ability to carry out mitochondrial functions, followed by implantation into an animal in need of such treatment. One method of improving the mitochondrial function of chondrocytes involves depleting chondrocytes of their endogenous mitochondrial DNA (mtDNA) to produce rho-zero ($\rho^0$) cells, and subsequently introducing into such $\rho^0$ cells mitochondria derived from an animal known to not have or be prone to an arthritic disorder. The resultant cellular hybrids, or cybrids, thus have a nuclear component derived from the parent chondrocytes and a mitochondrial component that is derived from a healthy animal. These cybrid chondrocytes are expected to have improved mitochondrial function and to better carry out chondrocyte-mediated arthritis-limiting activities as a result. If the chondrocytes that are manipulated ex vivo are derived from the same animal into which they are eventually reintroduced, the methods of the invention offer the further advantage of increased graft acceptance by the host and improved clinical results, due to a decreased potential for immunological rejection (i.e., graft rejection) of the implanted cells by the host immune system. According to this non-limiting theory, this advantage improves the efficiency of the presently disclosed methods because the implanted chondrocytes survive in greater numbers and/or for longer duration in the animal. Additionally, this approach also reduces the likelihood of undesirable side-effects of such treatments, for example, side effects due to immune reactions and their sequelae (e.g., immunosuppressants). These methods of the present invention also circumvent limitations of other ex vivo methods involving manipulation of chondrocytes, such as the low transfection efficiency of human articular chondrocytes encountered in certain instances (Terkeltaub, *J. Clin. Invest.* 94:2173, 1994).

Accordingly as provided herein, chondrocytes may be isolated, mitotically expanded in vitro and modified to alter (e.g., increase or decrease) one or more indicators of altered mitochondrial function. For example by way of illustration and not limitation, such chondrocytes may be treated with a suitable agent that alters mitochondrial function, wherein the agent may be any agent identified according to the methods described herein, including a small molecule; a protein or peptide; a nucleic acid molecule including a transgene, a ribozyme, a plasmid, a vector such as a recombinant expression vector, an antisense nucleic acid or any other agent that alters a level of at least one indicator of altered mitochondrial function. Chondrocytes so modified may be directly administered to the site of damage in a subject suffering from an arthritic disorder, where biosynthesis of new cartilage may occur. Alternatively, cultured chondrocytes may, under appropriate conditions, synthesize new cartilage tissue in vitro, which tissue can then be graft-implanted at the site of tissue damage. U.S. Pat. No. 4,846,835 discloses the seeding of autologous chondrocytes onto a three dimensional collagen matrix which is then inserted in vivo at the site of an articular cartilage lesion and fixed in place using a sutured periosteal flap. U.S. Pat. No. 5,041,138 discloses the in vitro growth of cartilaginous structures by seeding chondrocytes onto a three dimensional biodegradable matrix for subsequent implantation, or, alternatively, proliferating free chondrocytes in vitro, which are then administered directly to the site of damage.

According to certain embodiments of the invention, polypeptide growth factors may be added to chondrogenic cells to enhance or stimulate the production of articular cartilage specific proteoglycans and/or collagen (see, e.g., Luyten & Reddi, 1992, in *Biological Regulation of the Chondrocytes*, CRC Press, Boca Raton, Ann Arbor, Mich., pp. 227–236). Preferred growth factors include, but are not limited to transforming growth factor beta (TGFβ), insulin-like growth factor (IGF), platelet derived growth factor (PDGF), epidermal growth factor (EGF), acidic fibroblast growth factor (aFGF), basic fibroblast growth factor (bFGF), hepatocyte growth factor, (HGF) keratinocyte growth factor (KGF), the bone morphogenic factors (BMPs), for example, BMP-1, BMP-2, BMP-3, BMP-4, BMP-5 and BMP-6, and the osteogenic proteins (OPs), i.e., OP-1, OP-2 and OP-3. Preferred concentrations of TGFβ, IGF, PDGF, EGF, aFGF, bFGF, HGF, and KGF, range from about 1 to 100 ng/ml, more preferably from about 5 to about 50 ng/ml, and most preferably from about 10 to about 20 ng/ml. Preferred concentrations of the BMP's and OP's range from about 1 to about 500 ng/ml, more preferably from about 50 to about 300 ng/ml, and most preferably from about 100 to about 200 ng/ml. However, these particular growth factors are not limiting. Any polypeptide growth factor capable of stimulating or inducing the production of cartilage specific proteoglycans and collagen may be useful according to the invention as provided herein.

Once a mitotically expanded population of chondrocytes is obtained, the cells can be implanted either back into the same subject from which their parent cells were originally derived (autologous implantation), or into a different subject (heterologous implantation). In addition, heterologous implantation may utilize chondrocytes obtained from a related or unrelated individual of the same species (allogeneic), or from a different species (xenogeneic). Alternatively, chondrocytes may be obtained from an established, long-term cell line that is either allogeneic or xenogeneic.

Methods for preparing and using rho-zero and cybrid cells are described in U.S. Pat. Nos. 5,840,493 and 5,888,438, published PCT applications WO 95/26973 and WO 98/17826, King and Attardi (*Science* 246:500–503, 1989), Chomyn et al. (*Mol. Cell. Biol.* 11:2236–2244, 1991), Miller et al. (*J. Neurochem.* 67:1897–1907, 1996), Swerdlow et al. (*Annals of Neurology* 40:663–671, 1996), Cassarino et al. (*Biochim. Biophys. Acta* 1362:77–86, 1997), Swerdlow et al. (*Neurology* 49:918–925, 1997), Sheehan et al. (*J. Neurochem.* 68:1221–1233, 1997) and Sheehan et al. (*J. Neurosci.* 17:4612–4622, 1997). Methods of rapidly obtaining rho-zero cells in relatively short periods of time, which may be desirable in some situations, are described in copending U.S. patent application Ser. Nos. 09/069,489 and 09/301,517.

A kit for identifying a risk for, determining a degree of disease progression of, or stratifying subjects of a vertebrate species according to subtypes of, an arthritic disorder in a biological sample from a vertebrate subject typically contains one or more reagents that permit determination of the level(s) of at least one indicator of altered mitochondrial function as provided herein, and additionally may contain ancillary reagents that are useful to detect an indicator of altered mitochondrial function. As a non-limiting example, to detect an indicator of altered mitochondrial function that is a mitochondrial enzyme catalytic activity, one or more well known calorimetric, spectrophotometric, fluorimetric, immunometric, mass spectrometric or radiometric reagents may be included in the kit, depending on the particular activity to be determined, along with ancillary reagents that facilitate detection of the indicator(s). As another non-limiting example, to detect the production of ATP in a sample, luciferase and its ATP-dependent oxidation substrate D-luciferin may be present in a kit, along with ancillary reagents that facilitate detection of the indicator of altered mitochondrial function as provided herein, for example, a mitochondrial inhibitor the use of which permits determination of ATP produced via anaerobic as compared to aerobic respiration, or a mitochondria protective agent.

As other non-limiting examples, to detect a particular protein that may be an indicator of altered mitochondrial function, the reagent provided in the kit is typically an antibody specific for such protein. Such kits also contain a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

Kits for detecting indicators of altered mitochondrial activity that are enzymes as provided herein thus typically comprise an enzyme substrate in combination with a suitable buffer or other ancillary reagent, which may in certain embodiments include compositions as described herein that relate to mitochondrial activity. For example, enzyme activity may also be specifically detected by performing an immunoprecipitation step with an enzyme-specific antibody prior to performing an enzyme catalytic activity assay as described above. Ancillary reagents may include other reagents that may also be provided in such kits, for example to detect mitochondrial enzyme-mediated modification of a substrate, including but not limited to mitochondrial inhibitors and/or mitochondria protective agents as provided herein.

Accordingly, in other embodiments, kits according to the present invention may comprise at least one reagent for determining an indicator of altered mitochondrial function and at least one ancillary reagent, where those having ordinary skill in the art can readily determine what are suitable reagents for such purposes depending on the particular indicator of altered mitochondrial function to be determined, based on the present disclosure and relevant knowledge in the art.

These and related advantages will be appreciated by those familiar with the art. The following Examples are offered by way of illustration and not limitation.

EXAMPLES

Example 1

Inhibitors of Electron Transport Complex III Inhibit Collagen and Proteoglycan Synthesis in Chondrocytes In order to determine if inhibition of mitochondrial function (specifically, inhibition of electron transport chain complex III) impacts collagen and proteoglycan synthesis by chondrocytes, the following experiments were carried out.

Human articular cartilage chondrocytes were obtained by collagenase digestion of articular cartilage samples, and subsequent monolayer culture, essentially as described by Terkeltaub et al. (*Arthritis Rheum.* 41:2152–2164, 1998). The starting material for these primary cultures was human articular cartilage excised during surgical joint replacement, or obtained at autopsy from normal or osteoarthritic joints. The articular chondrocytes were grown in Dulbecco's modified Eagle's Medium with high glucose (DMEM high glucose, Life Technologies, Inc. Grand Island, N.Y.) with 10% fetal calf serum (FCS), 1% glutamine, 100 U/ml penicillin and 50 $\mu$g/ml streptomycin (all reagents from Sigma, St. Louis, Mo., unless otherwise noted). Typically, only first passage cells were used in the studies described herein.

Immortalized TC28 (a.k.a. "T/C-28") juvenile rib chondrocytes were provided by Dr. Mary Goldring (Harvard Medical School, Boston, Mass.). Another immortalized mammalian cell line that may be used in experiments of this type is the rabbit (*Oryctolagus cuniculus*) cell line HIG-82 (available from the American Type Culture Collection, Manssas, Va., under accession No. CRl-1832). The TC-28 cell line was cultured in DMEM with low glucose/Ham's F-12 (1:1) (Life Technologies, Grand Island, N.Y.) supplemented as described above for articular chondrocytes, and continuously passaged after reaching approximately 90% confluency at a 1:10 split ratio. In some experiments, the chondrocytes were cultured on polyHEMA (polyhydroxyethyl methacrylate) in order to induce a mineralizing phenotype and a three-dimensional configuration of chondrocytes that resembles physiologic chondrocyte architecture (Glowacki et al., *Proc. Soc. Exp. Biol. Med.* 172:93–98, 1983).

The articular chondrocytes and TC28 cells exhibited comparable respiratory properties when the two cell preparations were compared by measuring oxygen consumption with a Clark electrode (Rank Bros. Bottisham, Cambridge, UK) under state 3, state 3/4 and state 3 (uncoupled) conditions (see, e.g., Ernster et al., 1981 *J. Cell Biol.* 91(3 part 2): 227s; Boveris et al., 1973 *Biochem. J.* 134:707; Boveris et al., 1076 *Biochem. J.* 156:435). Articular chondrocytes and TC28 cells displayed markedly inhibited respiratory rates, and depressed intracellular ATP levels, following exposure to either the NO and $O_2$-donor SIN-1 (500 $\mu$M) or the NO donor NOC-12 (250 $\mu$M). The mitochondrial ETC complex III inhibitor antimycin A, and the mitochondrial ATP synthase (complex V) inhibitor oligomycin, also inhibited respiratory rates and depressed intracellular ATP levels in articular chondrocytes and TC28 cells.

Nonlethal but mitochondrial effective doses of antimycin A were determined as follows. Progressively higher concentrations of antimycin A (Sigma Chemical Co., St. Louis, Mo.) were added to cultured articular condrocytes and TC-28 cells. Cell proliferation was measured by incorporation of fluorogenic H33258 (Calbiochem, La Jolla, Calif.) essentially according to the manufacturer's instructions, and cell viability was assessed by trypan blue dye exclusion (Medzihradsky et al., *Biochem. Med.* 13:164–177, 1975), essentially according to the instructions of the manufacturer (Sigma).

Levels of total cellular ATP were measured by a modification of luciferase-based assays known in the art (Lin et al., *Anal. Biochem.* 24:531–540, 1968); related assays and modifications may alternatively be used (see, e.g., Turman et al., *In Vitro Cell. Dev. Biol. Anim.* 32:1–4, 1996, for an assay format that uses a fluorescent plate reader). In brief, $2\times10^6$ cells were washed and pelleted in 10 ml phosphate-buffered saline (PBS). The cell pellets were snap-frozen in a dry ice/ethanol bath, after which 0.25 $\mu$l of 0.2 M HCl was added, followed by 0.3 ml of 2 mM glycine (pH 9.0). Samples were heated at 100° C. for five minutes, then placed on ice. A standard curve was developed using 0 to 500 pmol of purified ATP (disodium salt). One hundred (100) $\mu$l of the cell extract, or purified ATP standard, was added to an equal volume of the ATP assay mixture (containing $MgSO_4$, DTT, EDTA, luciferase and luciferin, all from the Sigma Bioluminescence Assay Kit and all diluted 1:25). Following a 5 second incubation and 15 second integration, samples were read on a TD-20/20 Luminometer (Turner Designs, Sunnyvale, Calif.).

Figure 1B:
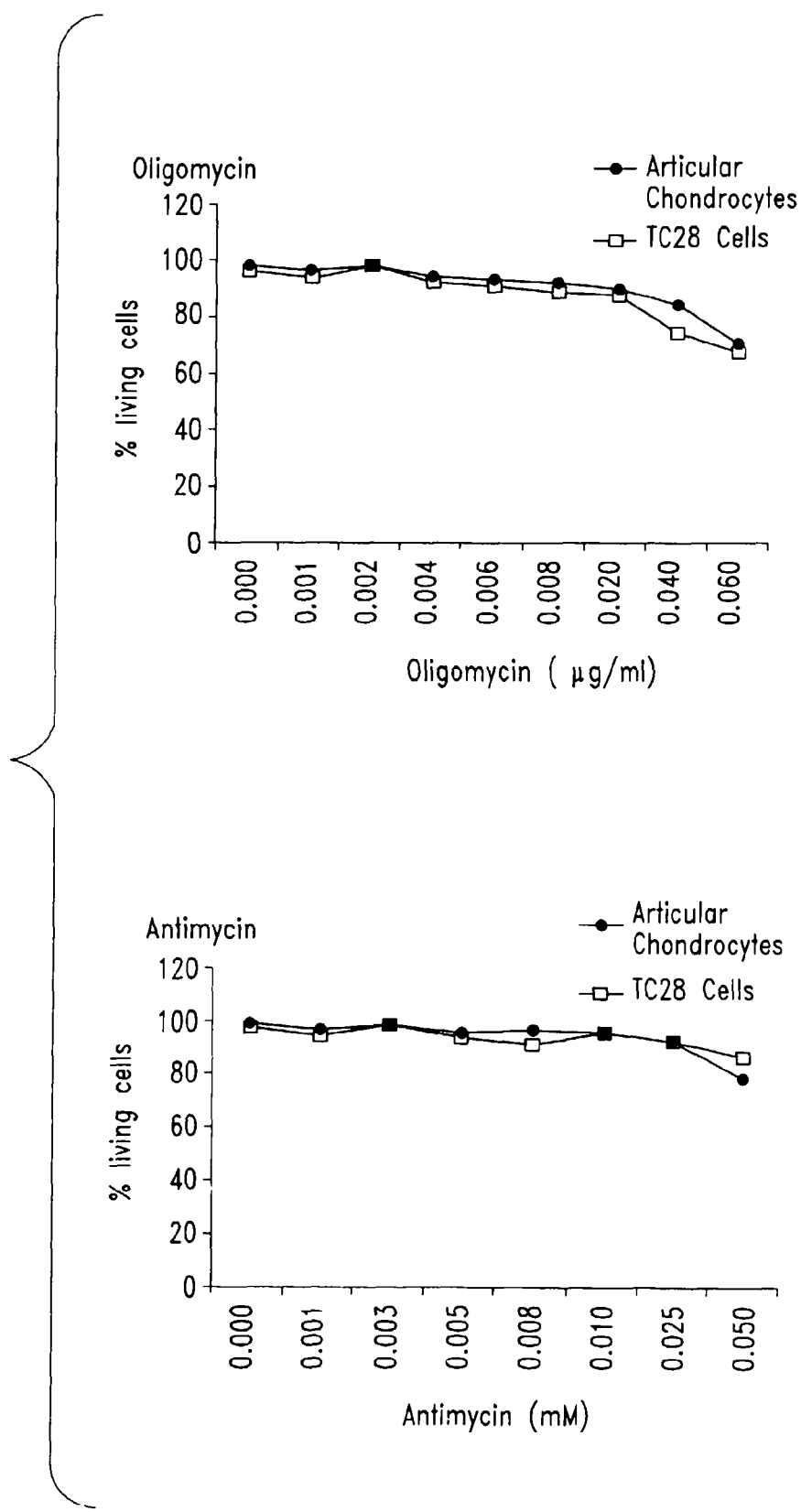

The objective of these studies was to find, if possible, a level of antimycin A that depressed total cellular ATP levels without causing more than 10% loss of viability. The results are shown in FIG. 1. In FIG. 1A, articular chondrocytes or TC28 cells ($5\times10^5$) in 5 ml were studied in triplicate in the presence of antimycin (or oligomycin, see next Example) at the indicated concentrations, administered every 24 hours for a total of 72 hours, and total intracellular ATP concentrations were determined as described above. Viability determinations are shown in FIG. 1B, where $2\times10^4$ chondrocytes or TC28 cells in 0.2 ml were cultured in triplicate in the presence of antimycin (or oligomycin) at the indicated concentrations, administered every 24 hours for a total of 72 hours, and cell viability was determined by trypan blue dye exclusion (>200 cells counted for each replicate). Essentially identical results (not shown) were obtained using the Promega (Madison, Wis.) lactate dehydrogenase release assay kit according to the supplier's instructions.

These studies demonstrated that 0.025 mM antimycin A depleted intracellular ATP levels by 50–80% with less than 10% loss of viability and without altering the constitutively high level of glycolysis. Unless otherwise indicated, this selected concentration of antimycin A was employed in all further experiments.

Figure 2:
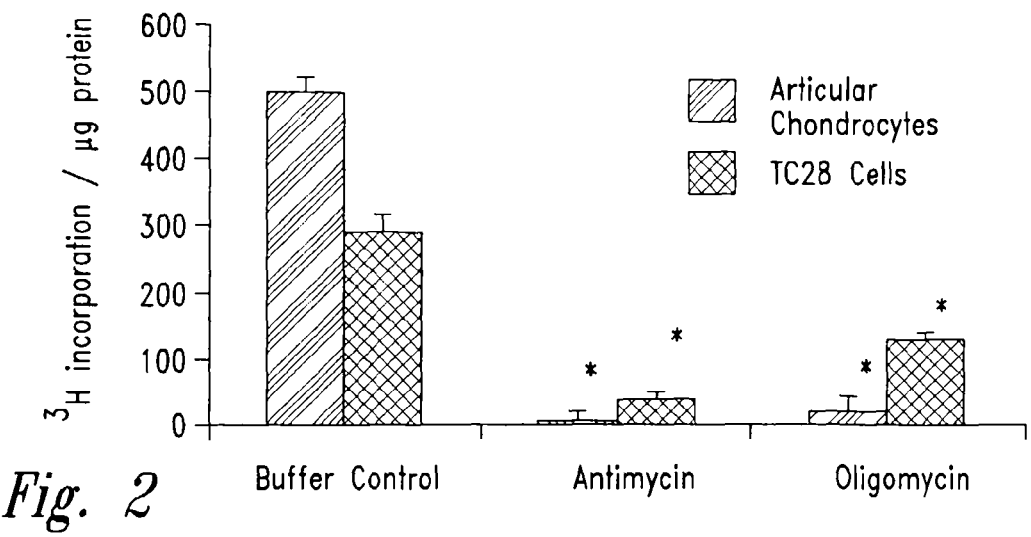
FIG. 2 shows effects of mitochondrial inhibitors on collagen synthesis by cultured chondrocytes.

Collagen production was measured by tritiated proline ([$^3$H]-proline) biosynthetic protein labeling and measuring of collagenase-sensitive protein production (FIG. 2). Articular chondrocytres or TC28 cells ($5 \times 10^5$ cells) were plated in 5 ml medium made 0.025 mM in antimycin A (or 0.02 µg/ml oligomycin, see next Example) by addition of the indicated agent every 24 hours. After the mitochondrial inhibitors were added, the cells were cultured for a further 48 hours. Medium was then removed and replaced with serum-free medium containing 5 µl/ml of [$^3$H]-proline, 50 µg/ml ascorbate and 100 µg/ml β-aminoproprionitrile, and incubation continued for an additional 8 hours.

Medium was then collected and precipitated with 15% trichloroacetic acid (TCA). Cells were extracted in 1 M NaCl, 1 mM N-ethylmaleimide, 0.2 mM phenylmethylsulfonyl fluoride, 0.75 mM EDTA and then precipitated with 15% TCA. The precipitates were washed 3 times with 5% TCA and once with 5% TCA containing 0.5% tannic acid. The pellet was dissolved and resuspended in 0.05 M Tris-HCl, pH 7.6, 5 mM CaCl$_2$, 2.5 mM N-ethylmaleimide. Collagenase-sensitive protein per µg total protein was determined by incubation for 2 hours with 80 units/ml of collagenase, followed by addition of 10% TCA/0.5% tannic acid, and addition of the supernatant to scintillation fluid for standard scintillation counting in the tritium channel.

Figure 3A:
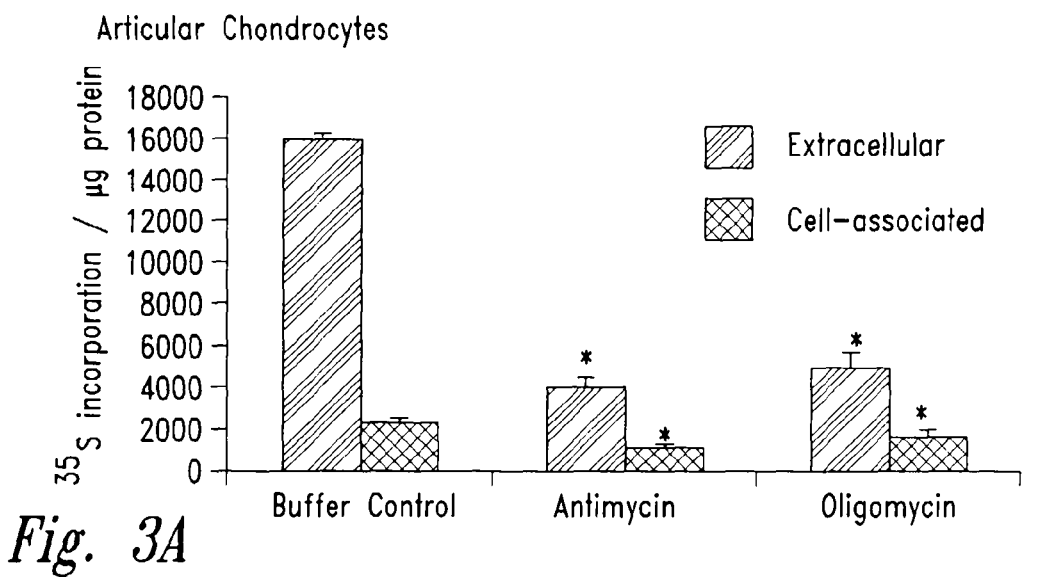
FIG. 3 shows effects of mitochondrial inhibitors on proteoglycan synthesis by cultured chondrocytes (FIG. 3A) and TC28 cells (FIG. 3B).
Figure 3B:
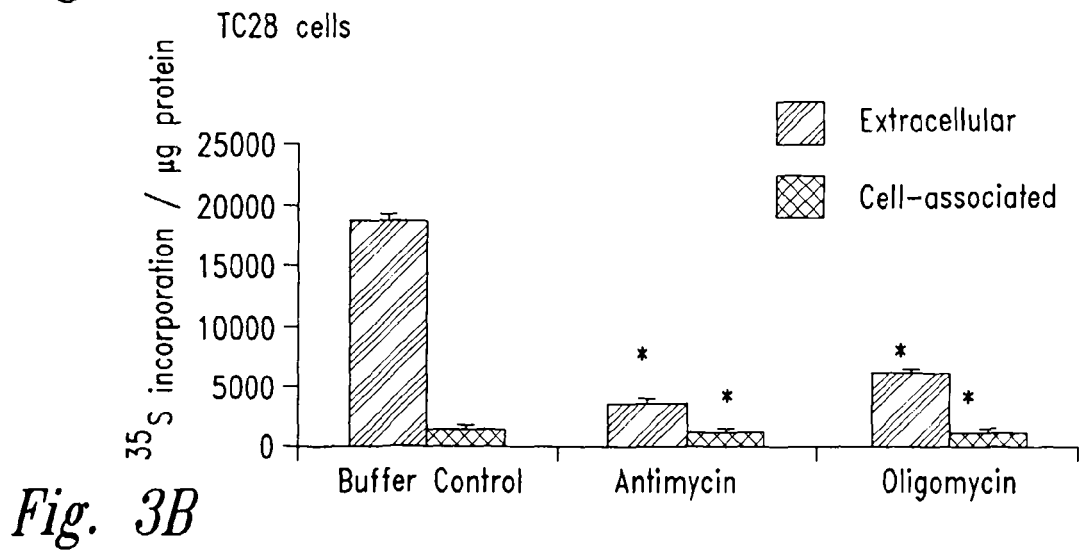

Proteoglycan synthesis was measured by [$^{35}$S]-labeling and uptake of the isotope, as well as by biosynthetic incorporation of the isotope (van Osch et al., Matrix Biol. 17:413–424, 1998) into proteoglycans extracted and subsequently purified by column chromatography on Sephadex® G-25 (Pharmacia, Piscataway, N.J.) (FIG. 3). Chondrocytes or TC28 cells ($3 \times 10^6$) were plated in 30 ml of medium in a 10-cm diameter tissue culture dish and the medium was made 0.025 mM in antimycin (or 0.02 µg/ml oligomycin) every 24 hours for 72 hours. After 48 hours of culture, 20 µCi/ml of [$^{35}$S]sodium sulfate was added to each plate in serum-free medium. After a total of 72 hours, the medium was collected and the cells were washed once with phosphate buffered saline (PBS) and then scraped into 0.5 M NaOH and mixed for 48 hours at 4° C. The medium and the cell extract were eluted from Sephadex® (Pharmacia, Piscataway, N.J.) G-25M PD-10 columns with 4M guanidine-HCl. The eluted portion was added to scintillation fluid and counted (n=9 replicates in FIG. 3; *=P<0.05 by Student's t-test). The results of these experiments (FIGS. 2 and 3) showed that 72 hours after antimycin A addition, the synthesis of both collagen and proteoglycan was depressed by more than about 50% in chondrocytes.

Example 2

Inhibitors of Electron Transport Complex V Inhibit Collagen and Proteoglycan Synthesis in Chondrocytes In order to confirm that inhibition of mitochondrial function generally impacted collagen and proteoglycan synthesis by chondrocytes, as contrasted with a mechanism by which antimycin A specifically or directly depressed these functions, the following experiments were carried out with oligomycin, which acts to inhibit the electron transport chain at a different target (complex V) than antimycin A (complex III).

Chondrocytes were prepared and cultured as in the previous Example and treated with progressively higher concentrations of oligomycin (all reagents in these Examples were from Sigma, St. Louis, Mo., unless otherwise noted). Mitochondrial and cellular functions were assayed in order to determine a level of oligomycin that met the same criteria as those established in the preceding Example for antimycin A (i.e., that depressed total cellular ATP levels without causing more than 10% loss of viability). As shown in FIG. 1, 0.02 µM oligomycin depleted intracellular ATP levels by 50–80% with less than 10% loss of viability, and without altering the constitutively high level of glycolysis. Unless otherwise indicated, this selected concentration of oligomycin (0.02 µM) was employed in all further experiments.

In addition to determining the effects of oligomycin on ATP levels and cell viability, the influences of oligomycin on collagen biosynthesis (FIG. 2) and on proteoglycan production (FIG. 3) by chondrocytes were measured, according to the methodologies described in the preceding example. As was determined with antimycin A, a non-lethal dose of oligomycin depressed the synthesis of both collagen and proteoglycan by more than about 50% in chondrocytes 72 hours after addition of the mitochondrial function inhibitor.

In sum and according to non-limiting theory, the results presented in Examples 1 and 2 suggested that impairment of mitochondrial function, which would be expected to occur in some aging chondrocytes, contributed to observed decreases in the synthesis of several extracellular matrix components. Such decreased levels of synthesis of matrix components are hallmarks of arthritic disorders such as OA, RA, DJD and the like.

Example 3

Inhibitors of Electron Transport Block the Ability of TGFβ to Stimulate Chondrocyte Functions Transforming growth factor beta (TGFβ) is characterized by its potent and widespread actions, which may be used to distinguish it from a number of other known growth factors (for a review, see, e.g., Clark et al., Int. J. Biochem. Cell. Biol. 30:293–298, 1998; Alevizopoulos et al., Bioessays 19:581–591, 1997; and Massagu, Annu. Rev. Biochem. 67:753–791, 1998). It has been suggested that TGFβ plays an important role in the repair potentiality of joint cartilage, especially in arthritis (Pujol et al., Ann. Endocrinol. 55:109–120, 1994). High concentrations of TGFβ have been found in synovial fluid from arthritic joints (van Beuningen et al., Lab. Invest. 71:279–290, 1994). TGFβ stimulates synthesis of extracellular matrix components such as collagen, fibronectin and proteoglycan (Roberts et al., Kidney Intl. 41:557–559, 1992), and suppresses proteoglycan degradation in vitro. Moreover, TGFβ may be unique among chondrocyte growth factors in causing a marked increase in PPi elaboration, particularly in chondrocytes from older individuals (Rosen et al., *Arthritis Rheum.* 40:1275–1281, 1997).

Chondrocytes (primary cultures and immortalized cell line TC-28) were prepared and cultured as in the preceding Examples, with the exception that TGFβ was present (at 10 ng/ml) in some samples throughout the 0 to 72 hour time frame. The TGFβ used in the experiments described herein was purchased from R&D Systems (Minneapolis, Minn.; TGFβ is also available from other sources, e.g., Sigma, St. Louis, Mo.; or Research Diagnostics, Inc., Flanders, N.J.). Briefly, articular chondrocytres or TC28 cells ($5 \times 10^5$ cells) were cultured in 5 ml of complete medium and treated with 10 ng/ml TGFβ, 0.025 mM antimycin A, or 0.02 µg/ml oligomycin. The cells were incubated at 37° C. for 48 hours, with antimycin and oligomycin replenished after the first 24 hours. The cells were then washed with phosphate buffered saline, frozen on dry ice, and assayed for intracellular ATP as described in Example 1.

The results of these experiments, as presented in Table 1, indicated that TGFα treatment increased intracellular ATP about 3-fold in the chondrocytes, when assessed 72 hours after treatment. However, when antimycin A (0.025 mM) or oligomycin (0.02 µM) were additionally present, this effect was blocked. These results suggest that healthy mitochondrial function was needed for TGFβ to have its effects on chondrocytes.

TABLE 1

| Condition | ATP (pmoles/µg DNA): Articular Chondrocytes | ATP (pmoles/µg DNA):TC28 cells |
|---|---|---|
| Buffer control | 435.2 ± 4.2 | 393.8 ± 29.8 |
| Oligomycin | 221.2 ± 14.0* | 198.6 ± 3.7* |
| TGFβ | 1,158 ± 6.9* | 801.6 ± 4.9* |
| Oligomycin + TGFβ | 398.3 ± 3.6 | 369.6 ± 5.0 |
| Antimycin | 93.73 ± 5.9* | 69.78 ± 4.0* |
| Antimycin + TGFβ | 456.6 ± 9.6 | 299.6 ± 2.0 |
| *P < 0.01 vs. control (Student's t-test) | Data presented as mean ± SD | |

Example 4

Inhibitors of Mitochondrial Function Inhibit the Production and Elaboration of Inorganic Pyrophosphate (PPI)

Chondrocytes are relatively unique in terms of their ability to elaborate large amounts of inorganic pyrophosphate (PPi). PPi critically regulates both apatite and calcium pyrophosphate dihydrate (CPPD) deposition in osteoarthritis.

A key PPi-producing ecto-enzyme produced by chondrocytes is the plasma cell membrane glycoprotein-1 (PC-1). PC-1 is a 5'-nucleotide phosphodiesterase I (EC 3.1.4.1), as well as a nucleotide pyrophosphohydrolase (EC 3.6.1.9), and is thus referred to herein as NTPPPH PC-1. ATP is a substrate for NTPPPH PC-1. That is, in addition to being a source of biochemical energy for cells, ATP may be a critical source of PPi. In order to determine the role of mitochondrially-produced ATP in PPi elaboration, the following experiments were carried out.

Figure 4A:
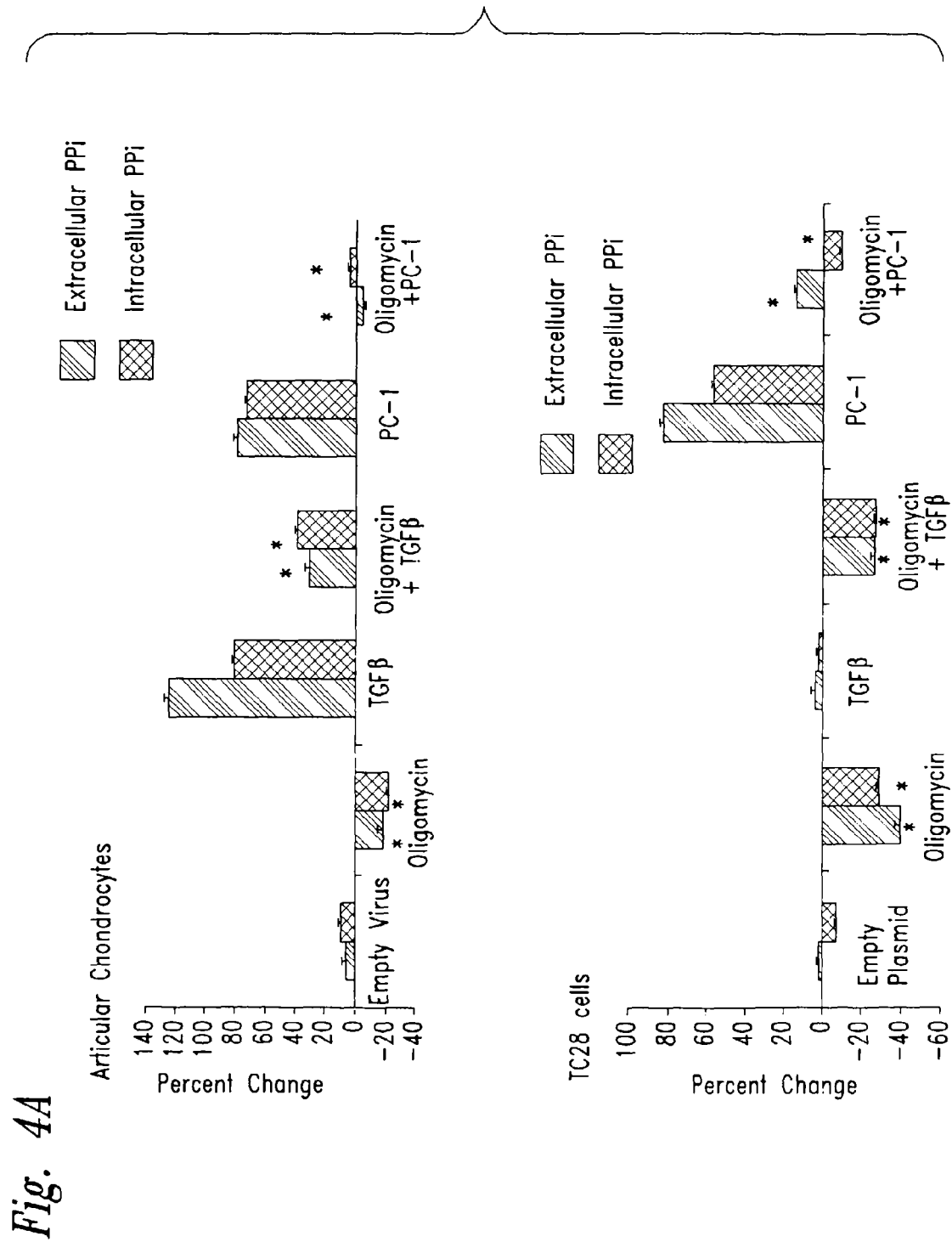
FIGS. 4A and 4B show effects of mitochondrial inhibitors on inorganic pyrophosphate (Ppi) elaboration by cultured chondrocytes.
Figure 4B:
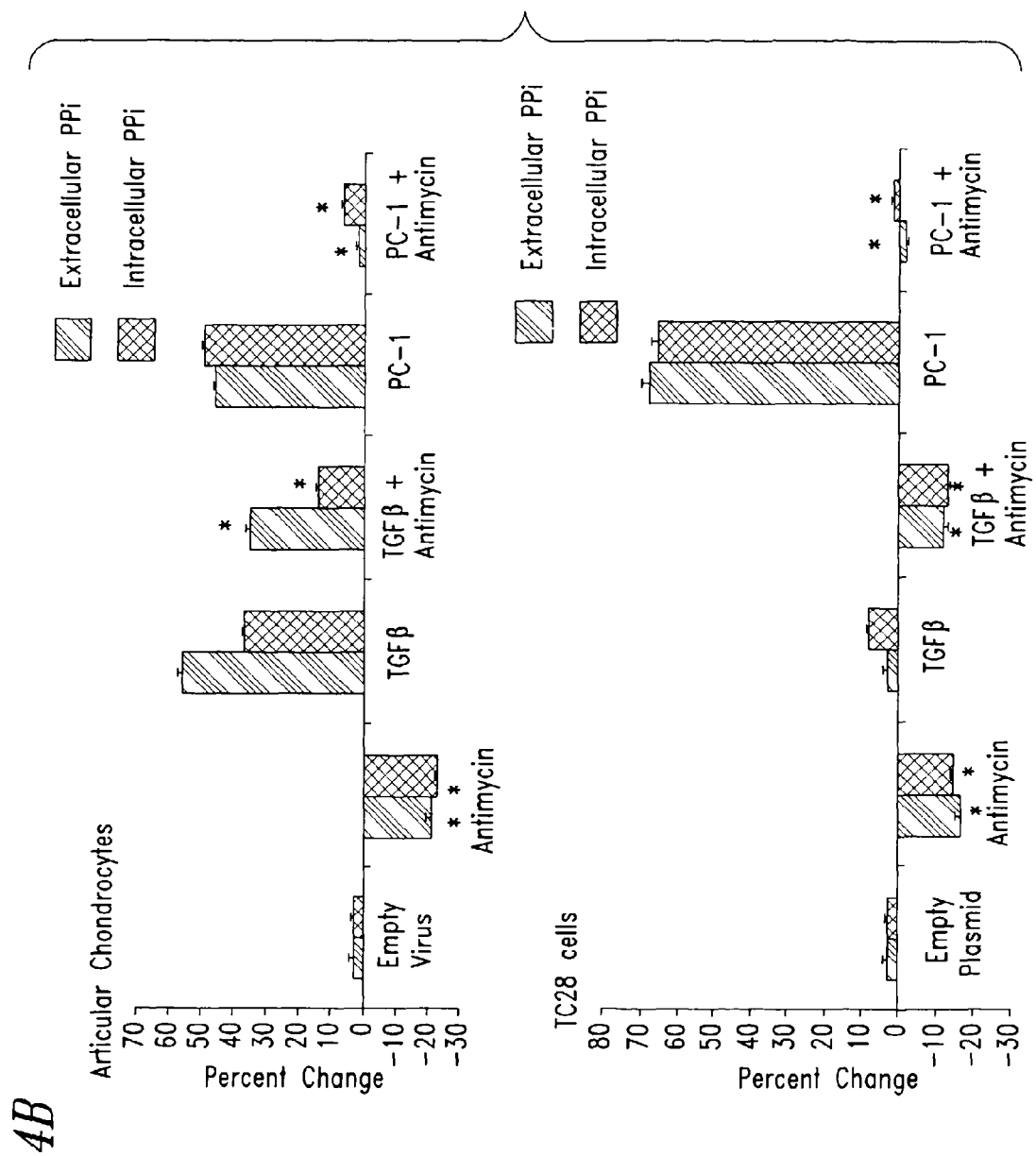

One set of experiments described in this Example and presented in FIG. 4 examined the effects of agents that inhibit mitochondrial function on PPi elaboration in the absence of TGFβ. Chondrocytes (primary cultures and immortalized cell line TC-28) were prepared, cultured and treated with oligomycin (FIG. 4A), or with antimycin A (FIG. 4B), as in the preceding Examples. Extracellular PPi was determined radiometrically, and equalized for cellular DNA, according to the method of Terkeltaub et al. (Arthritis Rheum. 41:2152–2164, 1998). To determine intracellular PPi levels, washed cells were heated at 65° C. for 45 minutes, washed again and lysed in lysis buffer (1% Triton X-100, 1.6 mM MgCl2, 0.2 M Tris, pH 8.1), essentially according to the procedures described by Lotz et al. (Proc. Natl. Acad. Sci. U.S.A. 92:10364–10368, 1995). The results of these studies show that these inhibitors of mitochondrial function attenuated basal PPi elaboration (FIG. 4).

Another set of experiments examined the ability of inhibitors of mitochondrial function to impact the ability of TGFβ to increase intracellular and extracellular PPi levels. Antimycin A- (FIG. 4B) or oligomycin-treated (FIG. 4A) chondrocytes, as well as control (untreated) cells, prepared as described in the preceding Examples, were incubated with or without TGFβ (10 ng/ml), and levels of extracellular and intracellular PPi levels were determined. Inhibition of mitochondrial function by either antimycin A or oligomycin abrogated the ability of TGFβ to increase extracellular and intracellular PPi (FIG. 4).

In related experiments, the effects on PPi elaboration by PC-1 transfectants of either oligomycin or antimycin A, alone or in combination with TGFβ, were determined (FIG. 4). Briefly, transient transfections were performed on $5 \times 10^5$ TC28 cells in a 35 mm tissue culture dish using Lipofectamine Plus™ (Life Technologies, Grand Island, N.Y.). Empty plasmid DNA (2 µg) or wild-type human PC-1-encoding DNA in plasmid pcDNA3.1 (2 µg) (Johnson et al., 1999 *Arth. Rheum.* 42:1986; Terkeltaub et al., 1994 Arthritis Rheum. 37:934–41) was added to the lipid reagent following a complex formation of the DNA to the "Plus" reagent according to the supplier's instructions, and then incubated with cells for 3 hours at 37° C. in DMEM/Fi2 medium containing 1% FCS. Cells were then washed with phosphate buffered saline (PBS), returned to complete culture medium and incubated an additional 72 hours. Adenoviral gene constructs comprising nucleotide sequences encoding TGFβ-inducible NTPPPH PC-1 have also been described, and have been shown to elaborate increased levels of PPi (Johnson et al., J. Bone Miner. Res. 14:883–892, 1999). For adenoviral gene transfer, the protocol of Johnson et al. was followed (1999 *Arth. Rheum.* 42:1986) using articular chondrocytes which, unlike TC28 cells, cannot be efficiently transfected with plasmid DNA. Transiently transfected TC28 cells or adenoviral chondrocyte transformants comprising these adenoviral NTPPPH PC-1 constructs were, however, unable to increase intracellular and extracellular PPi levels in the presence of antimycin A or oligomycin (FIG. 4). In sum, mitochondrial function, particularly oxidative phosphorylation, appeared to provide ATP that was critical for extracellular matrix synthesis and PPi elaboration in chondrocytes.

Example 5

Inhibitors of Mitochondrial Function Enhance the Pathological Deposition of Calcium by Matrix Vesicles In arthritic disorders such as osteoarthritis, matrix vesicles (MVs) mediate the pathological deposition of calcium (Anderson, *Rheum. Dis. Clin. North Am.* 14:303319, 1988; Doyle, J. Pathol. 136:199–216, 1982; Doherty, *Hosp. Pract. Off Ed.* 29:93–104, 1994). In order to determine the mitochondrial component, if any, of pathological calcium deposition, the following experiments were carried out.

Nodule-forming chondrocytes were cultured on poly-HEMA (polyhydroxyethyl methacrylate)—coated tissue culture flasks (Nalg Nunc International Corp., Rochester, N.Y.) and treated with antimycin A or oligomycin using dosages and kinetics determined as described above; control samples were handled in the same manner but were not exposed to these inhibitors of mitochondrial function. Matrix vesicles were prepared essentially according to previously described procedures (Johnson et al., *J. Bone Miner. Res.* 14:883–892, 1999). In brief, media were collected and initially centrifuged at 20,000×g for 20 minutes at 4° C. to pellet cellular debris, followed by centrifugation at 100,000×g for 1 hour to isolate the MV fraction. The MVs were resuspended in 0.4 ml of lysis buffer (1% Triton X-100 in 0.2 M Tris base with 1.6 mM $MgCl_2$, pH 8.1).

The capacity of the MVs to mediate calcium deposition was assayed essentially according to previously described procedures (Johnson et al., *J. Bone Miner. Res.* 14:883–892, 1999). MV fractions (about 0.04 mg of protein in 0.025 ml) were added to 0.5 ml of calcifying medium (2.2 mM $CaCl_2$ [1 µCi/ml of $^{45}Ca$], 1.6 mM $KH_2PO_4$, 1 mM ATP disodium salt, 1 mM $MgCl_2$, 85 mM NaCl, 15 mM KCl, 10 mM $NaHCO_3$, 50 mM N-Tris (hydroxymethyl) methyl 2-aminoethanesulfonic acid, pH 7.6) and vortexed and incubated at 37° C. for 24 hours. The samples were then centrifuged at 14,000×g for 10 minutes at 4° C. The pellets were washed twice with cold (nonradiolabeled) calcifying medium that lacked ATP. The $^{45}Ca$ in the mineral phase was solubilized in HCl and counted in 5 ml of scintillation fluid. Assay controls included the omission of ATP from the calcifying media and/or heat inactivation (60° C. for 30 minutes) of the MVs.

Figure 5:
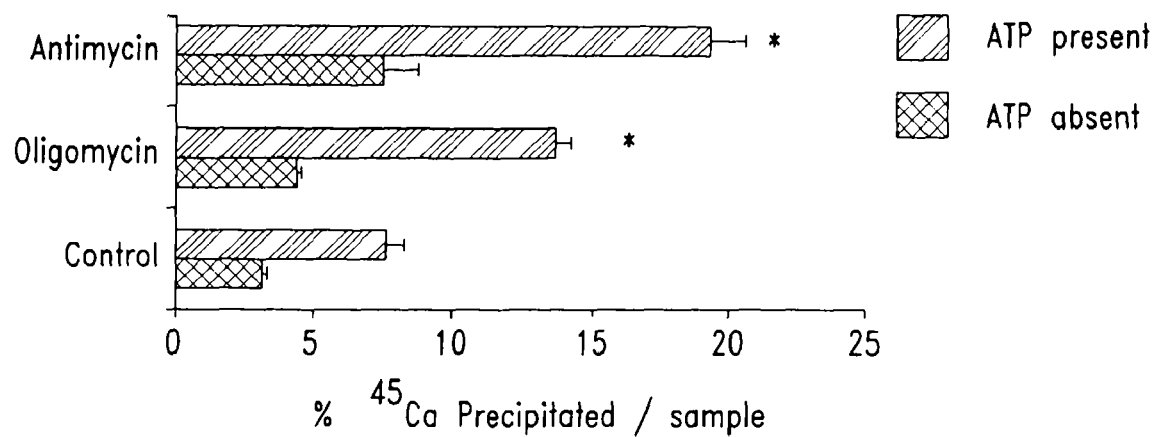
FIG. 5 shows the effects of mitochondrial inhibitors on matrix vesicle (MV)-mediated mineralization.

The results of these experiments (FIG. 5) demonstrated that ATP-treated MV derived from chondrocytes precipitated >50% more $^{45}Ca$ ($p<0.01$) when prepared from cells treated with antimycin A or oligomycin as compared to control (untreated) cells. Control studies showed that neither oligomycin nor antimycin treatment suppressed cell-associated NTPPPH activity, and neither agent altered PPi-degrading alkaline phosphatase activity (not shown). These results indicated that mitochondrial functions, including oxidative phosphorylation, modulate the composition and mineralizing activity of matrix vesicles.

Example 6

Screening Assays for Agents that Protect Chondrocytes Following Induction of Mitochondrial Stress This example describes screening assays using defined chondrocyte functions, for identifying agents that protect chondrocytes from mitochondrial stressors, such as energy depletion or reactive free radicals. Chondrocytic TC28 cells were maintained at 37° C., 5% $CO_2$ in monolayer culture in DMEM/Ham's F12 medium (1:1) supplemented with 10% FCS, 1% L-glutamine, 100 U/ml penicillin and 50 mg/ml streptomycin (Omega Scientific, Tarzana, Calif.). To more closely approximate the in vivo physiologic nonadherent state of chondrocytes for monitoring GAG release (FIG. 10), an in vitro culture system was used wherein TC28 cells were transferred to 6-well plates that had been previously coated for 18 hours at 22° C. with the cell adhesion inhibitor poly-2-hydroxymethacrylate (polyHEMA), provided as a 10% (w/v) solution in 95% ethanol, then washed twice with PBS. Complete medium (DMEM/F12 supplemented as described above) was then added to wells, and cells were maintained under these conditions for up to 72 hours (Folkman et al., 1978 *Nature* 273:345; Reginato et al., 1994 *Arthritis Rheum.* 37:1338). Maintenance of chondrocyte phenotype was confirmed by RT-PCR determination of gene transcripts encoding the chondrocyte extracellular matrix components type II collagen and aggrecan (Reginato et al., 1994).

Cells were exposed to one of several agonists added to cultures as stressors for 72 hours, in the absence or presence of candidate chondrocyte protective agents (listed in Table 2). According to non-limiting theory, such stressors may act as one or more of a mitochondrial inhibitor, an inducer of altered mitochondrial function, an apoptogen, an energy-depleting agent, or the like. Stressors used in this example included the nitric acid donor NOC-12 (N-ethyl-2-(1-ethyl-2-hydroxy-2-nitrosohydrazino)ethanamine; Calbiochem, La Jolla, Calif.); the peroxynitrite donor SIN-1 (3-morpholinosydnonimine, HCl; Calbiochem); and the inflammatory cytokine human recombinant interleukin-1 beta (IL-1β, Calbiochem). Cytotoxicity was determined using the lactate dehydrogenase release assay (Promega, Madison, Wis.) as described above and according to the manufacturer's instructions, and chondrocyte intracellular ATP was determined using the luciferase assay as described above in Example 1.

TABLE 2

Candidate Chondrocyte Protective Compounds

| COMPOUND | STRUCTURE | Synthesis Reference (Compound #) |
|---|---|---|
| A | (structure: 2-methyl-4-hydroxyphenyl guanidine derivative) | WO 99/55321 # 30 |

TABLE 2-continued

Candidate Chondrocyte Protective Compounds

| COMPOUND | STRUCTURE | Synthesis Reference (Compound #) |
|---|---|---|
| B | (2-iminoimidazolidin-1-yl)acetic acid | WO 99/55321 |
| C | N-methyl-N-carbamimidoyl-glycine | WO 99/55321 |
| D | aminoguanidine HCl | WO 99/55321 |
| E | 1-(4-morpholinophenyl)guanidine | WO 99/55321 # 27 |
| F | 1-(2-hydroxybenzyl)aminoguanidine | WO 99/55321 # 26 |
| G | 6-ethoxy-2,2,4-trimethyl-1-(2-(4-isobutylphenyl)propanoyl)-1,2-dihydroquinoline | WO 99/37294 (#III-8) |

TABLE 2-continued

Candidate Chondrocyte Protective Compounds

| COMPOUND | STRUCTURE | Synthesis Reference (Compound #) |
| --- | --- | --- |
| H | [structure] | WO 99/37294 (#III-7) |
| J | [structure] | WO 99/37294 (#IV-9) |
| K | [structure] | WO 99/37294 (#II-6) |
| L | [structure] | WO 99/37294 (#II-9) |

Glycosaminoglycan (GAG) release is widely believed to be a cardinal event in the pathogenesis of osteoarthritis, and is stimulated by IL-1β (see, e.g., Sztrolovics et al., 1999 *Biochem. J.* 339:571 and references cited therein). Therefore, GAG release was determined in chondrocytes maintained on polyHEMA-coated plates as follows: Chondrocyte cartilage "nodules" from the polyHEMA cultures were digested for one hour with papain, 300 μg/ml in 20 mM sodium phosphate-pH 6.8, 1 mM EDTA, 2 mM dithiothreitol. Released GAG was assayed colorimetrically by dimethylene blue (DMB) dye binding according to established procedures (Farndale et al., 1986 *Biochim. Biophys. Acta* 883:173; Sztrolovics et al., 1999 *Biochem. J.* 339:571). Briefly, aliquots of the papain digest were added to a dye solution containing 46 μM DMB, 40 mM glycine-pH 3.0, 40 mM NaCl and read immediately in a spectrophotometer at 525 nm. Quantification of GAG in the samples was achieved from calculations using a standard curve generated with samples of 1–50 μg/ml chondroitin sulfate. Mitochondrial protecting agents based on derivatized creatine, ethoxyquin and guanidine compounds were synthesized essentially as disclosed in WO99/37294 (PCT/US99/01718) and WO99/55321 (PCT/US99/09990), which are hereby incorporated by reference in their entireties; these agents were tested as representative candidate chondrocyte protective agents.

Figure 6:
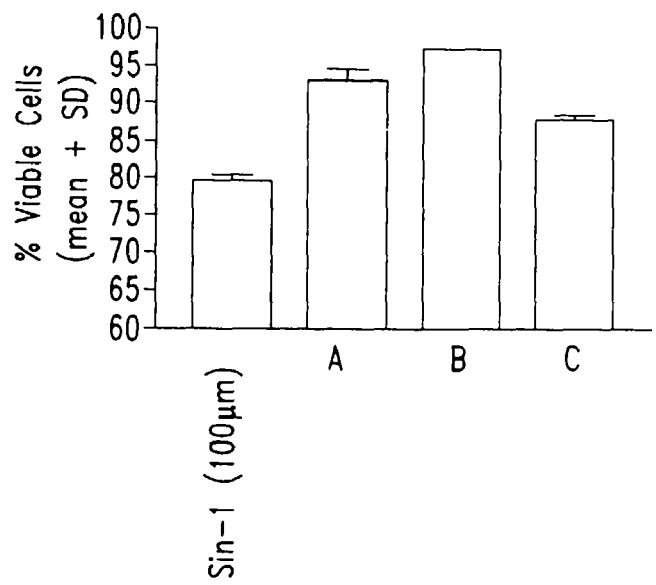
FIG. 6 shows viability of TC28 cells in the presence of SIN-1, a NO donor.
Figure 7:
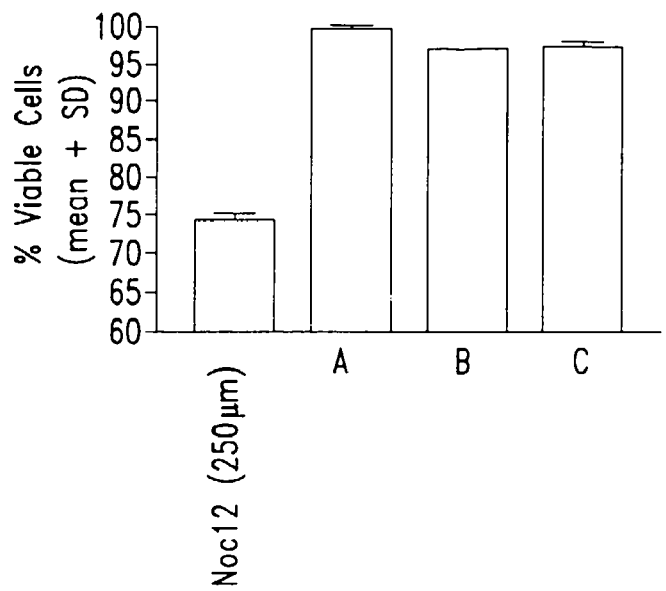
FIG. 7 shows viability of TC28 cells in the presence of NOC-12, a NO donor.
Figure 8:
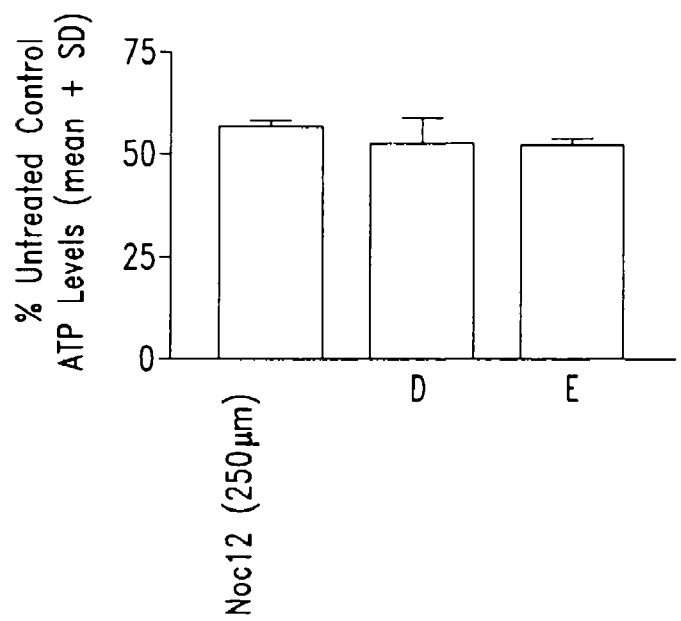
FIG. 8 show TC28 intracellular ATP levels in the presence of NOC-12, a NO donor.
Figure 9:
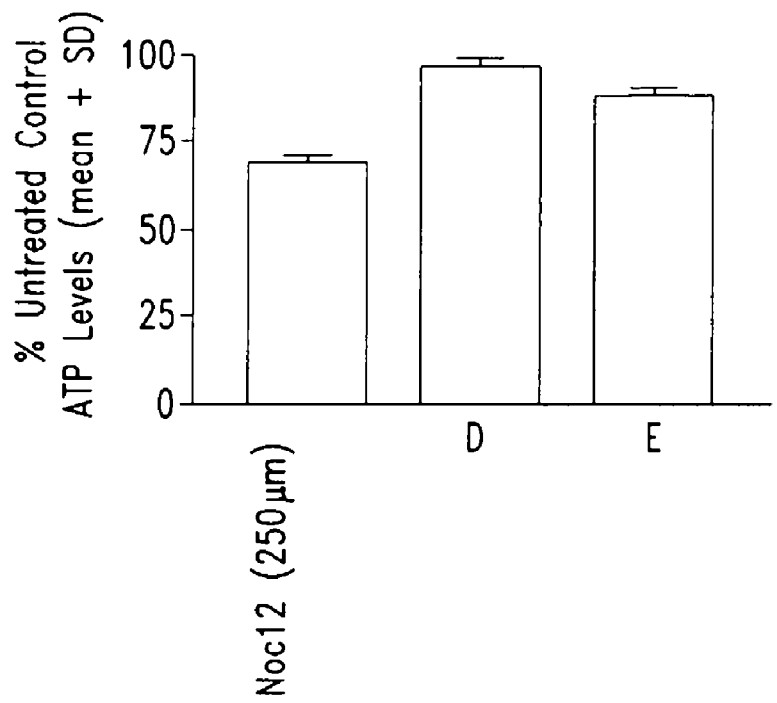
FIG. 9 shows viability of TC28 cells in the presence of NOC-12, a NO donor.

FIG. 6 shows the protective effect on cell viability (by LDH release) conferred by compounds A, B or C (each at 1 μM) on TC28 chondrocytes exposed to the NO and $O_2^-$ donor 100 μM SIN-1. Similar results (i.e., a moderating effect of the test compounds on NO cytotoxicity) are shown in FIG. 7, where TC28 cells were exposed to the NO donor NOC-12 (250 μM) alone or in the presence of 1 μM of compounds A, B or C. FIGS. 8 and 9 show, respectively, intracellular ATP levels and cell viability of TC28 cells cultured with the NO donor NOC-12 alone or in the presence of 1 µM of compounds D or E. In FIG. 8, intracellular ATP levels are depicted relative to the corresponding control culture that was not exposed to NOC-12, and each NOC-12-treated group displayed significant depression of intracellular ATP regardless of the presence or absence of a candidate protective compound. FIG. 9 shows, however, that despite the decreased intracellular ATP concentrations, significantly higher viability characterized the cells maintained in the presence of either one of the protective compounds. At comparable concentrations (each at 1 µM), compounds J, K and L also demonstrated chondrocyte protective activity in cell viability determinations of cells exposed to SIN-1 or NOC-12.

Figure 10:
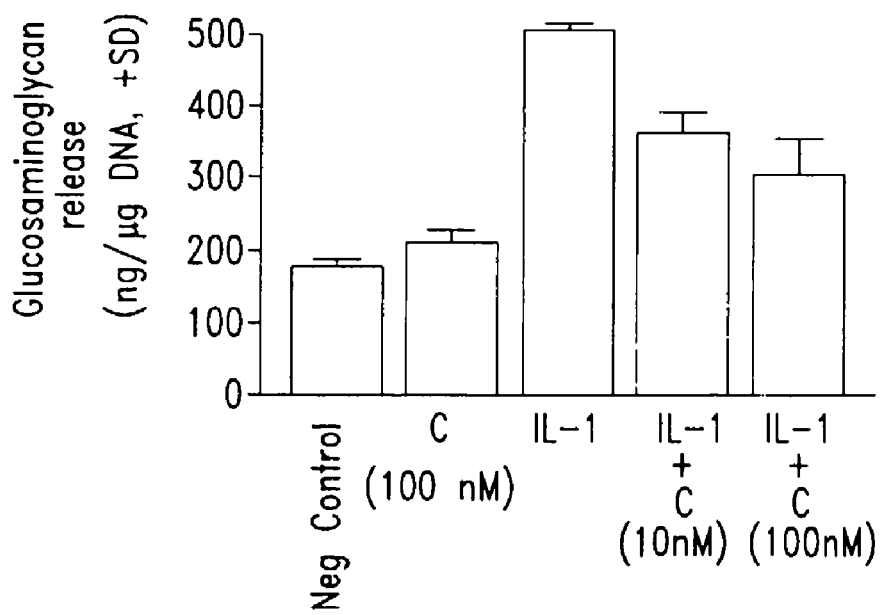
FIG. 10 shows IL-1 stimulated GAG release by TC28 cells.

FIG. 10 shows quantification of IL-1β-stimulated GAG release by TC28 cells cultured as nodules on polyHEMA-coated plates. As also shown in FIG. 10, the inclusion of compound C somewhat attenuated the degree of GAG release. TC28 nodules exposed to SIN-1 (100 µM) or NOC-12 (25 µM) also released GAG, and the severity of this release was moderated when 1 µM compound C was present (not shown). I1–1β did not cause a decrease in intracellular ATP levels or in viability of TC28 cells.

Example 7

Autologous Chondrocyte Implantation (ACI)

Unlike most tissues, articular cartilage has a limited ability to heal; that is, once damaged, it does not normally regenerate itself. Some patients with cartilage damage undergo arthroscopic surgery to relieve their symptoms. Such surgical procedures include those that smooth the surface of the damaged area (e.g., debridement and lavage) and a number of techniques (microfracture, drilling, abrasion arthroplasty) that create fibrous or scar tissue. Although the scar tissue does cover the joint surface, it is less durable and resilient than normal articular (hyaline) cartilage.

The benefits of such surgical procedures decrease over time, especially if the patient's pre-injury activity level is maintained. Symptoms often recur, leaving patients to face the options of living with pain, undertaking another surgical procedure or, in severe cases, undergoing a total joint replacement with an artificial (e.g., knee) prosthesis. Approximately 200,000 total knee replacement operations are performed annually in the United States at a cost of about $25,000 to $30,000 per total knee replacement. In addition to its cost, another disadvantage of the artificial joint is that it generally lasts only 10 to 15 years and is considered a poor treatment option for people under the age of fifty.

The poor long term clinical results of existing treatment options has stimulated researchers to discover and develop alternative treatments for joint damage caused by arthritis, degenerative bone disorders and physical trauma. As detailed in this Example, the present invention provides for such alternative treatments.

A. Background

Efforts have been undertaken to treat patients suffering from damaged cartilage by implanting chondrocytes at the affected site, with the expectation that the implanted cells will facilitate repair of the injury by enhancing the production and deposition of extracellular matrix components. In such efforts, chondrocytes are obtained from a biological source, the chondrocytes are mitotically expanded to generate a cell population which is then surgically implanted into the injured joint of a subject in need of treatment. The surgical implant may be in the form of a "cartilage patch" formed out of "synthetic cartilage," i.e., a composition or article of manufacture that contains chondroblasts and/or chondrocytes dispersed within an endogenously produced and secreted extracellular matrix. The extracellular matrix typically comprises collagen fibrils, predominantly fibrils of type II collagen, and sulfated proteoglycans, for example, chondroitin-6-sulfate and keratan sulfate.

In such procedures, the chondroblasts and/or chondrocytes in the cartilage patch are derived from a biological source which may be the same subject into which they are ultimately (re)implanted (autologous implantation), or which may be a different subject (heterologous implantation). In addition, heterologous implantation may utilize chondrocytes obtained from a related or unrelated individual of the same species (allogeneic), or from a different species (xenogeneic). Alternatively, the source from which the chondrocytes are derived may be an established, long-term cell line that is either allogeneic or xenogeneic.

Autologous Chondrocyte Implantation (ACI) is a surgical procedure designed to treat patients who have suffered joint damage, often involving the knee (for a review, see Gilbert, *Am. J. Knee Surg.* 11:42–46, 1998). The poor long term clinical results of existing treatment options stimulated researchers at the Hospital for Joint Diseases in New York during the early 1980s to develop the use of ACI as a treatment alternative. Further development continued at the University of Goteborg and Sahlgrenska University Hospital, Goteborg, Sweden. In a seven-year pilot study, the Swedish group of researchers reported "good-to-excellent results" in 14 of 16 patients with a cartilage defect on the thigh-bone part of the knee treated at least two years earlier. The researchers noted that the vast majority of patients treated on the thigh-bone part of the knee had developed hyaline-like cartilage, similar to normal cartilage, in place of the defects (Brittberg et al., *New England Journal of Medicine* 331:889–895, 1994).

Carticel® (cultured autologous chondrocytes for implantation) is marketed in the United States and Europe by Genzyme Tissue Repair (Cambridge, Mass.). It employs a commercial process to culture a patient's own (autologous) chondrocytes for use in the repair of clinically significant, symptomatic defects of the femoral condyle (medial, lateral, or trochlear) caused by acute or repetitive trauma. As of Mar. 31, 1998, 2,238 surgeons had been trained in the procedure and a total of 1,271 patients had been treated since Genzyme Tissue Repair began marketing the product in 1995. Carticel® is indicated for the repair of clinically significant, symptomatic, cartilaginous defects of the femoral condyle (medial, lateral or trochlear) caused by acute or repetitive trauma.

Treatment with Carticel® starts when an orthopedic surgeon provides Genzyme Tissue Repair with a small sample of a patient's healthy articular cartilage that was removed in an arthroscopic surgical procedure. Technicians at the company's cell processing facility in Cambridge, Mass., use proprietary methods to grow millions of new cartilage cells specifically for that patient. The cells are then delivered to the hospital, where the surgeon implants them into the defect in an open surgical procedure.

During surgery, the physician carefully removes damaged tissue and prepares the defect for introduction of the cultured cells. A small piece of the membranous tissue (periosteum) covering the bone is taken from the patient's lower leg, and sutured over the defect to hold the cells in place. The cultured cells are then implanted under this tissue into the defect where they multiply further and integrate with the surrounding tissue to produce durable new cartilage.

In February 1999, results from Genzyme Tissue Repair's Cartilage Repair Registry, which tracks and measures outcomes for patients treated with Carticel® since its introduction in the U.S. in 1995, were reported. The data demonstrated a positive safety profile for Carticel® and showed highly statistically significant improvements in patient condition at 24 and 36 months after treatment in all four measures: clinician evaluation of knee condition, patient evaluation of knee condition, clinician reports from knee examinations, and patient reports of symptoms.

The clinicians' evaluations showed that 85% of patients with femoral condyle defects were improved after 36 months, while only 8% had scores that declined. The patients' evaluations suggested that 85 percent of the femoral condyle defects were improved, while only 7% had scores that declined.

Data from the registry are consistent with the experience of Swedish orthopedic surgeons who have been using ACI successfully since 1987. New data presented by these surgeons at the annual orthopedic meeting in February 1997 confirmed the long-term benefits shown in Brittberg et al. (1994). The surgeons reported on 92 patients treated 2 to 9 years ago. An overall improvement rate of 88% was reported for all patients treated for lesions of the thigh-bone (femur). More notably, they reported a 96% improvement rate in patients treated for single isolated defects located on the weight bearing areas of the femur, who had otherwise stable knees.

Carticel® is currently marketed under a Biologics License from the U.S. Food and Drug Administration issued in August, 1997. The FDA cleared Carticel® for the "repair of clinically significant symptomatic cartilaginous defects of the femoral condyle (medial, lateral, or trochlear) caused by acute or repetitive trauma."

It is expected that ex vivo manipulation of the chondrocytes used in ACI could be used to improve their therapeutic potential. For example, if the chondrocytes destined for implantation into a patient could be manipulated ex vivo to be more proficient in producing matrix components, the resulting implants would be expected to provide more rapid and/or extensive healing. In certain embodiments, the methods of the present invention circumvent the limitations of ex vivo methods of manipulating chondrocytes that arise from inefficient transfection of human articular chondrocytes with some forms of DNA (Terkeltaub, *J. Clin. Invest.* 94:2173, 1994).

B. Representative Procedures

1. Isolation of Tissue Containing Chondrogenic Cells

Chondrogenic cells useful in the practice of the instant invention may be sampled from a variety of sources in a mammal that contain such cells, for example, preexisting cartilage tissue, perichondrial tissue or bone marrow. Although costal cartilage, nasal cartilage, auricular cartilage, tracheal cartilage, epiglottic cartilage, thyroid cartilage, arytenoid cartilage and cricoid cartilage are useful sources of chondrogenic cells, articular cartilage (from either weight bearing or non-weight bearing joints) is the preferred source. Biopsy samples of articular cartilage may be readily isolated by a surgeon performing arthroscopic or open joint surgery. Procedures for isolating biopsy tissues are well known in the art; see, for example, *"Operative Arthroscopy"* (1991) by McGinty et al., Raven Press, New York, the disclosure of which is incorporated by reference herein.

Perichondrial tissue is the membranous tissue that coats the surface of all types of cartilage, except for articular cartilage. Perichondrial tissue provides nutrients to the chondrocytes located in the underlying unvascularized cartilage tissue. Perichondrial tissue sampled from costal (rib) cartilage of patients suffering from osteoporosis provides a source of chondrogenic cells when the normal articular cartilage is diseased or unavailable. Biopsy samples of perichondrial tissue may be isolated from the surface of costal cartilage or alternatively from the surface of auricular cartilage, nasal cartilage and cricoid cartilage using simple surgical procedures well known in the art (see, e.g., Skoog et al., *Scan. J. Plast. Reconstr. Hand Surg.* 24:89–93, 1990; Bulstra et al., *J. Orthro. Res.* 8:328–335, 1990; and Homminga et al., *J. Bone Constr. Surg* 72:1003–1007, 1990).

It is contemplated also that chondrogenic cells, specifically mesenchymal cells, useful in the practice of the invention may be isolated from bone marrow. Surgical procedures useful in the isolation of bone marrow are well known in the art (see, e.g., Wakitani et al., *J. Bone Joint Surg.* 76:579–591, 1994).

2. Preparation of Denuded Chondrogenic Cells

Protocols for preparing denuded chondrogenic cells from cartilage tissue, perichondrial tissue, and bone marrow are set forth below.

(a) From Articular Cartilage

Articular cartilage, both loaded (weight bearing) and unloaded (non-weight bearing), may be subjected to enzymatic treatment in order to disaggregate the tissue and release denuded chondrogenic cells from the extracellular matrix. Solutions containing proteolytic enzymes, for example, chondroitinase ABC, hyaluronidase, pronase, collagense, or trypsin may be added to articular cartilage tissue in order to digest the extracellular matrix (Watt & Dudhia, *Differentiation* 38:140–147, 1988).

In a preferred procedure, articular cartilage is initially cut into pieces of about 1 mm in diameter or less. This is routinely performed using a sterile scalpel. The minced tissue then is disaggregated enzymatically, for example, by the addition of a solution containing 0.1% collagenase. Approximately 1 ml of collagenase is added per 0.25 ml equivalents of minced tissue. The sample is then mixed and incubated overnight (up to 16 hours) at 37° C. with agitation. Following the overnight digestion, the residual pieces of tissue are harvested by centrifugation, the supernatant is removed, and the remaining cartilage pieces are redigested by the addition of a solution containing, for example, 0.25% collagenase and 0.05% trypsin (available from, for example, Sigma Chemical Co., St. Louis). Approximately 1 ml of 0.25% collagenase, 0.05% trypsin is added per 0.25 ml equivalents of residual tissue. The sample then is mixed and incubated for 2 to 4 hours at 37° C. with agitation. Any remaining tissue is pelleted by centrifugation and the cell suspension harvested. The collagenase trypsin step is repeated 2 to 4 times or until the tissue is completely disaggregated.

The enzymatic reaction is terminated by the addition of tissue culture medium supplemented with approximately 10% fetal bovine serum (FBS) (available from, for example, Hyclone, Logan, Utah). A preferred cell culture medium includes, for example, Dulbecco's minimal essential medium (DMEM) (Sigma) supplemented with 10% FBS. An alternative cell culture medium includes a 1:1 (vol/vol) mixture of Medium 199 (Sigma) and Molecular Cell Developmental Biology Medium 202 (MCDB 202) (Sigma), respectively, supplemented with 10% FBS. Alternatively, another cell culture medium useful in the practice of the invention includes a 3:1 (vol/vol) mixture of DMEM and Ham's F-12 (F12) (Sigma), respectively, supplemented with 10% FBS.

Fractions containing denuded chondrogenic cells are combined, and the cells inoculated into a cell culture dish at a plating density of about $1 \times 10^2$ to $5 \times 10^5$ cells/cm$^2$, preferably about $5 \times 10^2$ to $1 \times 10^5$ cells/cm$^2$, and most preferably about $1 \times 10^3$ to $10^4$ cells/cm$^2$, for cell expansion and testing. Chondrocytes may be isolated from costal cartilage, nasal cartilage, auricular cartilage, tracheal cartilage, epiglottic cartilage, thyroid cartilage, arytenoid cartilage and cricoid cartilage using the aforementioned procedure.

(b) From Perichondrial Tissue

Denuded chondrogenic cells preferably are isolated from perichondrial tissue using the same procedure as described in section 1(a), hereinabove. Briefly, the tissue is minced into pieces of about 1 mm in diameter, or less. The minced tissue is repeatedly digested with proteolytic enzymes, for example, trypsin and collagenase. The resulting denuded cells are inoculated into a cell culture dish at a plating density of about $1 \times 10^2$ to $5 \times 10^5$ cells/cm$^2$, preferably about $5 \times 10^2$ to $1 \times 10^5$ cells/cm$^2$, and most preferably about $1 \times 10^3$ to $1 \times 10^4$ cells/cm$^2$ for cell expansion and testing.

Alternatively, a non-destructive procedure may be used to isolate chondrogenic cells from perichondrial tissue. In this procedure, intact explant tissue is placed in a cell culture dish and incubated in growth medium. The chondrogenic cells located within the tissue migrate out of the tissue and onto the surface of the tissue plate where they begin to proliferate (see, e.g., Bulstra et al., *J. Orthop. Res.* 8:328–335, 1990). Briefly, pieces of the minced explant tissue are placed into a tissue culture plate containing tissue culture medium. A preferred cell culture medium comprises DMEM supplemented with 10% FBS. The explant tissues are incubated at 37° C., 5% CO$_2$ for 3 to 7 days. During this time the chondrogenic cells migrate out of the explant tissue and onto the surface of the tissue culture dish. After reattaching to the surface of the plate, the cells start to proliferate again.

(c) From Bone Marrow

Chondrogenic cells, specifically mesenchymal cells, may be isolated from samples of bone marrow. Procedures useful for the isolation of mesenchymal cells from bone marrow are well known in the art (see, e.g., U.S. Pat. Nos. 5,197,985 and 4,642,120 and Wakitani et al., *J. Bone Joint Surg.* 76:579–591, 1994).

For example, in a preferred method, a plug of bone marrow may be removed surgically from the mammal of interest and added to cell culture medium. Preferred complete growth media are disclosed in U.S. Pat. No. 5,197,985. The mixture then is vortexed to break up the plug of tissue. The resulting suspension is centrifuged to separate bone marrow cells from large pieces of particulate matter, i.e., bone fragments. The cells then are dissociated to give a single cell suspension by forcing the cells through a syringe fitted with a series of 16, 18, and 20 gauge needles. The cells then are plated out into a tissue culture plate at a cell density of about $1 \times 10$ to $1 \times 10^6$ cells/cm$^2$ for selectively separating and/or isolating bone marrow derived mesenchymal cells from the remaining cells present in the suspension.

3. Expansion of Denuded Chondrogenic Cells In Vitro

Chondrogenic cells isolated from cartilage tissue, perichondrial tissue, or bone marrow using the methods described in section 2 hereinabove may be placed in monolayer culture for proliferative expansion. The process enables one to amplify the number of isolated chondrogenic cells. In principal, the artisan may produce essentially an unlimited number of chondrogenic cells and therefore essentially an unlimited amount of synthetic cartilage. It is appreciated, however, that during proliferative expansion the chondrogenic cells dedifferentiate and lose their ability to secrete cartilage specific extracellular matrix. A procedure to assay whether the undifferentiated cells still retain their chondrogenic potential is described hereinbelow.

(a) Cell Proliferation

Protocols for proliferating cells by monolayer culture are well known in the art, see for example, Pollack (supra), and so are not described in detail herein. Briefly, monolayer cultures are initiated by inoculating primary chondrogenic cells, isolated from either cartilage tissue or perichondrial tissue, into a cell culture dish at a plating density density of about $1 \times 10^2$ to $5 \times 10^5$ cells/cm$^2$, more preferably about $5 \times 10^2$ to $1 \times 10^5$ cells/cm$^2$ and most preferably about $1 \times 10^3$ to $1 \times 10^4$ cells/cm$^2$. Chondrogenic cells that have undergone one or more cycles of passaging are also plated out at the same plating densities. Primary chondrogenic cells isolated from bone marrow are plated out into a tissue culture plate at a cell density of about $1 \times 10^5$ to $1 \times 10^6$ cells/cm$^2$. Chondrogenic cells from bone marrow that have undergone one or more cycles of passaging are plated out at plating densities of about $1 \times 10^2$ to $5 \times 10^5$ cells/cm$^2$, more preferably about $5 \times 10^2$ to $1 \times 10^5$ cells/cm$^2$ and most preferably about $1 \times 10^3$ to $1 \times 10^4$ cells/cm$^2$. The chondrogenic cells subsequently are cultured at 37° C., 5% CO$_2$ in cell culture medium.

A preferred cell culture medium comprises DMEM supplemented with 10% FBS. Alternatively, a cell culture medium comprising a 1:1 (vol/vol) mixture of Medium 199 and MCDB 202, respectively, supplemented with 10% FBS may be used. Still another cell culture medium useful in the practice of the invention comprises a 3:1 (vol/vol) mixture of DMEM and F12, respectively, supplemented with 10% FBS.

Once the cell cultures become confluent, i.e., the cells grow to such a density on the surface of the plate that they contact one another, the cells are passaged and inoculated into a new plate. This may be accomplished by initially removing the cell culture medium overlaying the cell monolayer by aspiration, and washing the cell monolayer with phosphate buffered saline (PBS). The PBS is removed, by aspiration, and a solution containing a proteolytic enzyme, i.e., 0.1% trypsin, then is poured onto the monolayer. The proteolytic enzyme hydrolyzes proteins that anchor the cells onto the surface of the plate thereby releasing the cells from the surface of the plate. The proteolytic enzyme in the cell suspension then is inactivated by adding FBS to the suspension to give a final concentration of 10% (vol/vol). The density of cells in the suspension then is estimated and the cells re-plated into a new cell culture plate at a density of about $1 \times 10^2$ to $5 \times 10^5$ cells, more preferably about $5 \times 10^2$ to $1 \times 10^5$ cells, and most preferably about $1 \times 10^3$ to $10^4$ cells per cm$^2$. The passaging procedure may be repeated multiple times, for example up to about 7 to 10 times, until enough cells have been propagated to prepare a piece of cartilage of pre-determined size.

It is appreciated that suspensions of proliferated cells may be cryopreserved indefinitely using techniques well known in the art. See for example, Pollack (supra). Accordingly, populations of chondrogenic cells may be stored for subsequent use whenever a need arises.

(b) Assay for Chondrogenic Potential of Proliferated Cells

Undifferentiated chondrogenic cells, expanded in monolayer culture, may be assayed to determine whether they still retain their chondrogenic potential. This may be performed by culturing the cells in a semi-solid medium in a process called agarose culture. This procedure is described in Benya et al. (*Cell* 30:215–224, 1982). Briefly, proliferated chondrogenic cells are seeded into a solution of warm 2% low melting temperature agarose (LT agarose) (BioRad, Richmond, Calif.). The use of LT agarose permits cells to be seeded into the agarose without thermal damage to the cells. The agarose is cooled to about 39° C. to 41° C. prior to the addition of cells. Approximately $1 \times 10^3$ to $1 \times 10^6$ cells are seeded into 1 ml of the liquid agarose.

The cells are cultured subsequently at 37° C., 5% $CO_2$ for 3 to 4 weeks in a cell culture medium preferably containing DMEM supplemented with 10% FBS. During this time, the chondrogenic cells replicate to from colonies which start to secrete an extracellular matrix. The resulting colonies have the appearance of small "nodules" embedded within the agarose. The colonies may be counted and the chondrogenic proportion of cells determined histochemically and immunohistochemically using procedures well known in the art.

Histochemical Staining: Briefly, agarose gels containing the cells are fixed with 10% formalin in PBS. The samples then are sectioned into 8 to 18 μm sections with a cryo-cut microtome (American Optical). General cellular morphology and tissue phenotype may be assessed by staining the section by the hematoxylin-eosin method well known in the art. Briefly, the resulting section is incubated in a stain comprising hematoxylin dissolved in 5% ethanol for 10 minutes. The section then is washed with water and incubated subsequently in a stain containing 1% eosin in 70% ethanol for 45 seconds. The sections then are washed with 95% ethanol. The nodules of extracellular matrix stain purple under these experimental conditions.

Sulfated proteoglycans in the extracellular matrix may be visualized by incubating the agarose particles in a stain comprising 1% alcian blue in 0.1N hydrochloric acid for 15 to 30 minutes. Alternatively, proteoglycans may be visualized by incubating the agarose particles in a stain comprising 0.2% safranin 0/fast green in 1% acetic acid for 15 to 30 minutes. The stained particles then are washed with water. Sulfated proteoglycans present in the extracellular matrix stain blue and orange, by the two methods, respectively.

Immunohistochemical Staining: The agarose particles containing the chondrogenic cells are sectioned into 8 to 18 um sections with a cryo-cut microtome (American Optical). The sections then are enzymatically digested in order to expose antigenic epitopes present on the extracellular matrix. A preferred enzyme includes the proteolytic enzyme protease type XIV (Sigma). Briefly, the agarose sections are incubated for 90 minutes at room temperature in Tris buffered saline, pH 7.4 (TBS) containing 0.4 mg/ml of protease type XIV. The resulting section then is washed twice with TBS.

Monoclonal antibodies that bind type I collagen (AB745 and MAB1340 from Chemicon International, Timacula, Calif.); type II collagen (PS48 from SanBio Inc., Amsterdam, Holland; CIICI from Hybridoma Bank, Baltimore, Md.); and chondroitin-6-sulfate (MabCs-D from Seikagaku America Inc., Rockville, Md.) may be used to detect the presence of these extracellular components in the agarose particles. Immunostaining may be performed using the VECTASTAIN ABC-AP kit (Vector Laboratory) pursuant to the manufacturer's instructions.

4. Preparation of Synthetic Cartilage Patch

Following proliferation, the chondrogenic cells still having chondrogenic potential are cultured in an anchorage-dependent manner, i.e., in a well having a cell contacting, cell adhesive surface; or in an anchorage-independent manner, i.e., in a well having a cell nonadhesive surface. It has been suggested that chondrogenic cells proliferatively expanded in an anchorage-dependent manner usually dedifferentiate and lose their ability to secrete cartilage-specific type II collagen and sulfated proteoglycan (Schlitz et al., supra; Mayne et al., supra; Mayne et al., supra; Okayama et al., supra; Pacifici & Holtzer, supra; Pacifici et al., supra; West et al., supra; von der Mark, supra; Oegama & Thompson, supra; Benya & Schaffer, supra). U.S. Pat. No. 5,786,217 discloses that undifferentiated chondrogenic cells, when seeded into and cultured in a well having a cell contacting surface that discourages adhesion of cells to the cell contacting surface, redifferentiate and start to secrete cartilage-specific collagen and sulfated proteoglycans, thereby to form a patch of synthetic cartilage in vitro.

In addition, it has been found that culturing the cells in a pre-shaped well enables one to manufacture synthetic cartilage patches of pre-determined thickness and volume. It is appreciated, however, that the volume of the resulting patch of cartilage is dependent not only upon the volume of the well but also upon the number of chondrogenic cells seeded into the well. Cartilage of optimal pre-determined volume may be prepared by routine experimentation by altering either or both of the aforementioned parameters.

(a) Preparation of Pre-Shaped Well

Several approaches are available for preparing pre-shaped wells with cell contacting, cell nonadhesive surfaces. The cell contacting surface of the well may be coated with a molecule that discourages adhesion of chondrogenic cells to the cell contacting surface. Preferred coating reagents include silicon based reagents e.g., dichlorodimethylsilane, or polytetrafluoroethylene based reagents, e.g., Teflon™. Procedures for coating materials with silicon based reagents, specifically dichlorodimethylsilane, are well known in the art. See for example, Sambrook et al. (1989) "Molecular Cloning: A Laboratory Manual", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, e.g., Teflon®. Untreated cell culture plastics, e.g., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other pliable or moldable biocompatible material that inherently discourages the attachment of chondrogenic cells may be useful in the practice of the instant invention.

The size and shape of the well may be determined by the size and shape of the articular cartilage defect to be repaired. For example, it is contemplated that the well may have a cross-sectional surface area of 25 $cm^2$. This is the average cross-sectional surface area of an adult, human femoral chondyle. Accordingly, it is anticipated that a single piece of synthetic cartilage may be prepared in accordance with the invention in order to resurface the entire femoral chondyle. The depth of the well is preferably greater than about 0.3 cm and preferably about 0.6 cm in depth. The thickness of natural articular cartilage in an adult articulating joint is usually about 0.3 cm. Accordingly, the depth of the well should be large enough to permit a cartilage patch of about 0.3 cm to form. However, the well should also be deep enough to contain growth medium overlaying the cartilage patch.

It is contemplated also that a large piece of cartilage prepared in accordance with the invention may be "trimmed" to a pre-selected size and shape by a surgeon performing surgical repair of the damaged cartilage. Trimming may be performed with the use of a sharp cutting implement, e.g., a scalpel, a pair of scissors or an arthroscopic device fitted with a cutting edge, using procedures well known in the art.

The pre-shaped well preferably is cast in a block of agarose gel under aseptic conditions. Agarose is an economical, biocompatible, pliable and moldable material that can be used to cast pre-shaped wells, quickly and easily. As mentioned above, the dimensions of the well may dependent upon the size of the resulting cartilage plug that is desired.

A pre-shaped well may be prepared by pouring a hot solution of molten LT agarose (BioRad) into a tissue culture dish containing a cylinder. The cylinder having dimensions that mirror the shape of the well to be formed. The size and shape of the well may be chosen by the artisan and may be dependent upon the shape of the articular cartilage defect to be repaired. Once the agarose has cooled and solidified around the cylinder, the cylinder is carefully removed with forceps. The surface of the tissue culture dish that is exposed by the removal of the cylinder is covered with molten agarose. This seals the bottom of the well and provides a cell adhesive surface at the base of the well. When the newly added molten LT agarose cools and solidifies, the resulting pre-shaped well is suitable for culturing, and stimulating the redifferentiation of proliferated chondrogenic cells. It is appreciated, however, that alternative methods may be used to prepare a pre-shaped well useful in the practice of the invention.

(b) Growth of Cartilage Patch

Proliferated chondrogenic cells in suspension [from section 3(a), hereinabove] subsequently are seeded into and cultured in the pre-shaped well. The cells are diluted by the addition of cell culture medium to a cell density of about $1\times10^5$ to $1\times10^9$ proliferated chondrogenic cells per ml, or more preferably about $1\times10^6$ to $5\times10^8$ cells per ml, and most preferably about $3\times10^6$ to $2\times10^8$ cells per ml. A preferred cell culture medium comprises DMEM supplemented with 10% FBS. Alternatively, a cell culture medium comprising a 1:1 (vol/vol) mixture of Medium 199 and MCDB 202, respectively, supplemented with 10% FBS may be used. Still another cell culture medium useful in the practice of the invention comprises a 3:1 (vol/vol) mixture of DMEM and F12, respectively, supplemented with 10% FBS.

About $1\times10^3$ to $1\times10^7$ cells, preferably $1\times10^4$ to $1\times10^6$ cells, and most preferably about $5\times10^4$ to $5\times10^5$ cells, produce a piece of synthetic cartilage 1 mm$^3$ in volume. Accordingly, the artisan may produce a patch of synthetic cartilage of pre-determined size by seeding an appropriate number of chondrogenic cells into a pre-shaped well. The cells subsequently are cultured at 37° C., 5% $CO_2$, for 1 to 90 days, preferably 5 to 60 days, and most preferably 10 to 30 days in order to permit secretion of cartilage-specific type II collagen and sulfated proteoglycans thereby to form of synthetic cartilage in vitro. The cell culture medium is removed from the well and replaced with fresh cell culture medium every other day in order to maintain optimal viability of the cells.

Within about four hours of seeding the proliferated chondrogenic cells into the well, the cells coalesce to form a cohesive plug of cells. The cells in the cohesive plug initially secrete type I collagen. After about 4 to 10 days, the cells start to secrete cartilage-specific sulfated proteoglycans and type II collagen. Over the sample period of time, the level of type I collagen synthesis decreases. After prolonged periods of time in culture the collagen expressed by the chondrogenic cells in the well is predominantly type II collagen. It is contemplated however, that the cohesive plug of cells formed within four hours may be removed from the well and surgically implanted into the cartilage defect. It is anticipated that the undifferentiated chondrogenic cells subsequently may redifferentiate in situ thereby to form synthetic cartilage within the joint.

The resulting synthetic cartilage tissue formed in the pre-shaped well may be assayed, biochemically or morphologically, using the procedures described hereinabove prior to implantation into the joint. Briefly, the synthetic cartilage may be sectioned into 8 to 18 $\mu$m sections using a cryomicrotome (American Optical) and resulting sections stained using the procedures described in section 3(b).

It is contemplated that polypeptide growth factors may be added to the chondrogenic cells in the pre-shaped well to enhance or stimulate the production of articular cartilage specific proteoglycans and/or collagen, e.g. (Luyten & Reddi (1992) in "*Biological Regulation of the Chondrocytes*", CRC Press, Boca Raton, Ann Arbor, London, and Tokyo, p.p. 227–236). Preferred growth factors include, but are not limited to transforming growth factor beta (TGF$\beta$), insulin-like growth factor (IGF), platelet derived growth factor (PDGF), epidermal growth factor (EGF), acidic fibroblast growth factor (aFGF), basic fibroblast growth factor (bFGF), hepatocytic growth factor, (HGF) keratinocyte growth factor (KGF), the bone morphogenic factors (BMPs), i.e., BMP-1, BMP-2, BMP-3, BMP-4, BMP-5 and BMP-6 and the osteogenic proteins (OPs), i.e. OP-1, OP-2 and OP-3. Preferred concentrations of TGF$\beta$, IGF, PDGF, EGF, aFGF, bFGF, HGF, and KGF, range from about 1 to 100 ng/ml, more preferably from about 5 to about 50 ng/ml, and most preferably from about 10 to about 20 ng/ml. Preferred concentrations of the BMP's and OP's range from about 1 to about 500 ng/ml, more preferably from about 50 to about 300 ng/ml, and most preferably from about 100 to about 200 ng/ml. However, these particular growth factors are not limiting. Any polypeptide growth factor capable of stimulating or inducing the production of cartilage specific proteoglycans and collagen may be useful in the practice of the instant invention. In addition, it is contemplated that ascorbate may be added to the chondrogenic cells in the pre-shaped well to enhance or stimulate the production of cartilage specific proteoglycans and collagen. Preferred concentrations of ascorbate range from about 1 to about 1000 $\mu$g/ml, more preferably from about 20 to about 500 $\mu$g/ml, and most preferably from about 50 to about 100 ug/ml.

5. Surgical Repair of Articular Cartilage Defect

Cartilage defects in mammals are readily identifiable visually during arthroscopic examination or during open surgery of the joint. Cartilage defects may also be identified inferentially by using computer aided tomography (CAT scanning), X-ray examination, magnetic resonance imaging (MRI), analysis of synovial fluid or serum markers or by any other procedures known in the art. Treatment of the defects can be effected during arthroscopic or open surgical procedures known in the art. Accordingly, once the defect has been identified, the defect may be treated by the following steps of (1) surgically implanting at the pre-determined site, a piece of synthetic articular cartilage prepared by the methodologies described herein, and (2) permitting the synthetic articular cartilage to integrate into pre-determined site.

The synthetic cartilage patch optimally has a size and shape such that when the patch is implanted into the defect, the edges of the implanted tissue contact directly the edges of the defect. In addition, the synthetic cartilage patch may be fixed in placed during the surgical procedure. This can be effected by surgically fixing the patch into the defect with biodegradable sutures, i.e., (available from, e.g.) Ethicon, Johnson & Johnson) and/or by applying a bioadhesive to the region interfacing the patch and the defect. Preferred bioadhesives include, but are not limited to: fibrin-thrombin glues similar to those disclosed in Fr. Pat. No. 2 448 900; Fr. Pat. No. 2 448 901 and EP.S.N. 88401961.3 and synthetic bioadhesives such as those disclosed in U.S. Pat. No. 5,197,973. It is contemplated, however, that alternative types of sutures and biocompatible glues may be useful in the practice of the invention.

In some instances, damaged articular cartilage maybe surgically excised prior the to implantation of the patch of synthetic cartilage. Additionally, the adhesion of the synthetic cartilage patch to the articular cartilage defect may be enhanced by treating the defect with transglutaminase (Ichinose et al., *J. Biol. Chem.* 265:13411–13414, 1990; Najjar et al., in "*Transglutaminases*", Boston, Martinuse-Nijhoff, 1984). Initially, the cartilage defect is dried, for example by using cottonoid, and filled with a solution of transglutaminase. The solution is subsequently removed, for example, by aspiration, leaving a film containing transglutaminase upon the cartilage. The synthetic cartilage patch is implanted subsequently into the defect by the methods described above.

The synthetic cartilage patches preferably are allogeneic, and most preferably autogenic nature. Accordingly, synthetic allogeneic cartilage may be prepared from biopsy tissue isolated from a mammal belonging to the same species as the intended recipient. Synthetic autogenic cartilage may be prepared from biopsy tissue derived from the intended recipient. In addition, the synthetic cartilage may be useful in the repair of human articular cartilage defects. Accordingly, chondrogenic cells may be isolated from: human cartilage tissue, e.g., human articular cartilage (from weight-bearing and non-weight bearing joints), human costal cartilage, human nasal cartilage, human auricular cartilage, human tracheal cartilage, human epiglottic cartilage, human thyroid cartilage, human arytenoid cartilage and human cricoid cartilage; from human perichondrial tissue, e.g., perichondrial tissue sampled from the surface of human costal cartilage, human nasal cartilage, human auricular cartilage, human tracheal cartilage, human epiglottic cartilage, human thyroid cartilage, human arytenoid cartilage and human cricoid cartilage; or from human bone marrow. Surgical procedures for effecting the repair of articular cartilage defects are well known in the art. See, e.g., Luyten & Reddi in "Biological Regulation of the Chondrocytes", CRC Press, Boca Raton, Ann Arbor, London, & Tokyo, pp. 227–236, 1992.

Various modifications of the preceding procedures are known in the art and may be incorporated into the methods of the present invention. For example, U.S. Pat. No. 4,846,835 discloses the seeding of autologous chondrocytes onto a three dimensional collagen matrix which is then inserted in vivo at the site of an articular cartilage lesion and fixed in place using a sutured periosteal flap. U.S. Pat. No. 5,041,138 discloses the in vitro growth of cartilaginous structures by seeding chondrocytes onto a three dimensional biodegradable matrix for subsequent implantation, or, alternatively, proliferating free chondrocytes in vitro, which are then administered directly to the site of damage. U.S. Pat. Nos. 5,723,331 and 5,786,217 disclose methods and compositions for preparing cartilage patches and implanting compositions comprising chondrocytes. U.S. Pat. Nos. 5,736,372, 5,902,741 and 5,932,459 disclose methods of preparing a three-dimensional synthetic polymeric fibrous matrix that can accommodate chondrocytes and that can be cast or molded into a desired shape. U.S. Pat. No. 5,928,945 discloses methods and materials for maintaining enhanced chondrocyte function in cultured chondrocytes by the application of shear flow stress.

C. Treatments to Improve Mitochondrial Function of Chondrocytes

Chondrocytes are treated ex vivo in one or more of the following manners in order to generate or select desirable chondrocytes, i.e., those having improved mitochondrial function.

1. Cybrids.

One method of improving chondrocyte mitochondrial function involves depleting chondrocytes of their endogenous mitochondrial DNA (mtDNA) to produce rho-zero cells, and subsequently introducing into such rho-zero cells mitochondria derived from an animal known not to have or be prone to an arthritic disorder. The resultant cellular hybrids, or cybrids, thus have a nuclear component derived from the parent chondrocytes and a mitochondrial component that is derived from a healthy animal. These cybrid chondrocytes are expected to have improved mitochondrial function and to better carry out chondrocyte-mediated arthritis-limiting activities as a result. If the chondrocytes that are manipulated ex vivo are derived from the same animal into which they are eventually reintroduced, the methods of the invention offer the advantage of improved results due to a decreased potential for immunoreactivity of the implanted cells. That is, manipulated chondrocytes derived from an animal are not expected to trigger a response from that animal's immune system. This advantage improves the efficiency of such methods, as the implanted chondrocytes are expected to be maintained in greater numbers and/or for longer periods of time in the animal, and also reduces the potential for undesirable side-effects of such treatments due to immune reactions and subsequent events (Hyc et al., *Cell. Transplant.* 6:119–124, 1997; Romaniuk et al., *Transpl. Immunol.* 3:251–257, 1995).

Methods for preparing and using rho-zero and cybrid cells are described in U.S. Pat. Nos. 5,840,493 and 5,888,438, published PCT applications WO 95/26973 and WO 98/17826, King and Attardi (*Science* 246:500–503, 1989), Chomyn et al. (*Mol. Cell. Biol.* 11:2236–2244, 1991), Miller et al. (*J. Neurochem.* 67:1897–1907, 1996), Swerdlow et al. (*Annals of Neurology* 40:663–671, 1996), Cassarino et al. (*Biochim. Biophys. Acta* 1362:77–86, 1997), Swerdlow et al. (*Neurology* 49:918–925, 1997), Sheehan et al. (*J. Neurochem.* 68:1221–1233, 1997) and Sheehan et al. (*J. Neurosci.* 17:4612–4622, 1997). Methods of rapidly obtaining rho-zero cells in relatively short periods of time, which may be desirable in some situations, are described in copending U.S. patent application Ser. Nos. 09/069,489 and 09/301,517. It will be appreciated that, with regard to the use of cybrids in cartilage patches, the chondrocytes need not be depleted of their endogenous mitochondrial DNA (i.e., need not be converted to rho-zero cells) before the introduction of exogenous mitochondria, and that the resultant cybrids, although possibly being heteroplasmic with regard to their mtDNA, may nonetheless have enhanced mitochondrial function relative to the chondrocytes from which they are derived.

It will be appreciated by those skilled in the art that this type of ex vivo manipulation will be especially useful when the sequences of the mitochondrial genomes present in the chondrocytes of the patient have been shown to contain one or more mutations that impact mitochondrial function. In these instances, introduction of cybrids comprising nonmutant mitochondrial genomes represents a unique form of genetic therapy. Methods for examining mitochondrial DNA (mtDNA) for mutations are described, for example, in copending U.S. patent application Ser. No. 60/130,447.

(b) Treatment with Mitochondria Protective Agents

Another manner in which chondrocytes are treated ex vivo in order to generate desirable chondrocytes having improved mitochondrial function is to contact the chondrocytes with one or more mitochondria protective(mitoprotective) agents as provided herein, during one or more stages of preparation of the cartilage patch. Such (mitoprotective) agents include, by way of example and not limitation, the antioxidants and anti-apoptotic agents designated herein for the treatment of arthritic disorders. Mitoprotective agents that enhance chondrocyte function, assayed using one or more of the methods described above, are preferred. It may be desirable also to administer one or more mitoprotective agents to the subject or patient after the implantation of the chondrocytes in order to further enhance their mitochondrial function in vivo.

(c) Enrichment for Mitochondrially Proficient Chondrocytes

Another manner in which chondrocytes are treated ex vivo in order to generate desirable chondrocytes having improved mitochondrial function is to select chondrocytes having relatively enhanced mitochondrial function, in order to prepare a population enriched in mitochondrially proficient chondrocytes. This enriched population of chondrocytes having enhanced chondrocyte function is used to prepare a cartilage patch featuring has one or more desirable attributes such as, e.g., more rapid attachment to and repair of a site of joint injury, enhanced ECM production, prolonged stability in vitro or in vivo, etc.

A variety of methods can be used to select chondrocytes having enhanced mitochondrial function. For example, fluorescence-activated cell sorting (FACS) of cells contacted with rhodamine 123, which is taken up by mitochondria as a function of mitochondrial membrane potential ($\Delta\psi_m$), has been used to sort cells according to $\Delta\psi_m$. (see, e.g., al-Rubeai et al., *Cytotechnology* 7:179–186, 1991). A variety of cell types have been sorted by this method, including human fibroblasts (Martinez et al., *Exp. Cell. Res.* 164:551–555, 1986), human spermatozoa (Auger et al., *J. Histochem. Cytochem.* 41:12471251, 1993), lymphocytes (Darzynkiewicz et al., *Proc. Natl. Acad. Sci. USA.* 78:2383–2387, 1981), T cells (Ferlini et al., *Cytrometry* 21:284–293, 1995) and cybrids (Kliot-Fields et al., *Somatic Cell. Genet.* 9:375–389, 1983).

Other methods that can be used to sort cells according to mitochondrial function include fluorescence-activated cell sorting (FACS) of cells loaded with carboxydichlorodihydrofluorescein diacetate and Mito Tracker™ CM-H$_2$Mros (Molecular Probes, Inc., Eugene, Oreg.). The fluorescent signal from which is reflective of oxidative stress state (Karbowski et al., *Biochim. Biophys. Acta* 1449:25–40, 1999). As a further example, FACS of cells loaded with 10-N nonyl acridine orange (NAO) can be used to sort cells based on mitochondrial content (Petit et al., *Cytrometry* 19:304–312, 1995).

Prior to their use in humans, compositions comprising chondrocytes according to the present invention are evaluated in animal models such as dogs, rats (Hyc et al., *Cell Transplant.* 6:119–124, 1997; Romaniuk et al., *Transpla. Immunol.* 3:251–257, 1995; Moskalewski et al., *Cell Transplant.* 2:467–473, 1993), rabbits (Brittberg et al., *Clin. Orthop.* 326:270–283, 1996) or transgenic animal models of arthritic disorders (see, e.g., U.S. Pat. No. 5,675,060).

From the foregoing it will be appreciated that, although specific embodiments of the invention have been described herein for purposes of illustration, various modifications may be made without deviating from the spirit and scope of the invention.

What is claimed is:

1. A method of identifying an agent for altering mitochondrial function in a chondrocyte, comprising:
comparing the rate of mitochondrial ATP synthesis in one or more biological samples obtained from a subject in the presence and absence of a candidate agent, wherein the biological sample comprises a chondrocyte, and wherein an altered rate of mitochondrial ATP synthesis indicates that the agent alters mitochondrial function; and therefrom identifying said agent for altering mitochondrial function in a chondrocyte.

2. A method of determining the suitability of an agent for altering mitochondrial function in a chondrocyte, comprising:
comparing the rate of mitochondrial ATP synthesis in a biological sample obtained from a subject before and after administering to said subject a candidate agent, wherein the biological sample comprises a chondrocyte, and wherein an altered rate of mitochondrial ATP synthesis indicates that the agent alters mitochondrial function; and therefrom determining the suitability of said candidate agent for altering mitochondrial function in a chondrocyte.

3. The method of any one of claim 1 or 2 wherein the chondrocyte is an articular chondrocyte.

4. The method of any one of claim 1 or 2 wherein the biological sample comprises an articular chondrocyte and the step of comparing comprises comparing the rate of ATP synthesis in the absence and presence of transforming growth factor-beta.

5. A method of identifying an agent suitable for altering mitochondrial function in a chondrocyte, comprising:
comparing, in the absence and presence of transforming growth factor-beta, the rate of ATP synthesis in one or more biological samples obtained from a subject in the presence and absence of a candidate agent, wherein the biological sample comprises an articular chondrocyte, and wherein an altered rate of ATP synthesis indicates that the agent alters mitochondrial function; and therefrom determining the suitability of said candidate agent for altering mitochondrial function in a chondrocyte.

6. A method of determining the suitability of an agent for altering mitochondrial function in a chondrocyte, comprising:
comparing, in the absence and presence of transforming growth factor-beta, the rate of ATP synthesis in a biological sample obtained from a subject before and after administering to said subject a candidate agent, wherein the biological sample comprises an articular chondrocyte, and wherein an altered rate of ATP synthesis indicates that the agent alters mitochondrial function; and therefrom determining the suitability of said candidate agent for altering mitochondrial function in a chondrocyte.

* * * * *